United States Patent
Schroeder

(10) Patent No.: US 10,066,004 B2
(45) Date of Patent: *Sep. 4, 2018

(54) EGFR-BASED INHIBITOR PEPTIDES FOR COMBINATORIAL INACTIVATION OF ERBB1, ERBB2, AND ERBB3

(71) Applicant: ARIZONA CANCER THERAPEUTICS, LLC, Tucson, AZ (US)

(72) Inventor: Joyce A. Schroeder, Tucson, AZ (US)

(73) Assignee: ARIZONA CANCER THERAPEUTICS, LLC, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,316

(22) Filed: Apr. 4, 2016

(65) Prior Publication Data

US 2016/0311884 A1    Oct. 27, 2016

Related U.S. Application Data

(63) Continuation-in-part of application No. 13/879,143, filed as application No. PCT/US2011/055894 on Oct. 12, 2011, now Pat. No. 9,585,938.

(Continued)

(51) Int. Cl.
- *C07K 14/00*   (2006.01)
- *C07K 14/71*   (2006.01)
- *C07K 14/47*   (2006.01)

(52) U.S. Cl.
CPC ............. *C07K 14/71* (2013.01); *C07K 14/47* (2013.01); *C07K 14/4703* (2013.01); *C07K 2319/10* (2013.01); *C07K 2319/33* (2013.01)

(58) Field of Classification Search
CPC . C07K 14/71; C07K 14/47; C07K 14/477034
See application file for complete search history.

(56) References Cited

U.S. PATENT DOCUMENTS 7,767,642 B2    8/2010    Schroeder
8,093,208 B2    1/2012    Schroeder
(Continued)

FOREIGN PATENT DOCUMENTS

JP    2005510200    4/2005
JP    2008500815    1/2008
(Continued)

OTHER PUBLICATIONS

Wang et al., (Amino Acids. 2013.44:499-510; ePubJul. 17, 2012).*

(Continued)

*Primary Examiner* — Cherie M Stanfield

(57) ABSTRACT

Inhibitor peptides for combinatorial inactivation of ErbB1, ErbB2, and ErbB3 featuring an EGFR-based peptide and a cell penetrating component such as a protein transduction domain (e.g., PTD4) for enhancing penetration of the EGFR-based peptide into a cell. The EGFR peptide may be from 8 to 30 amino acids in length. The inhibitor peptides can inhibit tumor growth, reduce metastasis, activate apoptosis, activate necrosis, disrupt calcium signaling, and/or increase ROS. In some embodiments, the EGFR-based peptide is at least 50% identical to at least 8 consecutive residues of SEQ ID NO: 1.

3 Claims, 26 Drawing Sheets
(19 of 26 Drawing Sheet(s) Filed in Color)
Specification includes a Sequence Listing.

Related U.S. Application Data

(60) Provisional application No. 62/142,962, filed on Apr. 3, 2015, provisional application No. 62/213,039, filed on Sep. 1, 2015, provisional application No. 62/214,098, filed on Sep. 3, 2015, provisional application No. 61/392,249, filed on Oct. 12, 2010.

(56) References Cited

U.S. PATENT DOCUMENTS

| | | | |
|---|---|---|---|
| 9,585,938 B2* | 3/2017 | Schroeder | C07K 14/71 |
| 2005/0282744 A1 | 12/2005 | Hollingsworth | |
| 2011/0014195 A1 | 1/2011 | Schroeder | |
| 2013/0251727 A1* | 9/2013 | Schroeder | C07K 14/71 |
| | | | 424/142.1 |

FOREIGN PATENT DOCUMENTS

| | | |
|---|---|---|
| JP | 2008503498 | 2/2008 |
| WO | WO 20000034308 A2 | 6/2000 |
| WO | 2002058450 | 8/2002 |
| WO | 2004092339 | 10/2004 |
| WO | 2005042573 | 5/2005 |
| WO | 2005090407 | 9/2005 |
| WO | 2006002114 | 1/2006 |
| WO | 2006113667 | 10/2006 |
| WO | 2009105557 A1 | 8/2009 |
| WO | 2012051247 | 4/2012 |

OTHER PUBLICATIONS

Bird et al., "Chemical Synthesis of Hydrocarbon-Stapled Peptides for Protein Interaction Research and Therapeutic Targeting. Current Protocols in Chemical Biology". Sep. 1, 2011; vol. 3, No. 3; pp. 1-22; p. 2, paragraph 2; p. 3, paragraph 1; p. 8, paragraph 1; figure 3; DOI; 10.1002/9780470559277.ch110042.

Su, "Therapeutic Potential of EGFR Derived Peptides in Breast Cancer [online]. University of Arizona". Apr. 3, 2013. Downloaded from the internet <http://arizona.openrepository.comlarizona/bitstream/1 0150/293486121azu_ etd_12606 sip 1_m.pdf> on Aug. 25, 2016; whole document.

CN; Notification of Third Office Action dated Nov. 19, 2013 in Application No. 200980109625.9.

EPO; European Search Report dated Jul. 31, 2009 in Application No. 06758384.9.

EPO; Office Action dated Jul. 7, 2011 in Application No. 06758384.9.

EPO; Office Action dated Jan. 30, 2013 in Application No. 06758384.9.

EPO; Office Action dated Jul. 9, 2013 in Application No. 06758384.9.

EPO; Office Action dated Sep. 19, 2012 in Application No. 09712807.8.

EPO; Office Action dated Jan. 30, 2013 in Application No. 09712807.8.

JPO; Office Action dated Sep. 7, 2011 in Application No. 2008-506817.

JPO; Office Action dated Jul. 8, 2013 in Application No. 2010-54775I.

JPO; Office Action dated May 1, 2014 in Application No. 2010-54775I.

JPO; Office Action dated Sep. 29, 2014 in Application No. 2013-533960.

Alpaugh et al., "Cooperative Role ofE-Cadherin and Sialyl-Lewis XI A-Deficient MUC1 in the Passive Dissemination of Tumor Emboli in Inflammatory Breast Carcinoma," Oncogene, 21, pp. 3631-3643, (2002).

Alroy, et al., "The ErbB Signaling Network in Embryogenesis and Oncogenesis: Signal Diversification Through Combinatorial Ligand-Receptor Interactions," FEBS Letters, 410, pp. 83-86, (1997).

Anders, et al., "Understanding and Treating Triple-Negative Breast Cancer," Oncology (Williston Park), 22, pp. 1233-1240, and 1243, (2008).

Andersen, et al., "Kinetics and Equilibria in Ligand Binding by Nitrophorins 1-4: Evidence for Stabilization of a Nitric Oxide-F erriheme Complex Through a Ligand-Induced Conformational Trap," Biochemistry, 39, pp. 10118-10131, (2000).

Andrechek, et al., "Tyrosine Kinase Signalling in Breast Cancer: Tyrosine Kinase-Mediated Signal Transduction in Transgenic Mouse Models of Human Breast Cancer," Breast Cancer Res. 2, pp. 211-216, (2000).

Bowie, et al., "Deciphering the Message in Protein Sequences: Tolerance to Amino Acid Substitutions," Science, 247, pp. 1306-1310, (1990).

Brossart, et al., "The Epithelial Tumor Antigen MUC1 is Expressed in Hematological Malignancies and is Recognized by MUC1-Specific Cytotoxic T-lymphocytes," Cancer Res., 61, pp. /184/1-/1850. (2001).

Brooks, et al., "Tat Peptide-Mediated Cellular Delivery: Back to Basics," Advl Drug Deliv. Rev.,57, pp. 559-577, (2005).

USPTO; Restriction Requirement dated May 29, 2008 in Application No. 111404,959.

USPTO; Non-Final Office Action dated Aug. 20, 2008 in Application No. 111404,959.

USPTO; Final Office Action dated Feb. 12, 2009 in Application No. 111404,959.

USPTO; Restriction Requirement dated Dec. 18, 2009 in Application No. 111404,959.

USPTO; Notice of Allowance dated May 25, 2010 in Application No. 111404,959.

USPTO; Non-Final Office Action dated Feb. 24, 2011 in U.S. Appl. No. 12/847,355.

USPTO; Notice of Allowance dated Oct. 7, 2011 in U.S. Appl. No. 12/847,355.

USPTO; Restriction Requirement dated Jul. 25, 2012 in U.S. Appl. No. 12/867,396.

USPTO; Non Final Office Action dated Nov. 7, 2012 in U.S. Appl. No. 12/867,396.

USPTO; Final Office Action dated May 14, 2013 in U.S. Appl. No. 12/867,396.

USPTO; Non-Final Office Action dated Dec. 17, 2014 in U.S. Appl. No. 12/867,396.

AU; Examination Report dated Jul. 11, 2011 in Application No. 200623644I.

AU; Examination Report dated Jun. 19, 2013 in Application No. 2009215503.

Extended European Search Report issued in related European Application No. 11833299.8, dated Mar. 28, 2014.

Dittmann et al., "Nuclear EGFR shuttling induced by ionizing radiation is regulated by phosphorylation at residue Thr654," FEBS Letters, vol. 584, No. 18, Sep. 1, 2010, pp. 3878-3884.

Dietz et al., "Delivery of bioactive molecules into the cell: the Trojan horse approach," Molecular and Cellular Neurosciences, vol. 27, No. 2, Oct. 1, 2004, pp. 85-131.

Bitler. B.G., et al., "Intracellular MUCI Peptides Inhibit Cancer Progression," Clinical Cancer Research, vol. 15, pp. 100-109, (Dec. 31, 2008).

Bitler, B.G., et al., "MUCI regulates nuclear localization and function of the epidermal growth factor receptor," Journal of Cell Science, vol. 123, pp. 1716-1723, (Apr. 20, 2010).

Bitler, B.G., "Determining the Role of MUCI and Beta-Catenin on the Epidermal Growth Factor Receptor Signaling and Localization in Breast Cancer," The University of Arizona, pp. 1-183, (2010).

Katterle, Y., et al., "Antitumour effects of PLC-gammal-(SH2)2-TAT fusion proteins on EGFRIc-erbB-2-positive breast cancer cells," British Journal of Cancer, vol. 90, pp. 230-235, (Jan. 12, 2004).

PCT; International Search Report dated Aug. 29, 2006 in Application No. PCTIUS2006/014485.

PCT; Written Opinion dated Aug. 29, 2006 in Application No. PCTIUS2006/014485.

PCT; International Preliminary Report on Patentability dated Oct. 16, 2007 in Application No. PCTIUS2006/014485.

(56) References Cited

OTHER PUBLICATIONS

PCT; International Search Report and Written Opinion dated May 8, 2009 in Application No. PCTIUS2009/034541.
PCT; International Preliminary Report on Patentability dated Aug. 24, 2010 in Application No. PCTIUS2009/034541.
PCT; International Search Report and Written Opinion dated May 21, 2012 in Application No. PCTIUS20111055894.
PCT; International Preliminary Report on Patentability dated Apr. 16, 2013 in Application No. PCTIUS20111055894.
Ho, et al., "Synthetic Protein Transduction Domains: Enhanced Transduction Potential in Vitro and in Vivo" Cancer Res. 61 pp. 474-477 (2001).
Hollingsworth, et al., "Mucins in Cancer: Protection and Control of the Cell Surface," Nat. Rev. Cancer, 4, pp. 45-60, (2004).
Hong, et al., "Isolation of a Peptide for Targeted Drug Delivery Into Human Head and Neck Solid Tumors," Cancer Res., 60, p. 6551-6556, (2000).
Hsu, et al. "Characterization of a Novel Tripartite Nuclear Localization Sequence in the EGFR Family," J. Biol. Chern., 282 pp. 10432-10440 (2007).
Huber, et al., "The Cadherin Cytoplasmic Domain is Unstructured in the Absence of Beta-Catenin. A possible Mechanism for Regulating Cadherin Turnover," J. Biol. Chern. 276, pp. 12301-12309, (2001).
Huber, et al., "The Structure of the Beta-CateninIE-Cadherin Complex and the Molecular Basis of Diverse Ligand Recognition by Beta-Catenin," Cell, 5, pp. 391-402, (2001).
Jimenez, et al., "Signals Leading to Apoptosis-Dependent Inhibition of Neovascularization by Thrombospondin-1," Nat. Med., 6, pp. 41-48, (2000).
Kittiworakam, et al. "HIV-1 Tat Raises an Adjuvant-Free Humoral Immune Response Controlled by its Core Region and its Ability to Form Cysteine-Mediated Oligomers," J. Biol. Chern.281, pp. 3105-3115, (2005).
Li, et al., "Interaction of Glycogen Synthase Kinase 3~ with the DF3IMUC1 Carcinoma-Associated Antigen and ~ Catenin" Mol. Cell. Biol. pp. 7216-7224 (1998).
Li, et al., "The C-SRC Tyrosine Kinase Regulates Signaling of the Human DF3IMUC1 Carcinoma-Associated Antigen with GSK3 Beta and Beta-Catenin" J. Biol. Chern. 276 pp. 6061-6064 (2001).
Li, et al., "The Epidermal Growth Factor Receptor Regulates Interaction of the Human DF3/MUC1 Carcinoma Antigen with c-Src and Beta-Catenin," J. Biol. Chern., 276: 38, pp. 35239-35242, (2001).
Lilien, et al., "The Regulation of Cadherin-Mediated Adhesion by Tyrosine Phosphorylation! Dephosphorylation of Beta-Catenin" Curro Opin. Cell. Biol. 7 pp. 459-465 (2005).
Lin, et al., "Progression to Malignancy in the Polyoma Middle T Oncoprotein Mouse Breast Cancer Model Provides a Reliable Model for Human Diseases" Am. J. Pathol. 163 pp. 2113-2126 (2003).
Lo, et al., "Nuclear-Cytoplasmic Transport ofEGFR Involves Receptor Endocytosis, Importin Beta1 and CRM1" J. Cell. Biochem. 98 pp. 1570-1583 (2006).
Loftin, et al., "A Novel Copper-Binding Fold for the Periplasmic Copper Resistance Protein CusF," Biochemistry,44 pp. 10533-10540 (2005).
Lopez, et al., "CD44 Attenuates Metastatic Invasion During Breast Cancer Progression," Cancer Res., 65, pp. 6755-6763, (2005).
MacDonald, et al., "Endostatin Binds Tropomyosin. A Potential Modulator of the Antitumor Activity of Endostatin" J. Biol. Chem. 276 pp. 25190-25196. (2001).
Madura, et al., "Activation ofPho in the Injured Axons Following Spinal Cord Injury," EMBO reports 5 pp. 412-416 (2004).
Maes, et al., "Ultra High Resolution Structures of Nitro ph orin 4: Heme Distortion in Ferrous CO and NO Complexes" Biochemistry 44 pp. 12690-12699 (2005).
Maglione, et al., "Transgenic Polyoma Middle-T Mice Model Premalignant Mammary Disease," Cancer Res., 61, pp. 8298-8305, (2001).

Michelson, et al. "Beta-Catenin is a Downstream Effector ofWnt-Mediated Tumorigenesis in the Mammary Gland" Oncogene 20 pp. 5093-5099 (2001).
Morrison, et al., "Combinatorial Alanine-Scanning," Curro Opin. Chern. Biol., 5, pp. 302-307, (2001).
Noguchi, et al., "Protein Transduction Technology: A Novel Therapeutic Perspective," Acta Medical Okayama 60. pp. 1-11 (2006).
Ola Yioye, et al., "ErbB-I and ErbB-2 Acquire Distinct Signaling Properties Dependent Upon Their Dimerization Partner," Mol. Cell. Biol., 18 pp. 5042-505I (1998).
Olayioye, et al., "ErbB Receptor-Induced Activation of Stat Transcription Factors is Mediated by Src Tyrosine Kinases" J. Biol. Chern. 274. pp. 17209-17218 (1999).
Packer, et al., "Expression of the Cell Surface Mucin Gene Family in Adenocarcinomas," Int. J. Oncol. 25 pp. 1119-1126 (2004).
Parker, et al., "Distant Metastasis in Breast Cancer: Molecular Mechanisms and Therapeutic Targets" Cancer Bio. Ther. 2 pp. 14-21 (2003).
Piedra, et al., "Regulation of Beta-Catenin Structure and Activity by Tyrosine Phosphorylation," J. Biol. Chern., 276, pp. 20436-20443, (2001).
Pintens, et al., "Triple Negative Breast Cancer A Study from the Point of View of Basal CK5/6 and HER-I" J. Clin. Pathol. 62 pp. 624-628, (2009).
Pochampalli, et al., "MUCI is a Novel Regulator of ErbBI Receptor Trafficking," Oncogene, 26, pp. 1693-1701, (2007).
Pochampalli, et al., "Transforming Growth Factor Alpha Dependent Cancer Progression is Modulated by Muc1" Cancer Res. 67 pp. 6591-6598 (2007).
Polakis, P., "Wnt Signaling and Cancer," Genes Dev., 14, pp. 1837-1851, (2000).
Price, et al., "Tumorigenicity and Metastasis of Human Breast Carcinoma Cell Lines in Nude Mice" Cancer Res. 50, pp. 717-721 (1990).
Ren, et al., "Human MUCI Carcinoma-Associated Protein Confers Resistance to Genotoxic Anticancer Agents" Cancer Cell 5: pp. 163-175 (2004).
Roberts, et al. "Crystal Structure and Electron Transfer Kinetics ofCueO, a Multicopper Oxidase Required for Copper Homeostasis in *Escherichia coli*," Proc. Natl. Acad. Sci. USA, 99, pp. 2766-2771, (2002).
Schneider, et al., "Protein Evolution: Structure-Function Relationships of the Oncogene Beta-Catenin in the Evolution of Multicellular Animals," J. Exp. Zool. Mol. Dev. Evol., pp. 295, 25-44, (2003).
Schroeder, et al., "MUCI Alters Beta-Catenin-Dependent Tumor and Promotes Cellular Invasion" Oncogene 22 pp. 1324-1332 (2003).
Schroeder, et al., "MUCI Overexpression Results in Mammary Gland Tumorigenesis and Prolonged Alveolar Differentiation" Oncogene 23: pp. 5739-5747 (2004).
Schroeder, et al., "Dynamic Expression and Activation ofERBB Receptors in the Developing Mouse Mammary Gland" Cell Growth Differ. 9 451-464 (1998).
Schroeder, et al., "Transgenic Mice Reveal Roles for TGFalpha and EGF Receptor in Mammary Gland Development and Neoplasia" J. Mammary Gland Biol. Neoplasia 2 pp. 119-129 (1997).
Schroeder, et al., "Transgenic MUCI Interacts With Epidermal Growth Factor Receptor and Correlates with Mitogen-Activated Protein Kinase Activation in the Mouse Mammary Gland," J. Biol. Chern., 276, pp. 13057-13064, (2001).
Schroeder, et al., "Cooperative Induction of Mammary Tumorigenesis by TGFalpha and Wnts," Oncogene 19 pp. 3193-3199 (2000).
Schroeder, et al., "ErbB-Beta-Catenin Complexes are Associated with Human Infiltrating Ductal Breast and Murine Mammary Tumor Virus (MMTV)-Wnt-I and MMTV-c-Neu Transgenic Carcinomas," J. Biol. Chern, 277, pp. 22692-22698, (2002).
Schwarze, et al., "Protein Transduction: Umestricted Delivery into All Cells?" Trends Cell Biol., 10 pp. 290-295 (2000).
CIPO; Office Action dated Sep. 5, 2012 in Application No. 2601823.
CIPO; Office Action dated May 21, 2013 in Application No. 2601823.

(56) References Cited

OTHER PUBLICATIONS

CN; Notification of First Office Action dated Sep. 21, 2010 in Application No. 200680011038.2.
CN; Notification of Second Office Action dated Feb. 18, 2011 in Application No. 200680011038.2.
CN; Notification of Third Office Action dated May 18, 2011 in Application No. 200680011038.2.
CN; Notification of Decision of Rejection dated Oct. 25, 2011 in Application No. 200680011038.2.
CN; Notification of Third Office Action dated Jul. 17, 2013 in Application No. 200680011038.2.
CN; Notification of First Office Action dated Jul. 9, 2012 in Application No. 200980109625.9.
CN; Notification of Second Office Action dated Mar. 12, 2013 in Application No. 200980109625.9.
JPO; Office Action dated Aug. 17, 2015 in Application No. 2014-174796.
AU; Notice of Acceptance dated Oct. 29, 2015 in Application No. 2011316653.
USPTO; Final Office Action dated Jun. 25, 2015 in U.S. Appl. No. 12/867,396.
M.C. Berenbaum, "Synergy, additivism and antagonism in immunosuppresstion," Welcome Laboratories of Experimental Pathology, Variety Club Research Wing, SI. Mary's Hospital Medical School, London, pp. 1-18, (1976).
Weisenthal, Human Tumor Assay Journal, on-line at http://weisenthal.org/synergy1.html, 1 page, (2012).
AU; Examination Report dated Jan. 8, 2015 in Application No. 2011316653.
CIPO; Office Action dated Jan. 29, 2015 in Application No. 2714939.
Lazar et al., "Transforming Growth Factor: Mutation of Aspartic Acid 47 and Leucine 48 Results in Different Biological Activities," Mol. Cell. Bio., 8, pp. 1247-1252, (1988).
Schwarze, et al., "In Vivo Protein Transduction: Delivery of a Biologically Active Protein Into the Mouse" Science 285: 5433 pp. 1569-1572 (1999).
Shutman, et al., "The Cyclin D1 Gene is a Target of the Beta-CateniniLEF-1 Pathway," Proc. Natl. Acad. Sci. USA, 96, pp. 5522-5527, (1999).
Snyder, et al., "Cell Penetrating Peptides in Drug Delivery," Pharm. Res., 21, pp. 389-393, (2004).
Spicer, et al., "Delayed Mammary Tumor Progression in Muc-1 Null Mice," J. Biol. Chern., 270, pp. 30093-30101 (1995).
Spicer, et al., "Analysis of Mammalian MUC1 Genes Reveals Potential Functionally Important Domains" Mammalian Genome 6 pp. 885-888 (1995).
Takahashi, et al., "Expression of MUC 1 on Myeloma Cells and Induction ofHLA Unrestricted CTL Against MUC1 from a Multiple Myeloma Patient" J. Immunol. 153 pp. 2102-2109 (1994).
Teruya-Feldstein, et al., "MUC-1 Mucin Protein Expression in B-Cell Lymphomas," Appl. Immunohistochem . . . Mol. Morphol., 11, pp. 28-32, (2003).
Tetsu et al., "Beta-Catenin Regulates Expression ofCyclin D1 in Colon Carcinoma Cells," Nature, 398: 6726, pp. 422-426 (1999).
Trivedi, et al., "Augmentation of Leukocyte Infiltration in Murine Tumors Expressing B-Cell Derived but not Nasopharyngeal Carcinoma Derived EBV Membrane Protein LMP1," J. Med. Virol., 60, pp. 417-424, (2000).
Tsukamoto, et al., "Expression of the Int-1 Gene in Transgenic Mice is Associated with Mammary Gland Hyperplasia and Adenocarcinomas in Male and Female Mice," Cell, 55, pp. 619-625, 1988).
Wadia, et al., "Transducible TAT-HA Fusogenic Peptide Enhances Escape of TAT-Fusion Proteins After Lipid Raft Macropinocytosis" Nat. Med. 10 pp. 310-315 (2004).
Wadia, et al., "Transmembrane Delivery of Protein and Peptide Drugs by TAT-Mediated Transduction in the Treatment of Cancer," Adv. Drug Deliv. Rev. 57:4, pp. 579-596 (2005).
Webster, et al., "Requirement for Both Shc and Phosphatidylinositol3' Kinase Signaling Pathwaysin Polyomavirus Middle T-Mediated Mammary Tumorigenesis," Mol. Cell. Biol. 18, pp. 2344-2359,(1998).
Weichsel, et al., "Nitric Oxide Binding to Nitrophorin 4 Induces Complete Distal Pocket Burial," Nat. Struct. Biol., 7 pp. 551-554 (2000).
Weichsel, et al., "Heme-Assisted S-Nitrosation of a Proximal Thiolate in a Nitric Oxide Transport Protein" Proc. Natl. Acad. Sci. USA 102 pp. 594-599 (2005).
Weisenthal, "Synergy Analysis of Classic and Newer Drug Combinations," Human Tumor Assay J., \Vyv\v. welsenthal.org/svnergvl, (2012).
White, et al., "Targeted Disruption of Beta1-Integrin in a Transgenic Mouse Model of Human Breast Cancer Reveals an Essential Role In Mammary Tumor Induction," Cancer Cell, 6, pp. 159-170,(2004).
Xing, et al., "Crystal Structure of a Beta-Cateninl Axin Complex Suggests a Mechanism for the Beta-Catenin Destruction Complex" Genes Dev. 17, pp. 2753-2764, (2003).
Yamamoto, et al., "Interaction of the DF3IMUC1 Breast Carcinoma-Associated Antigen and Beta-Catenin in Cell Adhesion" J. Biol. Chern. 272:19 pp. 12492-12494 (1997).
Zotter, et al., "Tissue and Tumor Distribution of Human Polymorphic Epithelial Mucin," Cancer Rev. 11-12 pp. 55-101 (1988).
Zrihan-Licht et al., "Tyrosine Phosphorylation of the MUC1 Breast Cancer Membrane Proteins.Cytokine Receptor-Like Molecules" FEBS Lett. 356 pp. 130-136 (1994).
Principles of Cancer Therapy: Merck Manual Professional, Chapter 149, Section 11, (2005).
Gefitinib-MeSH-N CBI,wwww.ncbi.nlm.nih.gov/mesh?term=getfitnib, (2012).
Carpenter, "The EGF Receptor: A Nexus for Trafficking and Signaling," Bioessays, 22, pp. 697-707 (2000).
Choi, et al., "Erlotinib Prevents Pulmonary Metastasis in Curatively Resected Breast Carcinoma Using a Mouse Model" Oncol. Rep., 16, pp. 119-122, (2006).
Console, et al., "Antennapedia and HIV Transactivator of Transcription (TAT) 'Protein Transduction Domains' Promote Endocytosis of High Molecular Weight Cargo Upon Binding to Cell Surface Glycosaminoglycans," J. Biol. Chern., 278, pp. 35109-35114, (2003).
Dassonville et al., "EGFR Targeting Therapies: Monoclonal Antibodies Versus Tyrosine Kinase Inhibitors: Similarities and Differences," Crit. Rev. Oncol.IHematol., 62, pp. 53-61, (2007).
Dawson, et al., "Three Distinct D-Amino Acid Substitutions Confer Potent Antiangiogenic Activity on an Inactive Peptide Derived from a Thrombospondin-1 Type 1 Repeat," Mol. Pharmacol., 55, pp. 332-338, (1999).
Finn, et al., "Estrogen Receptor, Progesterone Receptor, Human Epidermal Growth Factor Receptor 2 (HER2), and Epidermal Growth Factor Receptor Expression and Benefit from Lapatinib in a Randomized Trial of Paclitaxel With Lapatinib or Placebo as First-Line Treatment In HER2- Negative or Unknown Metastatic Breast Cancer," J. Clin. Oncol. 27. pp. 3908-3915 (2009).
Friess, et al., "Combination Treatment with Erlotinib and Pertuzumab Against Human Tumor Xenografts is Superior to Monotherapy," Clin. Cancer Res., 14, pp. 5300-5309, (2005).
Gottlieb, et al., "Natural Biology of Polyoma virus Middle T Antigen," Microbial Mol. Bio. Rev.,65 pp. 288-318• second and third pages table of contents (2001).
Green, et al., "Beta-Catenin Antisense Treatment Decreases Beta-Catenin Expression and Tumor Growth Rate in Colon Carcinoma Xenografts," J. Surgical Res., 101:1, pp. 16-20, (2001).).
Guy, et al., "Induction of Mammary Tumors by Expression of Polyoma virus Middle T Oncogene: A Transgenic Mouse Model for Metastatic Disease," Mol. Cell. Biol., 12, pp. 954-961, (1992).
Guy, et al., "Expression of the Neu Protooncogene in the Mammary Epithelium of Transgenic Mice Induces Metastatic Disease" Proc. Natl. Acad. Sci. USA 89 pp. 10578-10582 (1992).
Ha, et al., "Mechanism of Phosphorylation-Dependent Binding of APC to Beta-Catenin and its Role in Beta-Catenin Degradation" Mol. Cell 15 pp. 511-521 (2004).

(56) References Cited

OTHER PUBLICATIONS

Hadzisejdic, et al., "Nuclear EGFR in Ductal Invasive Breast Cancer: Correlation with Cyclin-DI and Prognosis" Mod. Pathol. 23 pp. 392-403 (2010).
Harada, et al., "Antitumor Protein Therapy; Application of the Protein Transduction Domain to the Development of a Protein Drug for Cancer Treatment" Breast Cancer 13 pp. 16-26 (2006).
He, et al., "Identification of c-MYC as a Target of the APC Pathway," Science, 281, pp. 1509-1512, (1998).
Hilkens, et al., "Is Episialin!MUC1 Involved in Breast Cancer Progression?" Cancer Letters, 90, pp. 27-33 (1995).

* cited by examiner

FIG. 1

| Name | | Sequence | Change | Day 3 Survival | SEQ ID NO: |
|---|---|---|---|---|---|
| hEGFR | ENLS-1 | PTD4-FMRRRHIVRKRTLRRLLQERE | | 5% | 13 |
| hEGFR | ENLS-2 | PTD4-FMRRRHIVRKRTL∗∗∗∗∗∗∗∗ | -RRLLQERE | 73% | 19 |
| hEGFR | ENLS-3 | PTD4-∗∗∗∗∗∗IVRKRTLRRLLQERE | FMRRRH- | 37% | 16 |
| hEGFR | ENLS-4 | PTD4-∗∗RRRHIVRKRTLRR∗∗∗∗∗∗ | FM--LLQERE | 78% | 20 |
| hEGFR | ENLS-5 | PTD4-∗∗∗∗∗∗∗∗∗∗RTLRRLLQERE | FMRRRHIVRK- | 62% | 18 |
| hEGFR | EBL-1 | PTD4-∗∗∗∗∗∗∗∗∗∗∗∗∗∗LLQERELVEPLT | Basolateral Domain | 96% | 22 |
| hEGFR EBL-1AA | cEBL-1 | PTD4-∗∗∗∗∗∗∗∗∗∗∗∗∗∗AAQEREAAEPLT | EBL-1 L and V to A | 98% | 25 |
| hEGFR | abcCPv1 | PTD4-FRMHRIRVRTKLRLRLRQERE | Scramble ENLS-1 | 5% | 14 |
| hEGFR 428K>A | abcCPv2 | PTD4-FMAAAHIVAAATLAALLQERE | A for R and K | Not Sol. | 26 |
| hEGFR | cENLS-2 | PTD4-FRMHRIRVRTKLR∗∗∗∗∗∗∗∗ | Scramble ENLS-2 | 83% | 21 |
| hEGFR | cENLS-3 | PTD4-∗∗∗∗∗∗IVRTKLRLRLRQERE | Scramble ENLS-3 | 51% | 17 |
| hEGFR 428K>D | abcCPv4 | PTD4-∗∗RDRHIVRDRTLRD∗∗∗∗∗∗ | ENLS-4 R to D | 99% | 23 |
| hEGFR 428K>D | abcCPv5 | PTD4-FMRDRHIVRDRTLRDLLQERE | ENLS-1 R to D | 100% | 24 |
| hEGFR 428K>Q | abcCPv6 | PTD4-FMRQRHIVRQRTLRQLLQERE | ENLS-1 R to Q | 35% | 15 |

FIG. 2A    Predicted Structure of Peptides
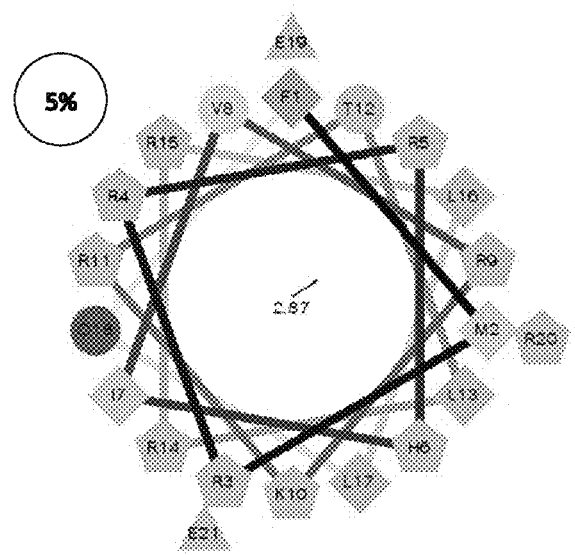
SEQ ID NO: 1 (Related to ENLS-1/EJ1)
SEQ ID NO: 2 (related to nlsCPv1/Scramble ENLS-1)

FIG. 2B
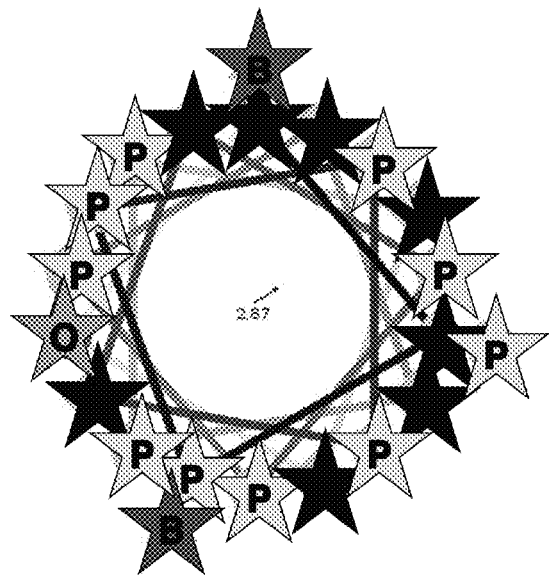
SEQ ID NO: 1 (Related to ENLS-1/EJ1)
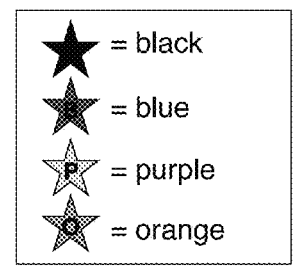
★ = black
★ = blue
★ = purple
★ = orange
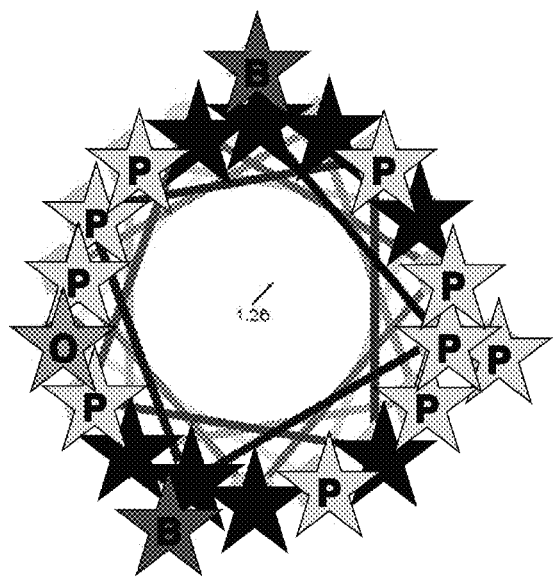
SEQ ID NO: 2 (related to nlsCPv1/Scramble ENLS-1)

FIG. 3A
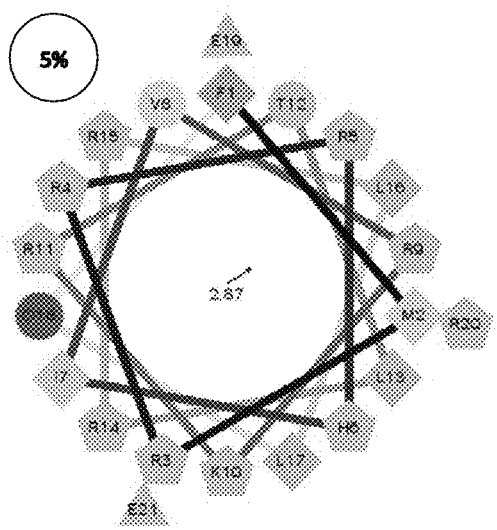
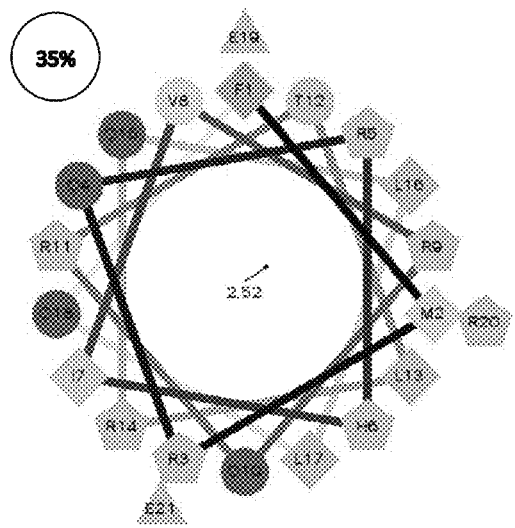
SEQ ID NO: 1 (Related to ENLS-1/EJ1)   SEQ ID NO: 3 (Related to nlsCPv6/EJ11)
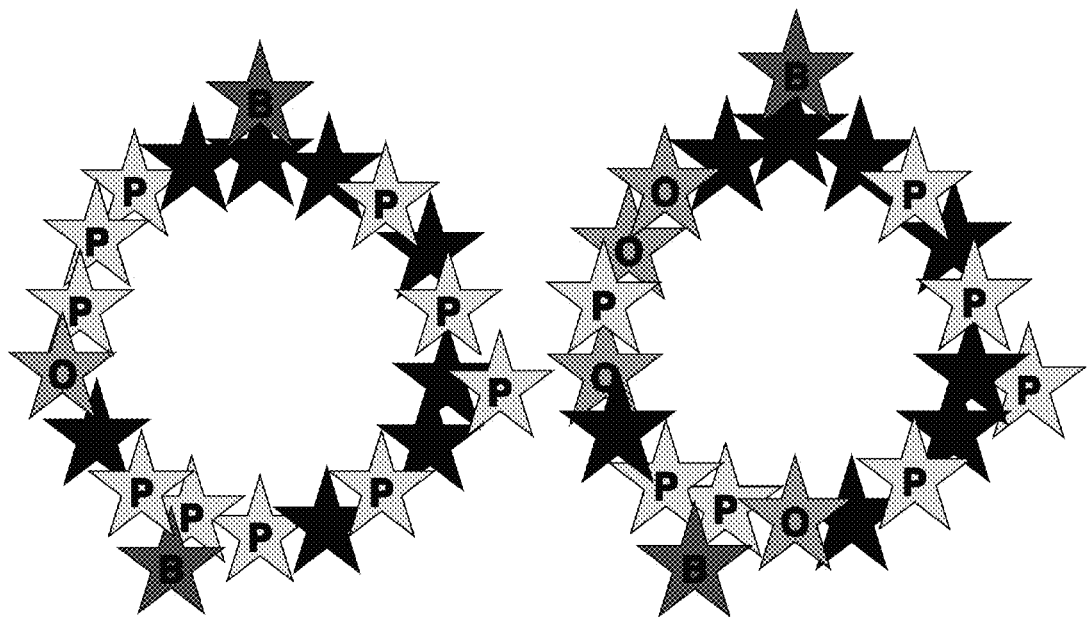
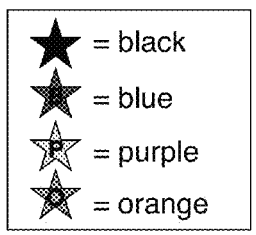
★ = black
★ = blue
★ = purple
★ = orange

FIG. 3B
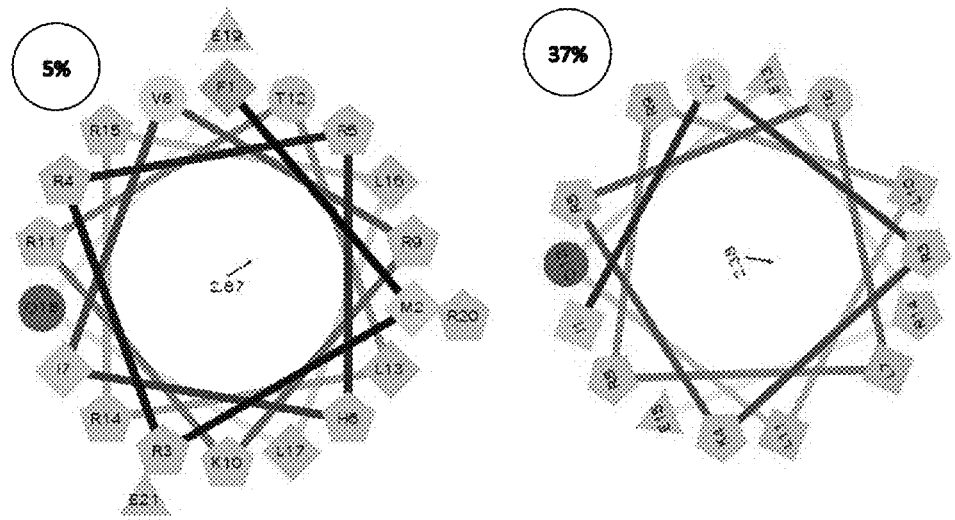
SEQ ID NO: 1 (Related to ENLS-1/EJ1)     SEQ ID NO: 4 (Related to ENLS-3/EJ3)
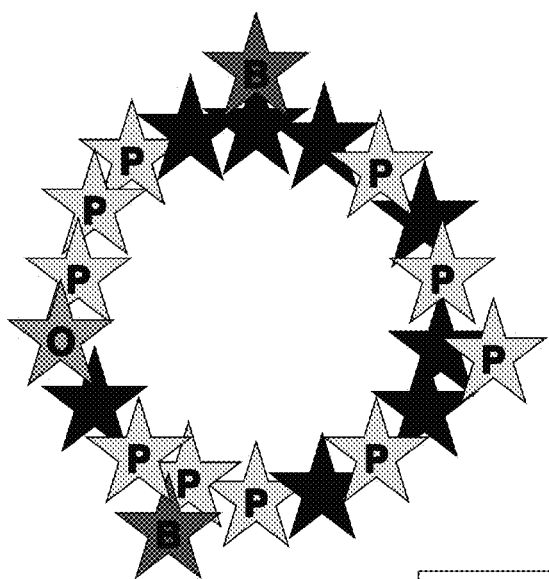
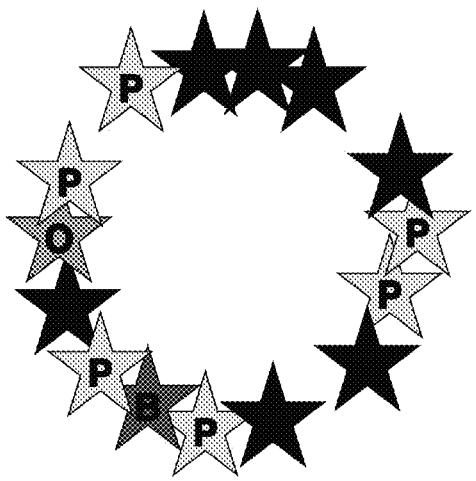
★ = black
★ = blue
★ = purple
★ = orange FIG. 3C
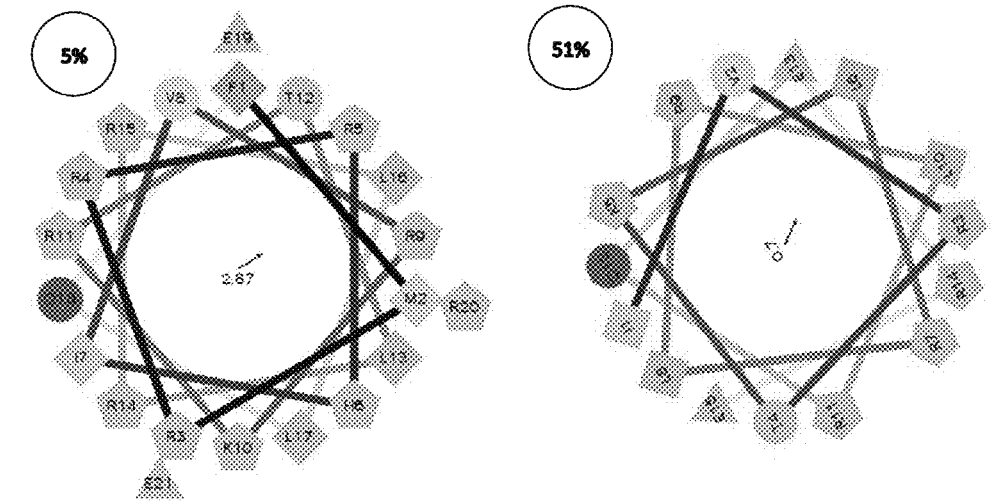
SEQ ID NO: 1 (Related to ENLS-1/EJ1)   SEQ ID NO: 5 (Related to ENLS-3 scramble/cENLS-3)
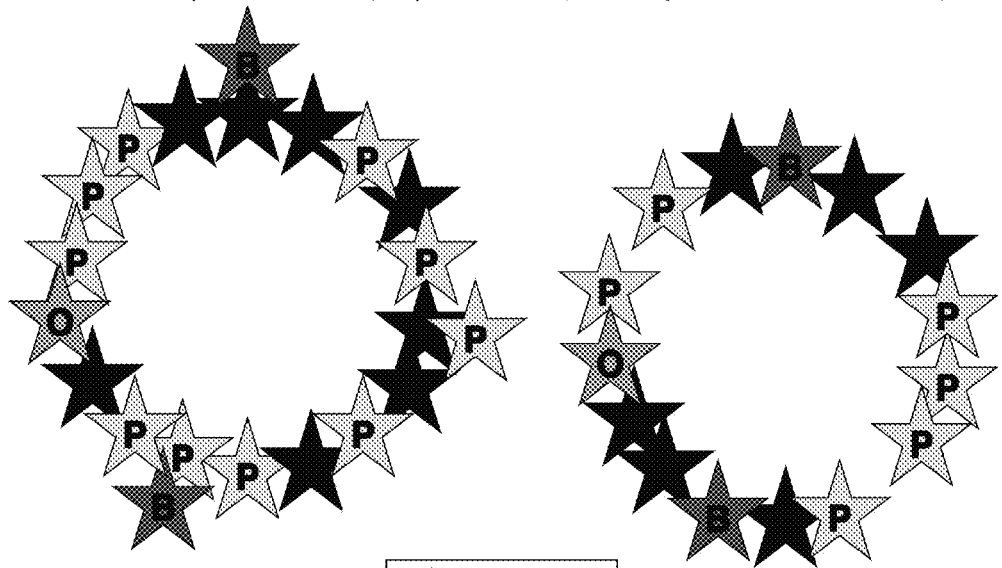
★ = black
★ = blue
★ = purple
★ = orange

FIG. 3D
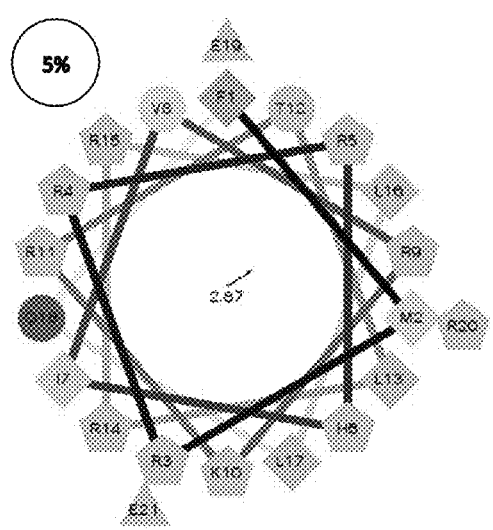
SEQ ID NO: 1 (Related to ENLS-1/EJ1)
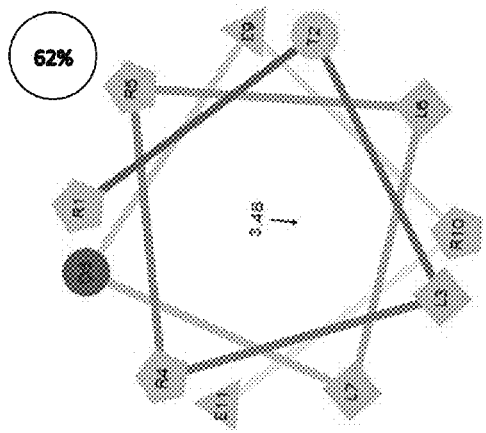
SEQ ID NO: 6 (Related to ENLS-5/EJ5)
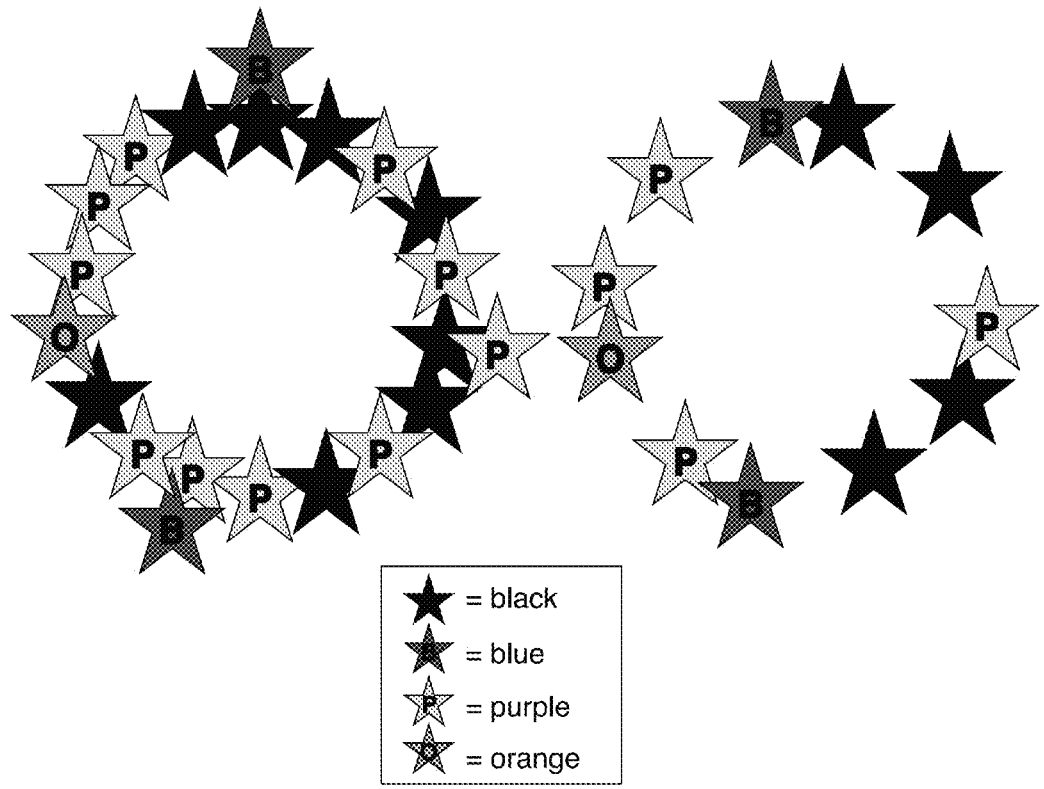
★ = black
★ = blue
☆ = purple
☆ = orange

FIG. 3E
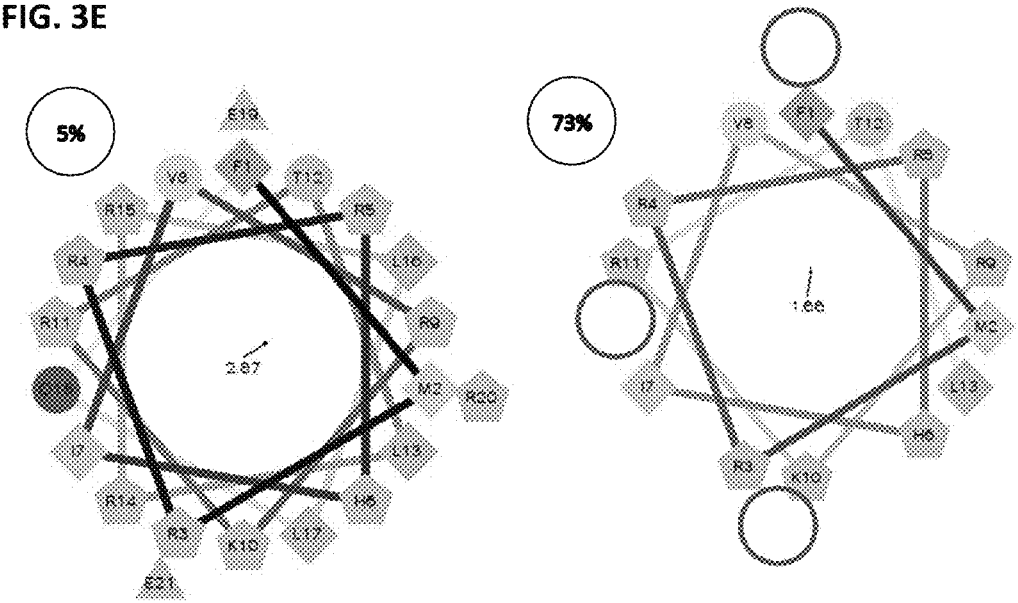
SEQ ID NO: 1 (Related to ENLS-1/EJ1)   SEQ ID NO: 7 (Related to ENLS-2/EJ2)
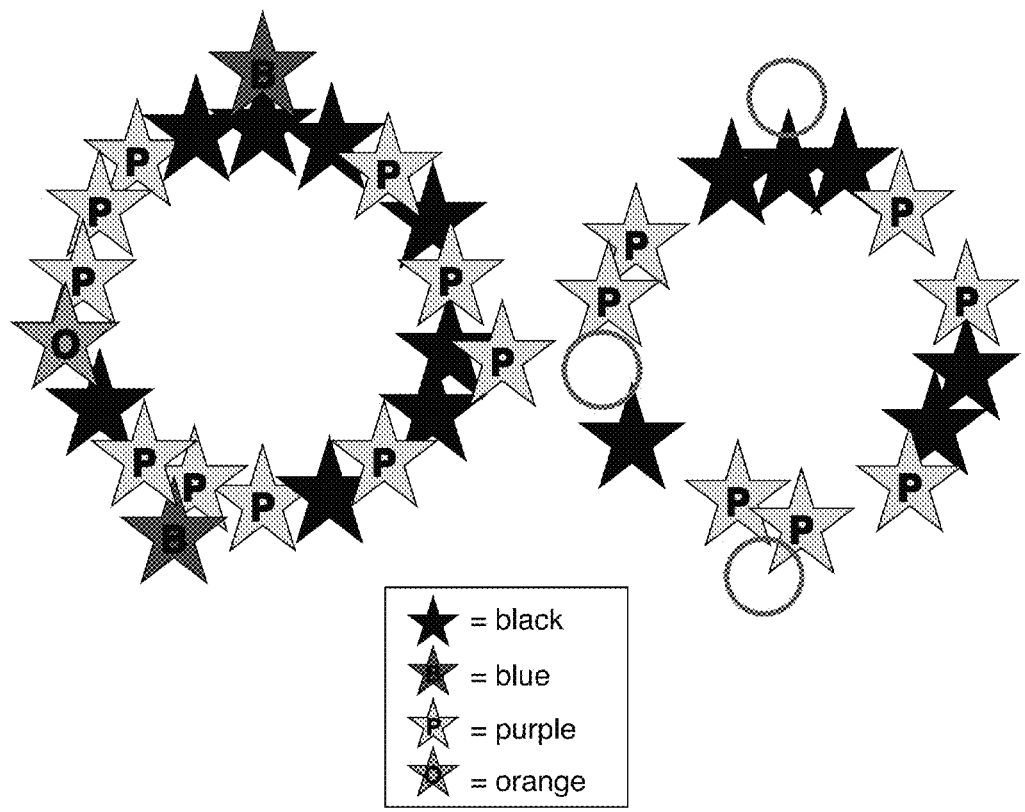

FIG. 3F
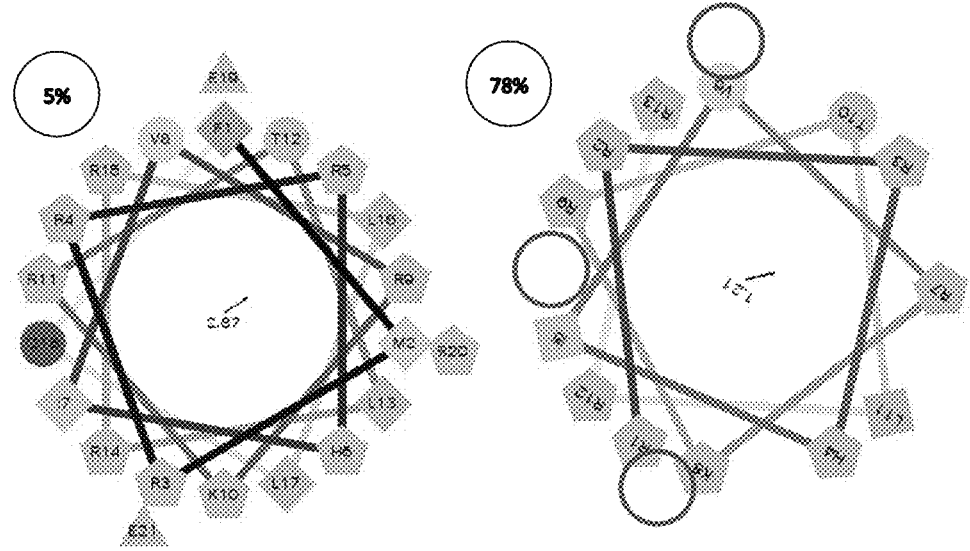
SEQ ID NO: 1 (Related to ENLS-1/EJ1)     SEQ ID NO: 8 (Related to ENLS-4/EJ4)
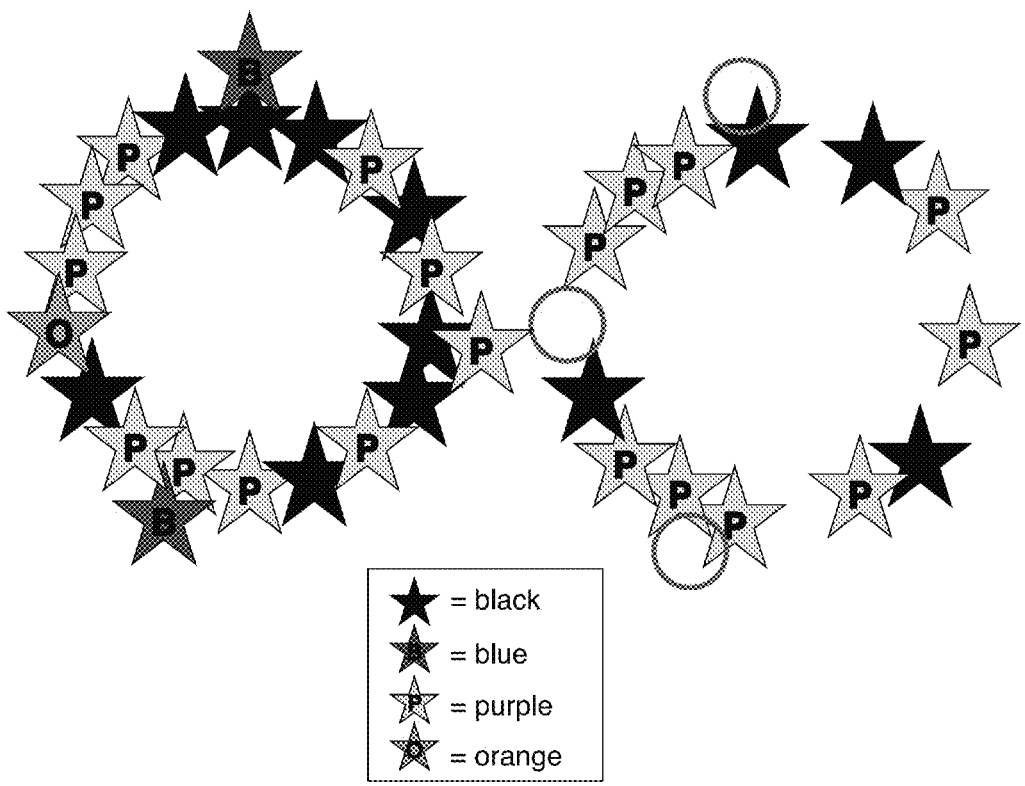

FIG. 3G
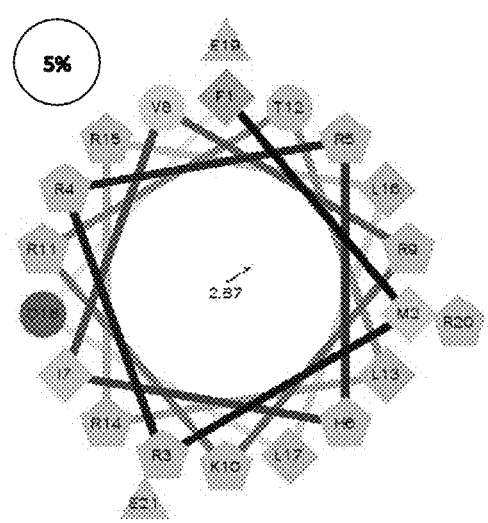
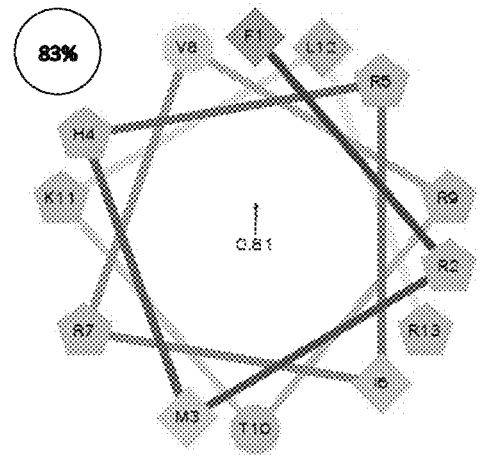
SEQ ID NO: 1 (Related to ENLS-1/EJ1)   SEQ ID NO: 9 (Related to cENLS-2/Scramble ENLS-2)
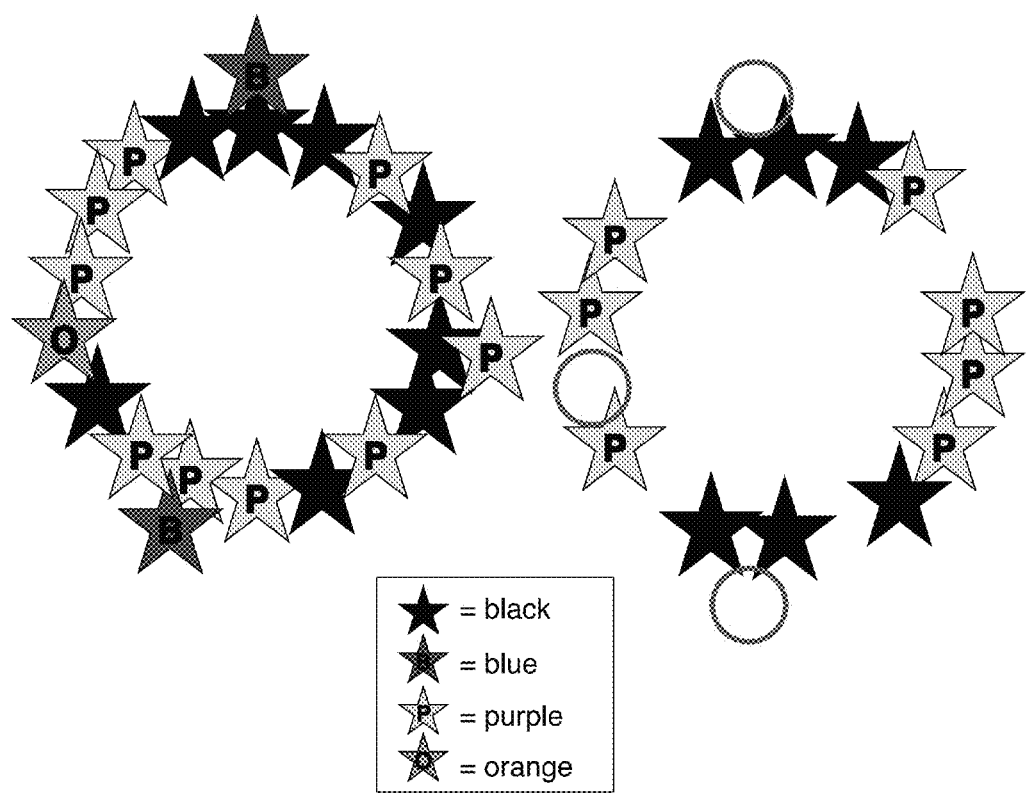

FIG. 3H
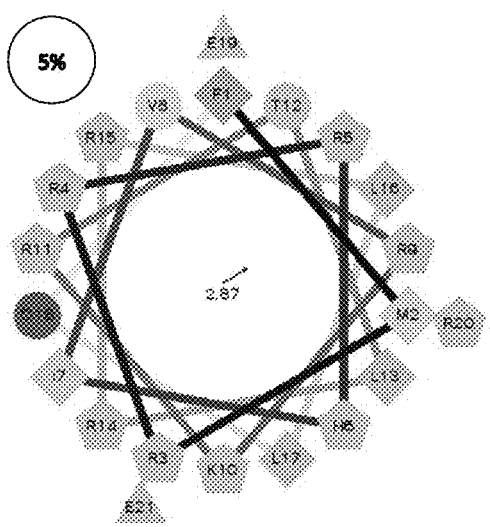
SEQ ID NO: 1 (Related to ENLS-1/EJ1)
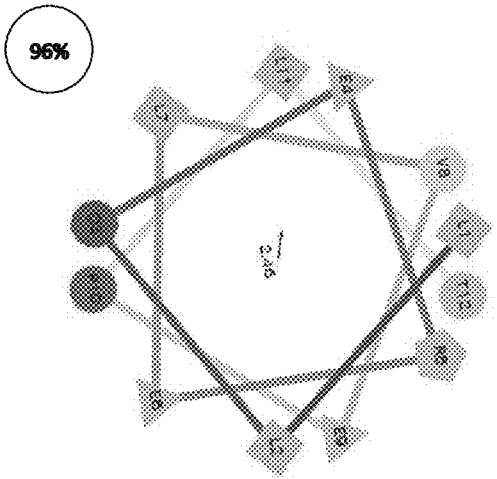
SEQ ID NO: 10 (Related to EBL-1/EJ6)
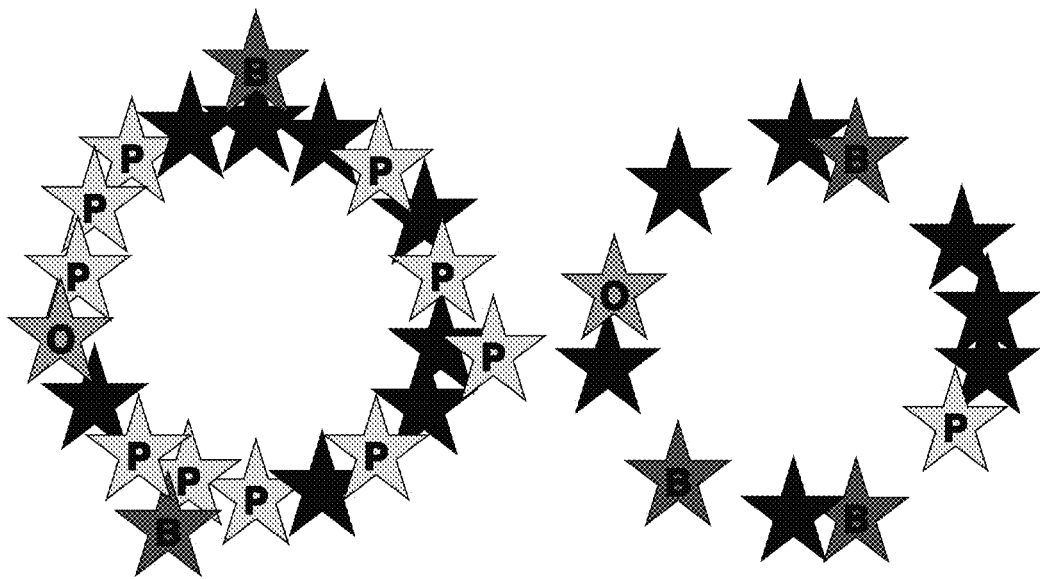
★ = black
★ = blue
★ = purple
★ = orange FIG. 3I
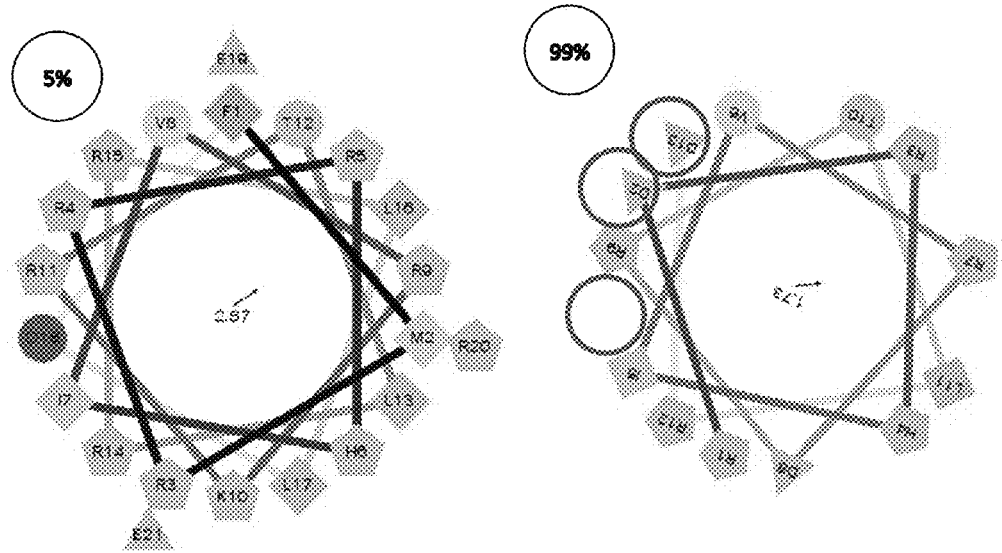
SEQ ID NO: 1 (Related to ENLS-1/EJ1)    SEQ ID NO: 11 (Related to ENLS-4 scramble (nlsCPv4)/EJ9)
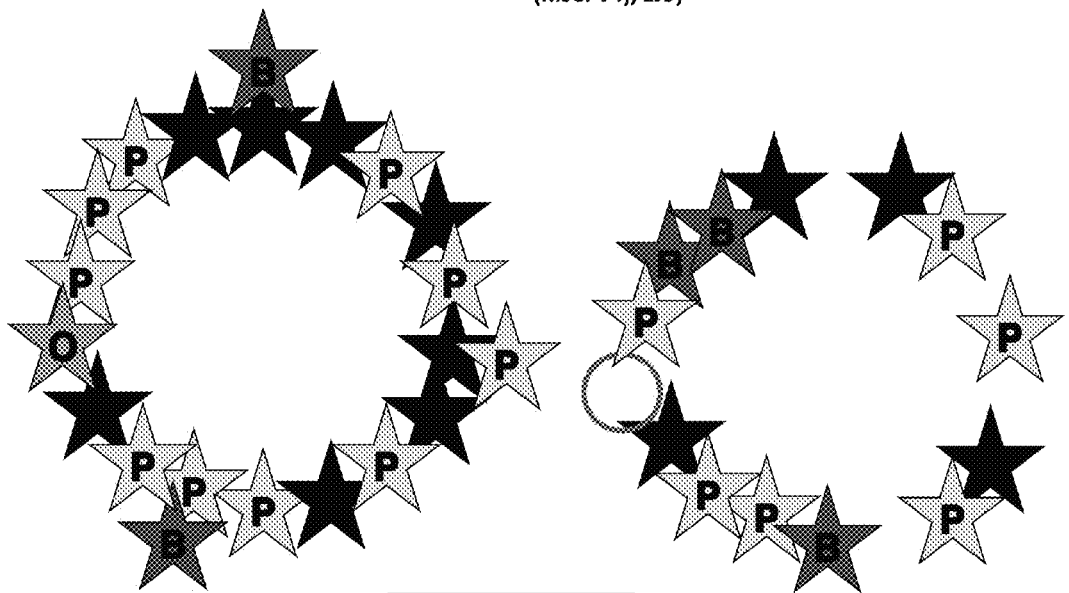
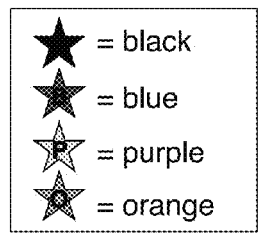
★ = black
★ = blue
☆ = purple
☆ = orange FIG. 3J
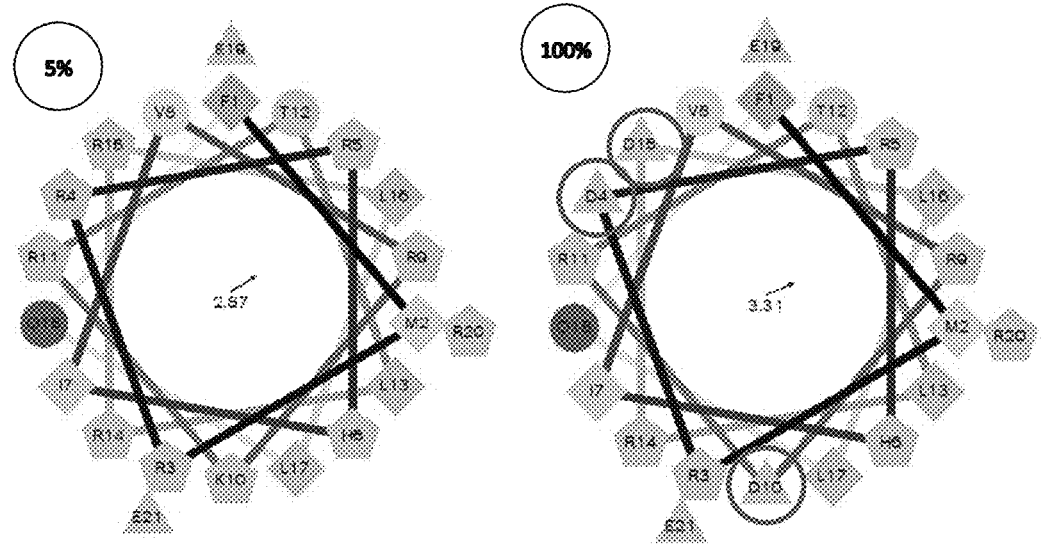
SEQ ID NO: 1 (Related to ENLS-1/EJ1)     SEQ ID NO: 12 (Related to ENLS-1 scramble/nlsCPv5/EJ10)
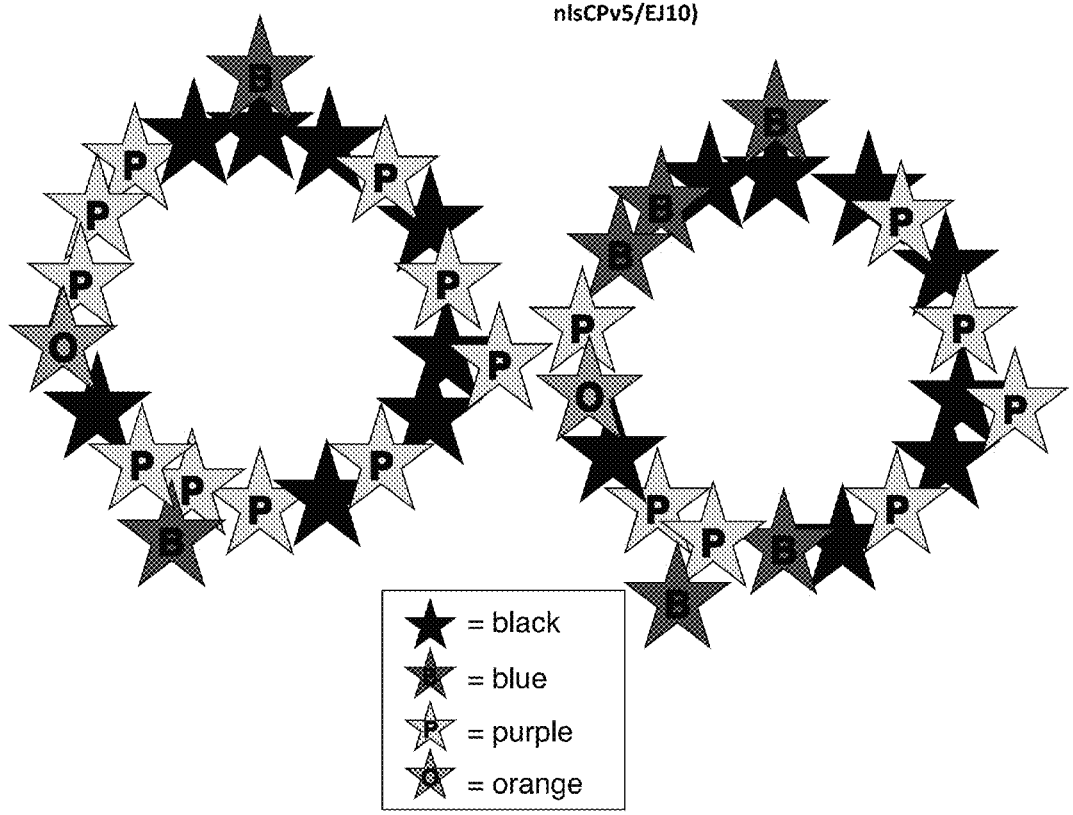

FIG. 14
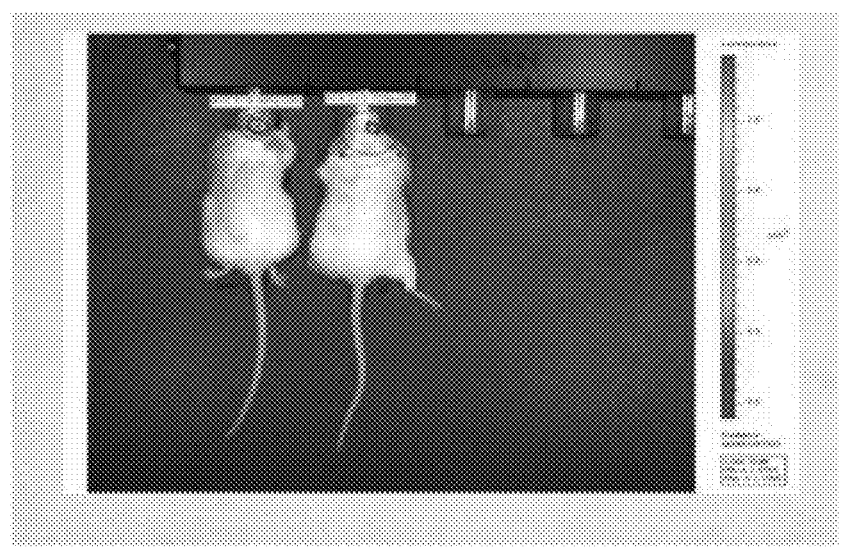
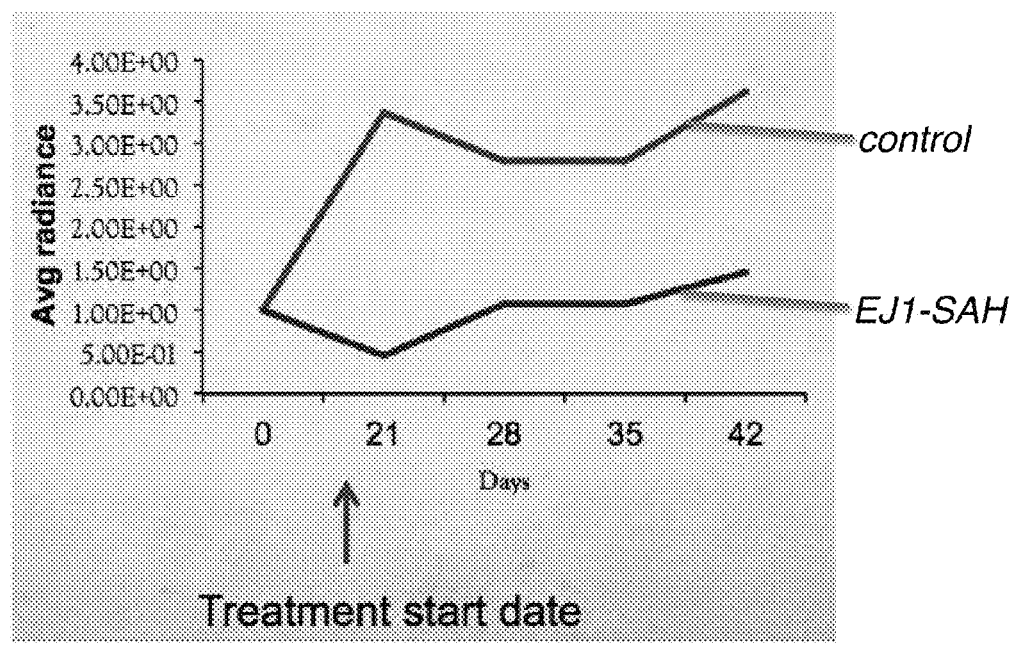

FIG. 15B
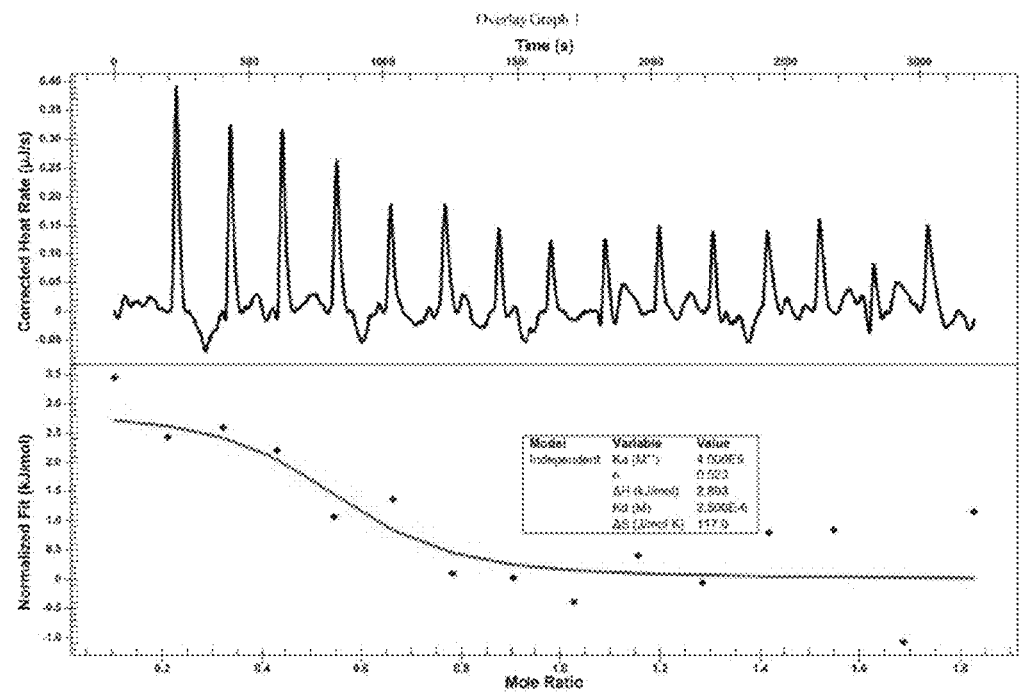
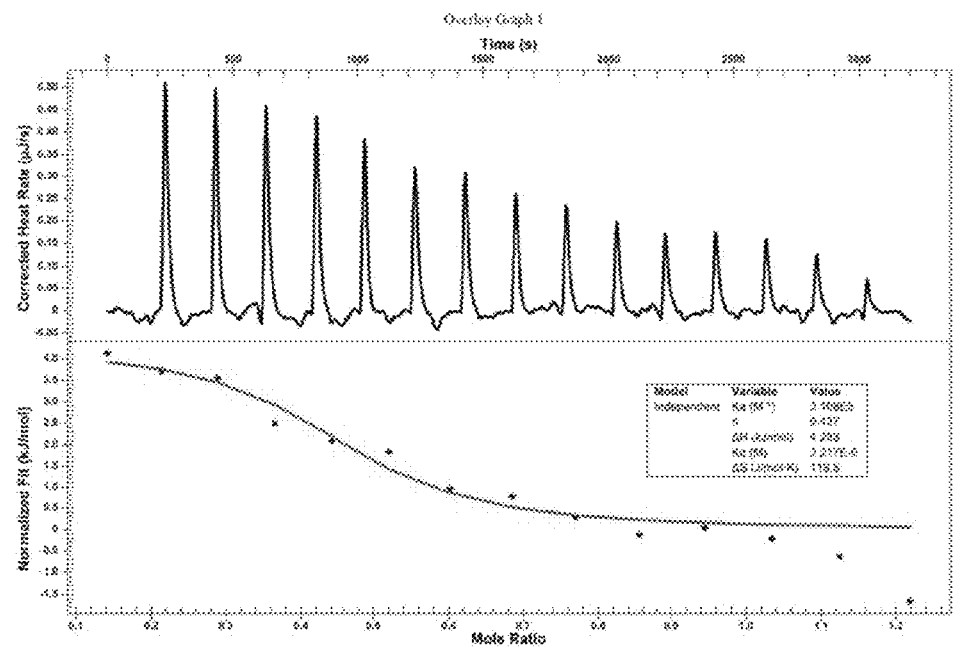

EGFR-BASED INHIBITOR PEPTIDES FOR COMBINATORIAL INACTIVATION OF ERBB1, ERBB2, AND ERBB3

CROSS REFERENCE

This application is non-provisional and claims benefit of U.S. Provisional Application No. 62/142,962 filed Apr. 3, 2015, U.S. Provisional Application No. 62/213,039 filed Sep. 1, 2015, and U.S. Provisional Application No. 62/214,098 filed Sep. 3, 2015, the specifications of which are incorporated herein in their entirety by reference. Further, this application is a continuation-in-part and claims benefit of U.S. patent application Ser. No. 13/879,143 filed May 30, 2013, which is a 371 application of PCT Application No. PCT/US11/55894 filed Oct. 12, 2011, which claims benefit of U.S. Provisional Application No. 61/392,249 filed Oct. 12, 2010, the specifications of which are incorporated herein in their entirety by reference.

REFERENCE TO SEQUENCE LISTING

Applicant asserts that the paper copy of the Sequence Listing is identical to the Sequence Listing in computer readable form found on the accompanying computer file. Applicant incorporates the contents of the sequence listing by reference in its entirety.

FIELD OF THE INVENTION

The present invention relates to inhibitor peptides for targeting and inhibiting ErbB1, ErbB2, and ErbB3 activity, including peptides for inhibiting growth of cancer cells and tumors.

BACKGROUND OF THE INVENTION

Inventors have surprisingly discovered inhibitor peptides that can be used to block nuclear translocation of EGFR. In some embodiments, the inhibitor peptides of the present invention can be used for combinatorial inactivation of EGFR (ErbB1), ErbB2, and ErbB3. The inhibitor peptides comprise an EGFR-based peptide, which is related to the EGFR juxtamembrane region. In some embodiments, the EGFR-based peptide comprises the tri-partite nuclear localization sequence of EGFR, which can act in a dominant-negative fashion to block nuclear translocation of EGFR. In some embodiments, the EGFR-based peptide is fused to (directly or indirectly) or synthesized in tandem with a cell penetrating component for cellular uptake (e.g., a protein transduction domain, e.g., PTD-4). One such inhibitor peptide, ENLS-1 (SEQ ID NO: 13, see FIG. 1) has been tested for its ability to block breast cancer cell growth and tumor growth in a transgenic mouse model, MMTV-pyMT. Other peptides also have been tested and found to have cell growth inhibitory properties (see FIG. 1).

SUMMARY OF THE INVENTION

The present invention features inhibitor peptides for combinatorial inactivation of ErbB1, ErbB2, and ErbB3. In some embodiments, the inhibitor peptide comprises an EGFR-based peptide and a cell penetrating component for enhancing penetration of the EGFR-based peptide into a cell, wherein the inhibitor peptide disrupts ErbB1, ErbB2, and ErbB3 activity.

In some embodiments, the EGFR-based peptide is at least 50% identical to at least 8 consecutive residues of SEQ ID NO: 1. In some embodiments, the EGFR-based peptide is at least 50% identical to at least 8 consecutive residues of SEQ ID NO: 1. In some embodiments, the EGFR-based peptide is at least 60% identical to at least 8 consecutive residues of SEQ ID NO: 1. In some embodiments, the EGFR-based peptide is at least 70% identical to at least 8 consecutive residues of SEQ ID NO: 1. In some embodiments, the EGFR-based peptide is at least 50% identical to at least 9 consecutive residues of SEQ ID NO: 1. In some embodiments, the EGFR-based peptide is at least 50% identical to at least 10 consecutive residues of SEQ ID NO: 1. In some embodiments, the EGFR-based peptide is at least 50% identical to at least 11 consecutive residues of SEQ ID NO: 1. In some embodiments, the EGFR-based peptide is at least 50% identical to at least 12 consecutive residues of SEQ ID NO: 1. In some embodiments, the EGFR-based peptide is at least 50% identical to at least 13 consecutive residues of SEQ ID NO: 1. In some embodiments, the EGFR-based peptide is at least 50% identical to at least 14 consecutive residues of SEQ ID NO: 1.

In some embodiments, the EGFR-based peptide comprises a sequence $X_1X_2X_3X_4X_5X_6X_7X_8X_9X_{10}X_{11}X_{12}X_{13}X_{14}X_{15}X_{16}X_{17}X_{18}X_{19}$, wherein at least two of $X_4$, $X_{11}$, and $X_{15}$ are basic amino acids, and wherein $X_{18}$ is a polar uncharged amino acid (e.g., glutamine, asparagine, etc.). In some embodiments, one or more of $X_1$-$X_{10}$ may comprise no amino acids (e.g., no amino acid may be in those positions, e.g., the first amino acid of the peptide may be at position $X_2$, $X_3$, $X_4$, $X_5$, $X_6$, $X_7$, $X_8$, $X_9$, $X_{10}$, or $X_{11}$). In some embodiments, $X_{19}$ may comprise no amino acid (e.g., no amino acid may be present in those positions, e.g., the last amino acid of the peptide may be $X_{18}$).

In some embodiments, the EGFR-based peptide comprises a sequence $X_1X_2X_3X_4X_5X_6X_7X_8X_9X_{10}X_{11}X_{12}X_{13}X_{14}X_{15}X_{16}X_{17}X_{18}X_{19}X_{20}X_{21}$, wherein at least two of $X_4$, $X_{11}$, and $X_{15}$ are basic amino acids, and wherein $X_{18}$ is a polar uncharged amino acid (e.g., glutamine, asparagine, etc.). In some embodiments, one or more of $X_1$-$X_{10}$ may be absent (e.g., no amino acid may be in those positions, e.g., the first amino acid of the peptide may be at position $X_2$, $X_3$, $X_4$, $X_5$, $X_6$, $X_7$, $X_8$, $X_9$, $X_{10}$, or $X_{11}$). In some embodiments, $X_{19}$-$X_{21}$ may be absent (e.g., no amino acid may be present in those positions, e.g., the last amino acid of the peptide may be $X_{18}$ or $X_{19}$ or $X_{20}$).

In some embodiments, $X_{18}$ is a basic amino acid. In some embodiments, $X_4$ is a polar uncharged amino acid (e.g., glutamine, asparagine, etc.). In some embodiments, $X_{11}$ is a polar uncharged amino acid (e.g., glutamine, asparagine, etc.). In some embodiments, $X_{15}$ is a polar uncharged amino acid (e.g., glutamine, asparagine, etc.). In some embodiments, three of $X_4$, $X_{11}$, $X_{15}$ are basic amino acids and $X_{18}$ is a polar uncharged amino acid (e.g., glutamine, asparagine, etc.). In some embodiments, two of $X_4$, $X_{11}$, $X_{15}$, and $X_{18}$ are basic amino acids and two thereof are polar uncharged amino acids (e.g., glutamine, asparagine, etc.). In some embodiments, $X_1X_2$ is FM or FR. In some embodiments, $X_1X_2X_3$ is FMR or FRM. In some embodiments, $X_{19}$ is an acidic acid. In some embodiments, $X_{18}X_{19}$ is QE or NE. In some embodiments, $X_{10}$ or $X_{12}$ is threonine.

In some embodiments, the EGFR-based peptide is from 8 to 30 amino acids in length. In some embodiments, the cell penetrating component is N-terminal to the first peptide. In some embodiments, the cell penetrating component comprises a protein transduction domain (PTD), e.g., PTD4.

In some embodiments, the inhibitor peptide has an $LD_{50}$ of 50 uM or less. In some embodiments, the inhibitor peptide has an $LD_{50}$ of 40 uM or less. In some embodiments, the inhibitor peptide has an $LD_{50}$ of 30 uM or less. In some embodiments, the inhibitor peptide has an $LD_{50}$ of 20 uM or less. In some embodiments, the inhibitor peptide has an $LD_{50}$ of 18 uM or less. In some embodiments, the inhibitor peptide has an $LD_{50}$ of 10 uM or less. In some embodiments, the inhibitor peptide has an $LD_{50}$ of 5 uM or less.

In some embodiments, the inhibitor peptide comprises an EGFR-based peptide is an alpha helix comprising at least a basic face. In some embodiments, the basic face comprises four amino acids, wherein at least two amino acids are basic amino acids and at least one is a polar uncharged amino acid (e.g., glutamine, asparagine, etc.). In some embodiments, the basic face comprises three basic amino acids and a polar uncharged amino acid (e.g., glutamine, asparagine, etc.). In some embodiments, the basic face comprises two basic amino acids and two polar uncharged amino acids (e.g., glutamine, asparagine, etc.). In some embodiments, the basic amino acid is arginine, lysine, or histidine. In some embodiments, the EGFR-based peptide further comprises one acidic face (e.g., the first acid face or the second acidic face), wherein the acidic face comprises an acidic amino acid (glutamic acid, aspartic acid). In some embodiments, the EGFR-based peptide further comprises two acidic faces (e.g., the first acid face and the second acidic face), wherein the acidic face comprises an acidic amino acid (glutamic acid, aspartic acid).

In some embodiments, the inhibitor peptide when administered in vivo is effective to inhibit tumor growth. In some embodiments, the polypeptide when administered in vivo is effective to reduce metastasis. In some embodiments, the inhibitor peptide is effective to activate apoptosis. In some embodiments, the inhibitor peptide is effective to activate necrosis. In some embodiments, the inhibitor peptide is effective to disrupt calcium signaling. In some embodiments, the inhibitor peptide is effective to increase ROS. In some embodiments, the peptide (in vivo) reduces growth of a tumor associated with aberrant ErBb activity. In some embodiments, the tumor is a breast tumor, brain tumor, ovarian tumor, prostate tumor, colon tumor, pancreatic tumor, or a lung tumor. In some embodiments, the peptide (in vivo) inhibits growth or proliferation of leukemia-associated cells.

In some embodiments, the inhibitor peptide further comprises a modification such as a modification effective for enhancing tumor cell killing (e.g., for increasing in vitro kill rate), for reducing tumor size, for inhibiting tumor growth, for lowering a $K_D$, etc., as compared to that of the inhibitor peptide without the modification. In some embodiments, the modification comprises substitution of two or more (e.g., four) amino acids to allow for hydrocarbon staples. In some embodiments, the inhibitor peptide comprises two amino acid substitutions, the substitution being selected from: (R)-2-{[(9H-fluoren-9-yl)methoxy]carbonylamino}-2-methyldec-9-enoic acid (also known as R8) or (S)-2-{[(99H-fluoren-9-yl)methoxy]carbonylamino}-2-methyl-hept-6-enoic acid (also known as S5). In some embodiments, the inhibitor peptide comprises one of R8 and one of S5. In some embodiments, the amino acids that are substituted are positioned on the same face of the alpha helix of the inhibitor peptide.

In some embodiments, in vitro the peptide binds to ENLS-1 with a $K_d$ of 15 uM or less. In some embodiments, in vitro the peptide binds to ENLS-1 with a $K_d$ of 10 uM or less. In some embodiments, in vitro the peptide binds to SAHEJ1 with a $K_d$ of 5 uM or less. In some embodiments, in vitro the peptide binds to SAHEJ1 with a $K_d$ of 3 uM or less.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

FIG. 1 shows data from PCT/US2011/055894. Inhibitor peptides were evaluated on their ability to inhibit growth of triple-negative breast cancer cells MDA-MB-468 (20 uM peptide treatment). Survival rates after 3 days are shown. Note PTD4 refers to the PTD4 domain (YARAAARQARA (SEQ ID NO: 110)). SEQ ID NO: 13 is YARAAAR-QARAFMRRRHIVRKRTLRRLLQERE (PTD4+FMR-RRHIVRKRTLRRLLQERE (SEQ ID NO: 1)). SEQ ID NO: 14 is YARAAARQARAFRMHRIRVRTKLRLRLRQERE (PTD4+FRMHRIRVRTKLRLRLRQERE (SEQ ID NO: 2)). SEQ ID NO: 15 is YARAAARQARAFM-RQRHIVRQRTLRQLLQERE (PTD4+FM-RQRHIVRQRTLRQLLQERE (SEQ ID NO: 3)). SEQ ID NO: 16 is YARAAARQARAIVRKRTLRRLLQERE (PTD4+IVRKRTLRRLLQERE (SEQ ID NO: 4)). SEQ ID NO: 17 is YARAAARQARAIVRTKLRLRLRQERE (PTD4+IVRTKLRLRLRQERE (SEQ ID NO: 5)). SEQ ID NO: 18 is YARAAARQARARTLRRLLQERE (PTD4+RTLRRLLQERE (SEQ ID NO: 6)). SEQ ID NO: 19 is YARAAARQARAFMRRRHIVRKRTL (PTD4+FMR-RRHIVRKRTL (SEQ ID NO: 7)). SEQ ID NO: 20 is YARAAARQARARRRHIVRKRTLRR (PTD4+RRRHIVRKRTLRR (SEQ ID NO: 8)). SEQ ID NO: 21 is YARAAARQARAFRMHRIRVRTKLR (PTD4+FRM-HRIRVRTKLR (SEQ ID NO: 9)). SEQ ID NO: 22 is YARAAARQARALLQERELVEPLT (PTD4+LLQERELVEPLT (SEQ ID NO: 10)). SEQ ID NO: 23 is YARAAARQARARDRHIVRDRTLRD (PTD4+RDRHIVRDRTLRD (SEQ ID NO: 11)). SEQ ID NO: 24 is YARAAARQARAFMRDRHIVRDRTLRDLLQERE (PTD4+FMRDRHIVRDRTLRDLLQERE (SEQ ID NO: 12)). SEQ ID NO: 25 is YARAAARQARAAAQEREAAE-PLT (PTD+AAQEREAAEPLT). SEQ ID NO: 26 is YARAAARQARAFMAAAHIVAAATLAALLQERE (PTD+FMAAAHIVAAATLAALLQERE).

FIG. 2A shows a predicted structure of the EGFR-based peptides SEQ ID NO: 1 (top) and SEQ ID NO: 2 (bottom). The percentages shown circled refer to the survival rate of cells treated with the related peptide (the EGFR-based peptide in combination with PTD4) shown in FIG. 1.

FIG. 2B shows a generalized color categorized structure of the EGFR-based peptides SEQ ID NO: 1 (top) and SEQ ID NO: 2 (bottom) based on properties of amino acids. Basic amino acids (arginine, lysine, or histidine) residues are purple; acidic amino acids (aspartic acid, glutamic acid) are blue; Glutamine is orange; All other amino acids are black.

FIG. 3A-3J show the predicted structure (top picture) and generalized structure (bottom picture) of EGFR-based peptide SEQ ID NO: 1 (left) compared with other EGFR-based peptides selected from Table 1. The percentages shown circled refer to the survival rate of cells treated with the related peptide (the EGFR-based peptide in combination with PTD4) shown in FIG. 1. Red circles (if any) refer to particular amino acid differences between SEQ ID NO: 1 and that peptide shown. For the generalized structures (bottom pictures), basic amino acids (arginine, lysine, or histidine) residues are purple; acidic amino acids (aspartic acid, glutamic acid) are blue; Glutamine is orange; All other amino acids are black.

FIG. 13A shows the effect of stapled EJ1 compared to a control peptide on two different patient-derived glioma lines (BT145 and BT147). Stapled EJ1 led to decrease in viability, compared to no effect on cell viability in the control peptide. FIG. 13B shows the effect of stapled EJ1 compared to a control peptide on four patient-derived glioma lines (GB16, GB7, GB42, and BT147). Stapled EJ1 led to decrease in viability after 24 hr treatment, compared to no effect on cell viability in the control peptide.

FIG. 14 shows an in vivo study treating mice with daily subcutaneous injections of SAH-EJ1 (Stapled version of EJ1) (SEQ ID NO: 111) at 10 mg/kg. The growth of the tumor is reduced in the mouse treated with SAH-EJ1 as compared to the control mouse.

FIG. 15A and FIG. 15B show that stapling may lower the $K_d$ of the inhibitor peptides. FIG. 15A shows ITC experiments using ENLS1 at 100 uM. The target was Ecyl EGFR peptide at 500 uM. The $K_d$ for the experiment was 10 uM. Note that in the experiment, an n of 0.532 suggests that there may be two ENLS1 peptides binding to the target. FIG. 15B shows ITC experiments using SAH-EJ1 at 100 uM (top) and 150 uM (bottom). The target was Ecyl EGFR peptide at 500 uM. The $K_d$ for the top experiment was 2.5 uM, the $K_d$ for the bottom experiment was 3.2 uM (averaging about 2.85 uM). Note that in both experiments, an n of 0.523 (top) and 0.437 (bottom) suggests that there may be two SAH-EJ1 peptides binding to the target.

DETAILED DESCRIPTION OF THE INVENTION

Figure 4:
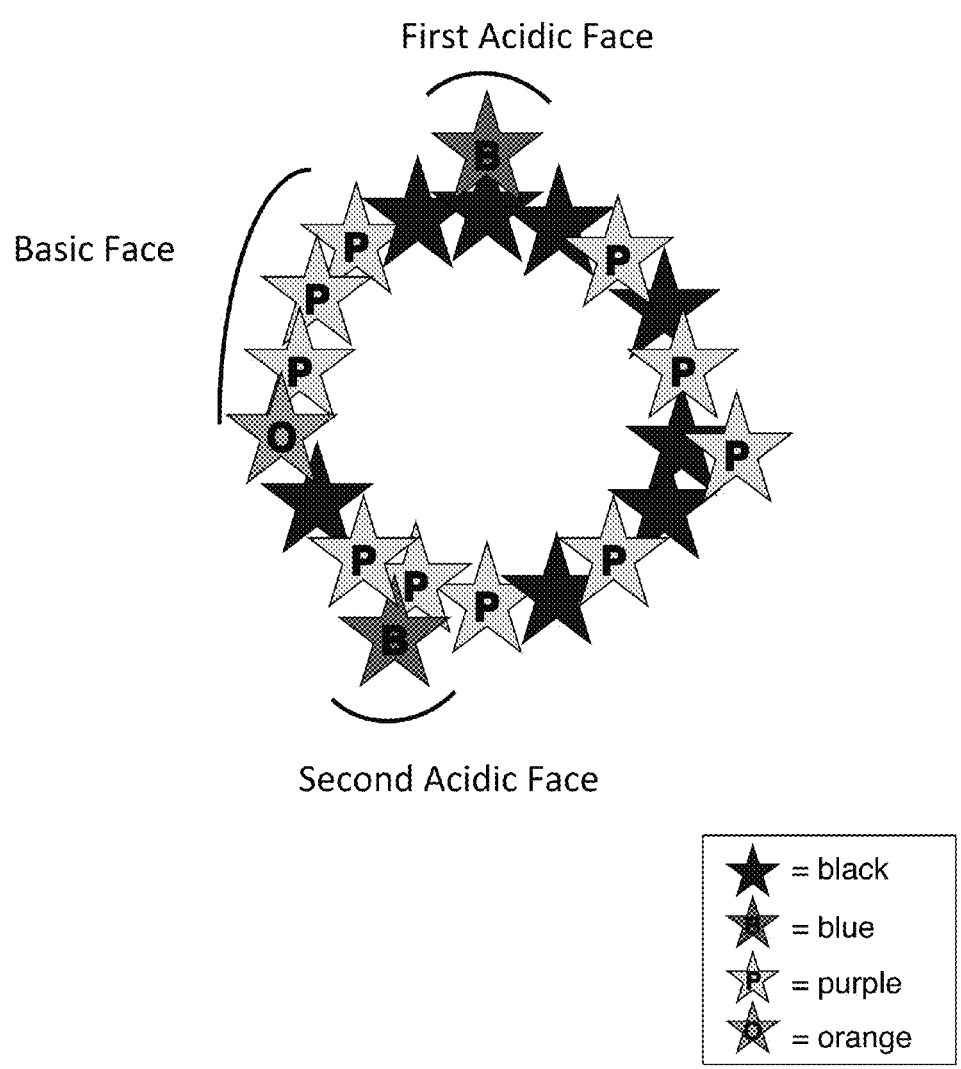
FIG. 4 shows a schematic representation of the basic face and acidic face of the EGFR-based peptides of the present invention. The example shown is a generalized structure of the EGFR-based peptides SEQ ID NO: 1. Basic amino acids (arginine, lysine, or histidine) residues are purple; acidic amino acids (aspartic acid, glutamic acid) are blue; Glutamine is orange; All other amino acids are black.

The present invention features inhibitor peptides for inhibiting ErbB1, ErbB2, ErbB3, a combination thereof, or all three thereof. For example, in some embodiments, the inhibitor peptides are effective for combinatorial inactivation of ErbB1, ErbB2, and ErbB3.

EGFR-Based Peptides

The inhibitor peptides comprise an EGFR-based peptide and a cell penetrating component. The EGFR-based peptide is related to the EGFR juxtamembrane region. In some embodiments, the EGFR-based peptide is based on the following juxtamembrane sequence from EGFR: LLLWAL-GIGLFM<u>RRR</u>HIV<u>RKR</u>TL<u>RR</u>LLQERELVEPLTPS (SEQ ID NO: 27) (the tri-partite sequence is underlined).

Table 1 below lists several non-limiting examples of EGFR-based peptides. Note relative position 4, relative position 11, relative position 15, relative position 18, relative position 19, and relative position 21.

TABLE 1

| SEQ ID NO:/ Related Peptide | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| SEQ ID NO: 1 ENLS-1/EJ1 | F | M | R | R | R | H | I | V | R | K | R | T | L | R | R | L | L | Q | E | R | E |
| SEQ ID NO: 2 nlsCPv1 | F | R | M | H | R | I | R | V | R | T | K | L | R | L | R | L | R | Q | E | R | E |
| SEQ ID NO: 3 nlsCPv6/EJ11 | F | M | R | Q | R | H | I | V | R | Q | R | T | L | R | Q | L | L | Q | E | R | E |
| SEQ ID NO: 4 ENLS-3/EJ3 | — | — | — | — | — | — | I | V | R | K | R | T | L | R | R | L | L | Q | E | R | E |
| SEQ ID NO: 5 cENLS-3 | — | — | — | — | — | — | I | V | R | T | K | L | R | L | R | L | R | Q | E | R | E |
| SEQ ID NO: 6 ENLS-5/EJ5 | — | — | — | — | — | — | — | — | — | — | R | T | L | R | R | L | L | Q | E | R | E |
| SEQ ID NO: 7 ENLS-2 | F | M | R | R | R | H | I | V | R | K | R | T | — | — | — | — | — | — | — | — | — |
| SEQ ID NO: 8 ENLS-4 | — | — | R | R | R | H | I | V | R | K | R | T | L | R | R | — | — | — | — | — | — |
| SEQ ID NO: 9 cENLS-2 | F | R | M | H | R | I | R | V | R | T | K | L | R | — | — | — | — | — | — | — | — |
| SEQ ID NO: 10 EBL-1 | — | — | — | — | — | — | — | — | — | — | — | — | — | — | — | L | L | Q | E | R | E |
| SEQ ID NO: 11 nlsCPv4 | — | — | R | D | R | H | I | V | R | D | R | T | L | R | D | — | — | — | — | — | — |
| SEQ ID NO: 12 nlsCPv5 | F | M | R | D | R | H | I | V | R | D | R | T | L | R | D | L | L | Q | E | R | E |

Referring to FIG. 2 and FIG. 3, the EGFR-based peptides are arranged in an alpha helix. For reference, the predicted alpha helix structures shown in FIG. 2 and FIG. 3 are obtained from the Emboss Pepwheel feature of the Transporter Classification database (www.tcdb.org/progs/?tool=pepwheel). FIG. 2A shows the predicted alpha helix structure of SEQ ID NO: 1 and SEQ ID NO: 2 (see Table 1 for sequences). FIG. 2B shows a similar structure but wherein the amino acids have been color categorized for visualization purposes. The basic amino acids lysine, arginine, and histidine were colored purple. Glutamine was colored orange. The acidic amino acids glutamic acid and aspartic acid were colored blue. All other amino acids were colored black.

FIG. 3A-FIG. 3J show the predicted alpha helix structures and corresponding color categorized structures of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12 from Table 1.

Also shown in FIG. 2 and FIG. 3 are the approximate survival rate of cells treated with the respective related peptide (e.g., the peptide comprising the EGFR-based peptide and PTD4), which can be found in FIG. 1. For example, FIG. 3A shows the predicted structures of SEQ ID NO: 1 and SEQ ID NO: 3. For SEQ ID NO: 1, the survival rate of cells treated with its related peptide (ENLS-1) is 5%. For SEQ ID NO: 3, the survival rate of cells treated with its related peptide (nlsCPv6) is 35%. FIG. 3 compares the general structure of SEQ ID NO: 1, whose related peptide ENLS-1 had a high kill rate (only 5% of cells survived after 3 days) with other peptides. Some peptides, e.g., nlsCPv4, nlsCPv5, had almost no inhibitor effect as nearly all cells survived after three days of treatment. Without wishing to limit the present invention to any theory or mechanism, it is believed that the predicted structures of these peptides with the structures of more effective peptides may be important in determining which amino acids or regions of the EGFR-based peptide is important for inhibitory properties.

As shown in FIG. 4, the general structure of the EGFR-based peptide shows a basic face, comprising several basic amino acids or glutamine residues. The structure also shows a first acidic face comprising an acidic amino acid counter-clockwise to the basic face. The structure also shows a second acidic face comprising an acidic amino acid clockwise to the basic face.

In some embodiments, the EGFR-based peptide comprises at least one basic face, wherein the basic face comprises a basic amino, a glutamine (or asparagine or other appropriate substitution for glutamine), and at least one of either another basic amino acid or another glutamine (or asparagine or other appropriate substitution for glutamine). For example, in some embodiments, the basic face comprises two basic amino acids and a glutamine. In some embodiments, the basic face comprises three basic amino acids and a glutamine. In some embodiments, the basic face comprises four basic amino acids and a glutamine. In some embodiments, the basic face comprises one basic amino acid and two glutamines. In some embodiments, the basic face comprises one basic amino acid and three glutamines. In some embodiments, the basic face comprises two basic amino acids and an asparagine. In some embodiments, the basic face comprises three basic amino acids and an asparagine. In some embodiments, the basic face comprises four basic amino acids and an asparagine. In some embodiments, the basic face comprises one basic amino acid and two asparagines. In some embodiments, the basic face comprises one basic amino acid and three asparagines.

As previously discussed, in some embodiments, the glutamine is substituted with an asparagine. In some embodiments, the glutamine is substituted with a polar uncharged amino acid. In some embodiments, the polar uncharged amino acid comprises methionine. In some embodiments, the polar uncharged amino acid comprises serine. In some embodiments, the polar uncharged amino acid comprises threonine. In some embodiments, the polar uncharged amino acid comprises asparagine. In some embodiments, the polar uncharged amino acid comprises cysteine.

In some embodiments, the basic amino acid is arginine. In some embodiments, the basic amino acid is lysine. In some embodiments, the basic amino acid is histidine.

In some embodiments, the EGFR-based peptide further comprises a first acidic face. In some embodiments, the EGFR-based peptide further comprises a second acidic face. In some embodiments, the EGFR-based peptide further comprises both a first and second acidic face. The first acidic face or second acidic face comprises an acidic amino acid. In some embodiments, the acidic amino acid is glutamic acid. In some embodiments, the acidic amino acid is aspartic acid. In some embodiments, the acidic face is counterclockwise to the basic face. In some embodiments, the acidic face is clockwise to the basic face.

In some embodiments, the EGFR-based peptide is 8 amino acids in length. In some embodiments, the EGFR-based peptide is 9 amino acids in length. In some embodiments, the EGFR-based peptide is 10 amino acids in length. In some embodiments, the EGFR-based peptide is 11 amino acids in length. In some embodiments, the EGFR-based peptide is 12 amino acids in length. In some embodiments, the EGFR-based peptide is 13 amino acids in length. In some embodiments, the EGFR-based peptide is 14 amino acids in length. In some embodiments, the EGFR-based peptide is 15 amino acids in length. In some embodiments, the EGFR-based peptide is 16 amino acids in length. In some embodiments, the EGFR-based peptide is 17 amino acids in length. In some embodiments, the EGFR-based peptide is 18 amino acids in length. In some embodiments, the EGFR-based peptide is 19 amino acids in length. In some embodiments, the EGFR-based peptide is 20 amino acids in length. In some embodiments, the EGFR-based peptide is 21 amino acids in length. In some embodiments, the EGFR-based peptide is 22 amino acids in length. In some embodiments, the EGFR-based peptide is 23 amino acids in length. In some embodiments, the EGFR-based peptide is 24 amino acids in length. In some embodiments, the EGFR-based peptide is 25 amino acids in length. In some embodiments, the EGFR-based peptide is 26 amino acids in length. In some embodiments, the EGFR-based peptide is 27 amino acids in length. In some embodiments, the EGFR-based peptide is 28 amino acids in length. In some embodiments, the EGFR-based peptide is 29 amino acids in length. In some embodiments, the EGFR-based peptide is 30 amino acids in length. In some embodiments, the EGFR-based peptide is more than 30 amino acids in length.

In some embodiments, the EGFR-based peptide comprises a sequence $X_1X_2X_3X_4X_5X_6X_7X_8X_9X_{10}X_{11}X_{12}X_{13}X_{14}X_{15}X_{16}X_{17}X_{18}X_{19}$, wherein $X_1$-$X_{10}$ may be absent (e.g., no amino acid may be in those positions, e.g., the first amino acid of the peptide may be at position $X_{11}$) and/or $X_{19}$ may be absent (e.g., no amino acid may be present in those positions, e.g., the last amino acid of the peptide may be $X_{18}$). In some embodiments, the EGFR-based peptide comprises a sequence $X_1X_2X_3X_4X_5X_6X_7X_8X_9X_{10}X_{11}X_{12}X_{13}X_{14}X_{15}X_{16}X_{17}X_{18}X_{19}X_{20}X_{21}$, wherein $X_1$-$X_{10}$ may be absent (e.g., no amino acid may be in those positions, e.g., the first amino acid of the peptide may be at position $X_{11}$) and/or $X_{19}$-$X_{21}$ may be absent (e.g., no amino acid may be present in those positions, e.g., the last amino acid of the peptide may be $X_{18}$ or $X_{19}$ or $X_{20}$).

In some embodiments, the EGFR-based peptide is at least 50% identical to at least 8 consecutive residues of SEQ ID NO: 1. In some embodiments, the EGFR-based peptide is at least 50% identical to at least 8 consecutive residues of SEQ ID NO: 1. In some embodiments, the EGFR-based peptide is at least 60% identical to at least 8 consecutive residues of SEQ ID NO: 1. In some embodiments, the EGFR-based peptide is at least 70% identical to at least 8 consecutive residues of SEQ ID NO: 1. In some embodiments, the EGFR-based peptide is at least 50% identical to at least 9 consecutive residues of SEQ ID NO: 1. In some embodiments, the EGFR-based peptide is at least 50% identical to at least 10 consecutive residues of SEQ ID NO: 1. In some embodiments, the EGFR-based peptide is at least 50% identical to at least 11 consecutive residues of SEQ ID NO: 1. In some embodiments, the EGFR-based peptide is at least 50% identical to at least 12 consecutive residues of SEQ ID NO: 1. In some embodiments, the EGFR-based peptide is at least 50% identical to at least 13 consecutive residues of SEQ ID NO: 1. In some embodiments, the EGFR-based peptide is at least 50% identical to at least 14 consecutive residues of SEQ ID NO: 1.

In some embodiments, $X_4$, $X_{11}$, and $X_{15}$ are basic amino acids. In some embodiments, $X_{18}$ is glutamine. In some embodiments, $X_{18}$ is a polar uncharged amino acid (e.g., glutamine, asparagine, methionine, serine, threonine, cysteine). In some embodiments, $X_{18}$ is a basic amino acid. In some embodiments, $X_4$ is glutamine. In some embodiments, $X_{11}$ is glutamine. In some embodiments, $X_{15}$ is glutamine. In some embodiments, three of $X_4$, $X_{11}$, $X_{15}$ are basic amino acids and $X_{18}$ is glutamine. In some embodiments, two of $X_4$, $X_{11}$, $X_{15}$ are basic amino acids and $X_{18}$ is glutamine. In some embodiments, three of $X_4$, $X_{11}$, $X_{15}$, and $X_{18}$ are basic amino acids and one thereof is glutamine. In some embodiments, two of $X_4$, $X_{11}$, $X_{15}$, and $X_{18}$ are basic amino acids and two thereof are glutamines.

Table 2 below shows non-limiting examples of combinations of residues for positions $X_4$, $X_{11}$, $X_{15}$, and $X_{18}$. The present invention is not limited to the examples shown in Table 2. For example, in some embodiments, the EGFR-based peptide does not have $X_4$.

TABLE 2

| | Amino Acids at Particular Relative Positions | | | |
|---|---|---|---|---|
| Example | 4 | 11 | 15 | 18 |
| 1 | R | R | R | Q |
| 2 | R | R | H | Q |
| 3 | R | R | K | Q |
| 4 | R | K | R | Q |
| 5 | R | H | R | Q |
| 6 | K | R | R | Q |
| 7 | H | R | R | Q |
| 8 | H | H | H | Q |
| 9 | H | H | R | Q |
| 10 | H | H | K | Q |
| 11 | H | R | H | Q |
| 12 | H | K | H | Q |
| 13 | R | H | H | Q |
| 14 | K | H | H | Q |
| 15 | K | K | K | Q |
| 16 | K | K | R | Q |
| 17 | K | K | H | Q |
| 18 | R | K | K | Q |
| 19 | H | K | K | Q |
| 20 | K | R | K | Q |
| 21 | K | H | K | Q |
| 22 | R | K | H | Q |
| 23 | R | H | K | Q |
| 24 | H | K | R | Q |
| 25 | K | H | R | Q |
| 26 | H | R | K | Q |
| 27 | K | R | H | Q |
| 28 | Q | R | R | Q |
| 29 | Q | R | H | Q |
| 30 | Q | R | K | Q |
| 31 | Q | H | H | Q |
| 32 | Q | H | K | Q |
| 33 | Q | H | R | Q |

TABLE 2-continued

| | Amino Acids at Particular Relative Positions | | | |
|---|---|---|---|---|
| Example | 4 | 11 | 15 | 18 |
| 34 | Q | K | R | Q |
| 35 | Q | K | H | Q |
| 36 | Q | K | K | Q |
| 37 | R | Q | R | Q |
| 38 | R | Q | H | Q |
| 39 | R | Q | K | Q |
| 40 | H | Q | H | Q |
| 41 | H | Q | R | Q |
| 42 | H | Q | K | Q |
| 43 | K | Q | K | Q |
| 44 | K | Q | H | Q |
| 45 | K | Q | R | Q |
| 46 | R | R | Q | Q |
| 47 | R | H | Q | Q |
| 48 | R | K | Q | Q |
| 49 | K | R | Q | Q |
| 50 | K | K | Q | Q |
| 51 | K | H | Q | Q |
| 52 | H | R | Q | Q |
| 53 | H | K | Q | Q |
| 54 | H | H | Q | Q |
| 55 | Q | R | Q | Q |
| 56 | Q | H | Q | Q |
| 57 | Q | K | Q | Q |

In some embodiments, $X_1$ is phenylalanine. In some embodiments, $X_2$ is methionine or arginine. In some embodiments, $X_3$ is methionine or arginine. In some embodiments, $X_1X_2$ is FM or FR. In some embodiments, $X_1X_2X_3$ is FMR or FRM.

In some embodiments, $X_{19}$ is an acidic acid (e.g., glutamic acid, aspartic acid). In some embodiments, $X_{21}$ is an acidic acid (e.g., glutamic acid, aspartic acid).

In some embodiments, $X_{18}X_{19}$ is QE. In some embodiments, $X_{18}X_{19}$ is QD.

In some embodiments, $X_2$ is a basic amino acid (R, K, H). In some embodiments, $X_3$ is a basic amino acid (R, K, H). In some embodiments, $X_5$ is a basic amino acid (R, K, H). In some embodiments, $X_6$ is a basic amino acid (R, K, H). In some embodiments, $X_7$ is a basic amino acid (R, K, H). In some embodiments, $X_8$ is a basic amino acid (R, K, H). In some embodiments, $X_9$ is a basic amino acid (R, K, H). In some embodiments, $X_{10}$ is a basic amino acid (R, K, H). In some embodiments, $X_{13}$ is a basic amino acid (R, K, H). In some embodiments, $X_{14}$ is a basic amino acid (R, K, H). In some embodiments, $X_{17}$ is a basic amino acid (R, K, H). In some embodiments, $X_{20}$ is a basic amino acid (R, K, H). In some embodiments, $X_{10}$ is glutamine.

In some embodiments, $X_6$ is a non-polar amino acid. In some embodiments, $X_6$ is a non-polar amino acid, e.g., I. In some embodiments, $X_6$ is a non-polar amino acid, e.g., V. In some embodiments, $X_6$ is a non-polar amino acid, e.g., L. In some embodiments, $X_6$ is a non-polar amino acid, e.g., M, F, W, or Y. In some embodiments, $X_7$ is a non-polar amino acid. In some embodiments, $X_7$ is a non-polar amino acid, e.g., I. In some embodiments, $X_7$ is a non-polar amino acid, e.g., V. In some embodiments, $X_7$ is a non-polar amino acid, e.g., L. In some embodiments, $X_7$ is a non-polar amino acid, e.g., M, F, W, or Y. In some embodiments, $X_8$ is a non-polar amino acid. In some embodiments, $X_8$ is a non-polar amino acid, e.g., I. In some embodiments, $X_8$ is a non-polar amino acid, e.g., V. In some embodiments, $X_8$ is a non-polar amino acid, e.g., L. In some embodiments, $X_8$ is a non-polar amino acid, e.g., M, F, W, or Y. In some embodiments, $X_{13}$ is a non-polar amino acid. In some embodiments, $X_{13}$ is a non-polar amino acid, e.g., I. In some embodiments, $X_{13}$ is a non-polar amino acid, e.g., V. In some embodiments, $X_{13}$ is a non-polar amino acid, e.g., L. In some embodiments, $X_{13}$ is a non-polar amino acid, e.g., M, F, W, or Y. In some embodiments, $X_{16}$ is a non-polar amino acid. In some embodiments, $X_{16}$ is a non-polar amino acid, e.g., I. In some embodiments, $X_{16}$ is a non-polar amino acid, e.g., V. In some embodiments, $X_{16}$ is a non-polar amino acid, e.g., L. In some embodiments, $X_{16}$ is a non-polar amino acid, e.g., M, F, W, or Y. In some embodiments, $X_{17}$ is a non-polar amino acid. In some embodiments, $X_{17}$ is a non-polar amino acid, e.g., I. In some embodiments, $X_{17}$ is a non-polar amino acid, e.g., V. In some embodiments, $X_{17}$ is a non-polar amino acid, e.g., L. In some embodiments, $X_{17}$ is a non-polar amino acid, e.g., M, F, W, or Y.

In some embodiments, $X_{10}$ is a threonine. In some embodiments, $X_{12}$ is a threonine.

In some embodiments, the EGFR-based peptide comprises at least a sequence R/K/H-X-X-X-R/K/H-X-X-Q/N, wherein R/K/H refers to one of R, K, or H, and X refers to any other appropriate amino acid. In some embodiments, the EGFR-based peptide comprises at least a sequence R/K/H-X-X-X-R/K/H-X-X-Q/N-D/E, wherein R/K/H refers to one of R, K, or H, X refers to any other appropriate amino acid, and D/E refers to either D or E. In some embodiments, the EGFR-based peptide comprises at least a sequence R/K/H-X-X-X-R/K/H-X-X-Q/N-D/E-X-D/E, wherein R/K/H refers to one of R, K, or H, X refers to any other appropriate amino acid, and D/E refers to either D or E. In some embodiments, the EGFR-based peptide comprises at least a sequence R/K/H-X-X-X-R/K/H-X-X-Q/N-D/E-R/K/H-D/E, wherein R/K/H refers to one of R, K, or H, X refers to any other appropriate amino acid, and D/E refers to either D or E. In some embodiments, the EGFR-based peptide comprises at least a sequence R/K/H-X-X-Q/N-D/E, wherein R/K/H refers to one of R, K, or H, X refers to any other appropriate amino acid, and D/E refers to either D or E. In some embodiments, the EGFR-based peptide comprises at least a sequence R/K/H-X-X-Q/N-D/E-X-D/E, wherein R/K/H refers to one of R, K, or H, X refers to any other appropriate amino acid, and D/E refers to either D or E.

Table 3 below shows non-limiting examples of EGFR-based peptides.

TABLE 3

| SEQ ID NO: | Residue/Position Number | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| 1 | F | M | R | R | R | H | I | V | R | K | R | T | L | R | R | L | L | Q | E | R | E |
| 28 | F | M | R | R | R | H | I | L | R | Q | R | T | V | R | R | L | L | Q | E | R | E |
| 29 | F | M | R | R | H | H | V | L | R | K | R | T | L | K | R | L | L | Q | E | R | E |
| 30 | F | M | K | R | R | H | I | V | H | K | H | T | L | H | R | I | L | Q | D | R | E |
| 31 | F | M | K | R | R | H | I | V | H | K | H | T | L | R | R | L | L | Q | E | R | E |
| 32 | F | M | K | R | Q | H | I | V | H | K | H | T | L | H | R | I | L | Q | E | R | E |
| 33 | F | M | H | R | R | H | L | V | R | R | R | T | L | R | H | L | L | Q | E | R | E |
| 34 | F | M | H | R | K | I | V | H | K | K | R | T | L | R | H | L | L | Q | E | R | E |

TABLE 3-continued

| SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| 35 | F | M | H | R | R | H | L | V | H | R | R | T | K | R | H | L | L | Q | E | R | E |
| 36 | F | M | R | R | R | H | I | V | R | K | K | T | L | R | R | L | L | Q | D | R | D |
| 37 | F | M | R | R | R | R | I | V | R | K | K | T | L | R | R | R | L | Q | E | R | E |
| 38 | F | M | R | R | Q | H | I | V | R | Q | K | T | L | R | R | Q | L | Q | E | R | E |
| 39 | F | M | R | R | R | H | I | V | R | K | R | T | L | R | K | L | L | Q | E | R | E |
| 40 | F | M | R | R | K | V | H | V | R | K | R | T | L | R | K | L | L | Q | E | R | E |
| 41 | F | M | R | R | Q | H | L | V | Q | K | R | T | L | R | K | L | L | Q | E | R | E |
| 42 | F | M | R | K | R | H | I | V | R | K | R | T | L | R | R | L | L | Q | D | R | E |
| 43 | F | M | R | K | R | R | I | V | R | R | R | T | L | K | R | L | L | Q | E | R | E |
| 44 | F | M | R | K | R | H | I | V | K | K | R | T | K | H | R | L | L | Q | E | R | D |
| 45 | F | M | R | H | R | H | I | V | R | K | R | T | L | R | R | L | L | Q | E | R | E |
| 46 | F | M | R | H | R | H | I | V | R | K | R | T | L | R | R | L | K | Q | E | R | E |
| 47 | F | M | R | H | R | V | I | V | H | H | R | T | L | R | R | K | L | Q | E | R | E |
| 48 | F | M | R | R | R | H | I | V | R | T | H | T | L | R | K | K | L | Q | E | R | E |
| 49 | F | M | R | R | R | Q | I | V | R | Q | H | T | L | R | K | K | L | Q | E | R | E |
| 50 | F | M | R | R | R | H | I | L | L | T | H | T | L | R | K | K | L | Q | E | R | E |
| 51 | F | M | R | R | R | H | I | V | R | K | K | T | L | R | H | L | L | Q | E | R | E |
| 52 | F | M | R | R | R | K | I | V | R | K | K | T | L | R | H | L | L | Q | D | R | E |
| 53 | F | M | R | R | R | H | L | V | L | K | T | L | R | H | L | L | Q | E | R | E |
| 54 | F | M | R | H | R | H | I | V | R | K | R | T | L | R | K | L | L | Q | E | R | E |
| 55 | F | M | R | H | R | H | I | V | R | K | R | R | R | K | L | L | Q | E | R | E |
| 56 | F | M | R | H | R | H | R | V | R | K | R | T | R | R | K | L | L | Q | E | R | E |
| 57 | F | M | R | K | R | H | I | V | R | K | R | T | L | R | H | L | L | Q | E | R | E |
| 58 | F | M | R | K | R | H | I | V | R | K | R | T | L | R | H | L | L | Q | E | R | D |
| 59 | F | M | R | K | R | H | I | V | R | K | R | K | L | R | H | L | L | Q | D | R | D |
| 60 | F | M | R | H | R | H | I | V | R | K | K | T | L | R | R | L | L | Q | E | R | E |
| 61 | F | M | R | H | R | K | L | V | R | K | K | T | L | R | R | L | L | Q | E | R | E |
| 62 | F | M | R | H | R | H | I | V | L | L | K | T | L | R | R | L | L | Q | E | R | E |
| 63 | F | M | R | K | R | H | I | V | R | K | H | T | L | R | R | L | L | Q | E | R | E |
| 64 | F | M | R | K | R | H | I | V | R | K | H | Q | L | Q | R | L | L | Q | E | R | E |
| 65 | F | M | R | K | H | H | I | V | R | K | H | T | L | R | R | L | Q | Q | E | R | E |
| 2 | F | R | M | H | R | I | R | V | R | T | K | L | R | L | R | L | R | Q | E | R | E |
| 66 | F | R | M | H | K | I | R | V | R | T | K | L | R | L | R | L | R | Q | E | R | E |
| 67 | F | R | M | H | R | I | K | V | K | T | K | L | R | L | R | L | R | Q | D | R | E |
| 68 | F | R | M | H | R | I | R | V | R | T | K | L | K | L | R | L | R | Q | E | R | E |
| 69 | F | R | M | H | R | I | R | V | R | T | K | L | R | L | R | L | K | Q | E | R | E |
| 70 | F | R | M | H | R | I | Q | V | R | T | K | L | R | Q | R | L | R | Q | D | R | E |
| 71 | F | M | R | Q | R | H | I | V | R | Q | R | T | L | R | Q | L | L | Q | E | R | E |
| 72 | F | M | R | Q | R | H | I | V | K | Q | R | T | L | R | Q | L | L | Q | D | R | E |
| 73 | F | M | R | Q | R | H | I | V | R | Q | R | T | L | R | Q | L | L | Q | E | — | — |
| 74 | F | M | R | Q | R | H | I | V | R | Q | R | T | L | R | Q | L | L | Q | E | R | E |
| 75 | F | M | R | Q | R | H | I | V | R | Q | R | T | L | K | Q | L | L | Q | D | R | — |
| 76 | F | M | R | Q | R | H | I | V | R | Q | R | L | L | R | Q | L | H | Q | E | R | E |
| 77 | F | M | R | Q | R | H | I | V | L | Q | R | T | L | R | Q | L | L | Q | E | R | E |
| 78 | F | M | R | Q | R | H | L | L | K | Q | R | T | L | R | Q | L | L | Q | E | — | — |
| 79 | F | M | R | Q | R | H | L | L | K | Q | Q | T | L | R | R | L | L | Q | E | — | — |
| 4 | — | — | — | — | — | — | I | V | R | K | R | T | L | R | R | L | L | Q | E | R | E |
| 80 | — | — | — | — | — | — | — | V | R | K | R | T | L | R | R | L | L | Q | E | R | E |
| 81 | — | — | — | — | — | — | — | — | R | K | R | T | L | R | R | L | L | Q | E | R | E |
| 82 | — | — | — | — | — | — | — | — | — | K | R | T | L | R | R | L | L | Q | E | R | E |
| 83 | — | — | — | — | — | — | — | — | — | — | R | T | L | R | R | L | L | Q | E | R | E |
| 84 | — | — | — | — | — | — | — | — | R | K | R | T | L | R | R | Q | L | Q | E | R | E |
| 85 | — | — | — | — | — | — | — | — | — | K | R | T | R | R | R | R | L | Q | E | R | E |
| 86 | — | — | — | — | — | — | — | V | R | K | R | V | L | R | K | K | Q | E | R | E |
| 5 | — | — | — | — | — | — | I | V | R | T | K | L | R | L | R | L | R | Q | E | R | E |
| 87 | — | — | — | — | — | — | — | V | R | T | K | L | R | L | R | L | R | Q | E | R | E |
| 88 | — | — | — | — | — | — | — | — | R | T | K | L | R | L | R | L | R | Q | E | R | E |
| 89 | — | — | — | — | — | — | — | — | — | T | K | L | R | L | R | L | R | Q | E | R | E |
| 90 | — | — | — | — | — | — | — | — | — | — | K | L | R | L | R | L | R | Q | E | R | E |
| 91 | — | — | — | — | — | — | — | V | R | T | K | L | R | L | R | L | R | Q | E | — | — |
| 92 | — | — | — | — | — | — | — | — | R | T | K | L | R | L | R | L | R | Q | E | R | — |
| 93 | — | — | — | — | — | — | — | — | — | T | K | L | R | L | R | L | R | Q | E | — | — |
| 94 | — | — | — | — | — | — | — | — | — | — | K | L | R | L | R | L | R | Q | E | R | — |
| 95 | — | — | — | — | — | — | — | V | R | T | K | L | R | Q | R | L | R | Q | E | — | — |
| 96 | — | — | — | — | — | — | — | — | R | T | K | L | R | L | R | L | L | Q | E | R | — |
| 97 | — | — | — | — | — | — | — | — | — | Q | K | L | R | L | R | L | R | Q | E | — | — |
| 98 | — | — | — | — | — | — | — | — | — | K | L | R | K | R | L | K | Q | E | R | — | |

As previously discussed, the inhibitor peptides of the present invention further comprise a cell penetrating component. Cell penetrating components are well known to one of ordinary skill in the art. Non-limiting examples of cell penetrating components include protein transduction domains such as PTD4, HSV type I protein VP22, Antanapedia protein transduction domain, and the like (see also Dietz and Bahr 2004, Molecular and Cellular Neuroscience 27:85-131, Beerens et al., 2003, Curr Gene Ther. 3(5):486-94, and Bitler et al., 2009, Clinical Cancer Research 15:100-109, the disclosures of which are incorporated herein in their entirety).

In some embodiments, the EGFR-based peptide is directly or indirectly connected to the cell penetrating component. In some embodiments, the cell penetrating component is N-terminal to the EGFR-based peptide. In some embodiments, the EGFR-based peptide is N-terminal to the cell penetrating component. In some embodiments, the EGFR-based peptide is connected to the cell penetrating component by a linker. Linkers are well known to one of ordinary skill in the art. In some embodiments, the linker is a peptide linker. In some embodiments, there is no linker (e.g., the linker is 0 amino acids in length). In some embodiments, the linker is 1-5 amino acids in length. In some embodiments, the linker is 1-10 amino acids in length. In some embodiments, the linker is 1-15 amino acids in length. In some embodiments, the linker is 1-20 amino acids in length. In some embodiments, the linker is 1-25 amino acids in length. In some embodiments, the linker more than 25 amino acids in length.

Enhancements of EGFR-based Peptide

Figures 5A, 5B:
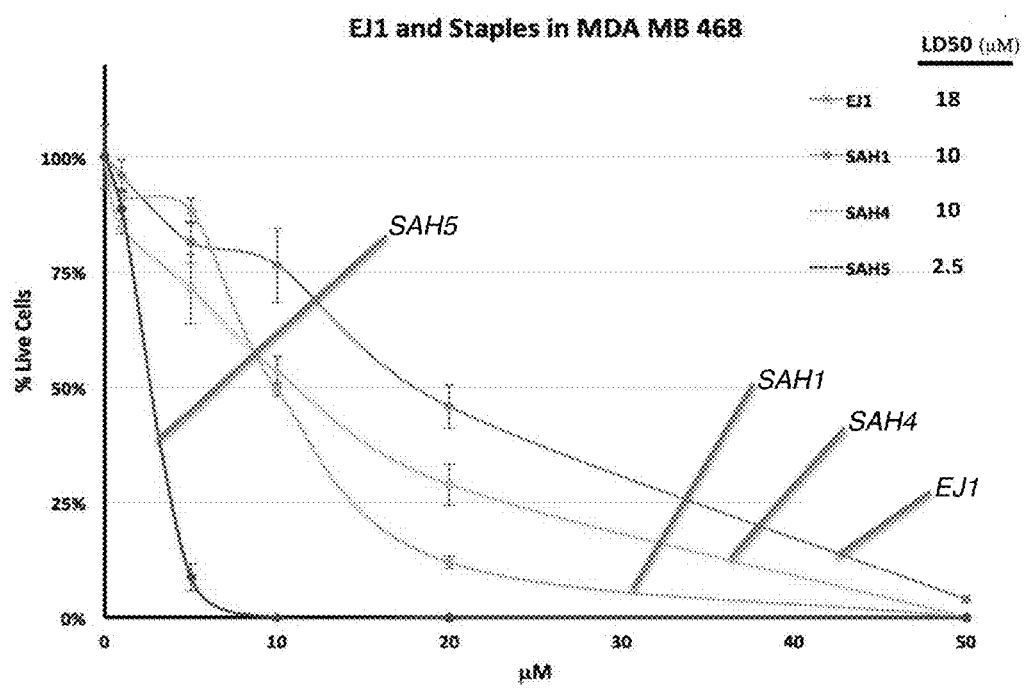
FIG. 5A shows the sequence of EJ1 (SEQ ID NO: 13, which is the PTD4 domain (YARAAARQARA (SEQ ID NO: 110) combined with SEQ ID NO: 1) and EJ1 control peptide (CP) (SEQ ID NO: 24, which is the PTD4 domain (YARAAARQARA (SEQ ID NO: 110) combined with SEQ ID NO: 12), followed by the stapled versions (SAH) (SEQ ID NO: 111 (the PTD4 domain (YARAAARQARA (SEQ ID NO: 110) combined with SEQ ID NO: 99), SEQ ID NO: 112 (the PTD4 domain (YARAAARQARA (SEQ ID NO: 110) combined with SEQ ID NO: 102), SEQ ID NO: 113 (the PTD4 domain (YARAAARQARA (SEQ ID NO: 110) combined with SEQ ID NO: 103)), noting where the non-natural amino acids were placed in green and blue.
FIG. 5B shows killing of MDA-MB-468 cells following treatment for 24 hrs with the indicated concentrations of the peptides (evaluated by MTT). $LD_{50}$ for each peptide is shown at the top right.

The inhibitor peptides of the present invention may further comprise a modification effective for lowering its $K_D$ (e.g., lowering the $K_D$ of the inhibitor peptide as compared to a $K_D$ of the inhibitor peptide without the modification). The modification may be effective for increasing the efficacy of the inhibitor peptide (e.g., increase the in vitro kill rate), e.g., as compared to the efficacy of the inhibitor peptide without the modification. In some embodiments, the modification comprises hydrocarbon stapling, e.g., one or more hydrocarbon staples. Methods of hydrocarbon stapling are known to one ordinary skill in the art (see, for example Wang et al., 2015, Org. Biomol. Chem. 12:6286, the disclosure of which is incorporated herein in its entirety). FIG. 5 shows examples of peptides of the present invention modified so as to have hydrocarbon staples. In SAH1-EJ1, SAH4-EJ1, and SAH5-EJ1, two amino acids were substituted with either (R)-2-{[(9H-fluoren-9-yl)methoxy]carbonylamino}-2-methyldec-9-enoic acid (also known as R8) or (S)-2-{[(9H-fluoren-9-yl)methoxy]carbonylamino}-2-methyl-hept-6-enoic acid (also known as S5). The present intention is not limited to R8 or S5, as alternatives may be used, which are known to one ordinary skill in the art (see, for example Wang et al., 2015, Org. Biomol. Chem. 12:6286, the disclosure of which is incorporated herein in its entirety. The present invention is not limited to the positions of stapling disclosed herein.

In some embodiments, the amino acids at positions i and i+4 are substituted. In some embodiments, the amino acids at positions i and i+7 are substituted. The present invention is not limited to this arrangement. The substitutions may occur for amino acids on the same face of the alpha helix structure. In some embodiments, two amino acids are substituted (e.g., for stapling). In some embodiments, at least four amino acids are substituted (e.g., for stapling).

In some embodiments, the amino acid at position $X_1$ is substituted (e.g., for stapling). In some embodiments, the amino acid at position $X_2$ is substituted (e.g., for stapling). In some embodiments, the amino acid at position $X_3$ is substituted (e.g., for stapling). In some embodiments, the amino acid at position $X_4$ is substituted (e.g., for stapling). In some embodiments, the amino acid at position $X_5$ is substituted (e.g., for stapling). In some embodiments, the amino acid at position $X_6$ is substituted (e.g., for stapling). In some embodiments, the amino acid at position $X_7$ is substituted (e.g., for stapling). In some embodiments, the amino acid at position $X_8$ is substituted (e.g., for stapling). In some embodiments, the amino acid at position $X_9$ is substituted (e.g., for stapling). In some embodiments, the amino acid at position $X_{10}$ is substituted (e.g., for stapling). In some embodiments, the amino acid at position $X_{11}$ is substituted (e.g., for stapling). In some embodiments, the amino acid at position $X_{12}$ is substituted (e.g., for stapling). In some embodiments, the amino acid at position $X_{13}$ is substituted (e.g., for stapling). In some embodiments, the amino acid at position $X_{14}$ is substituted (e.g., for stapling). In some embodiments, the amino acid at position $X_{15}$ is substituted (e.g., for stapling). In some embodiments, the amino acid at position $X_{16}$ is substituted (e.g., for stapling). In some embodiments, the amino acid at position $X_{17}$ is substituted (e.g., for stapling). In some embodiments, the amino acid at position $X_{18}$ is substituted (e.g., for stapling). In some embodiments, the amino acid at position $X_{19}$ is substituted (e.g., for stapling). In some embodiments, the amino acid at position $X_{20}$ is substituted (e.g., for stapling). In some embodiments, the amino acid at position $X_{21}$ is substituted (e.g., for stapling).

Table 4 below shows examples of peptides with substituted amino acids (R8 or S5) for hydrocarbon stapling. The present invention is not limited to these examples. In some embodiments, the amino acids at position $X_1$ and position $X_8$ are substituted (e.g., for stapling). In some embodiments, the amino acids at position $X_2$ and position $X_9$ are substituted (e.g., for stapling). In some embodiments, the amino acids at position $X_3$ and position $X_{10}$ are substituted (e.g., for stapling). In some embodiments, the amino acids at position $X_5$ and position $X_{12}$ are substituted (e.g., for stapling). In some embodiments, the amino acids at position $X_6$ and position $X_{13}$ are substituted (e.g., for stapling). In some embodiments, the amino acids at position $X_7$ and position $X_{14}$ are substituted (e.g., for stapling). In some embodiments, the amino acids at position $X_8$ and position $X_{15}$ are substituted (e.g., for stapling). In some embodiments, the amino acids at position $X_9$ and position $X_{16}$ are substituted (e.g., for stapling). In some embodiments, the amino acids at position $X_{10}$ and position $X_{17}$ are substituted (e.g., for stapling). In some embodiments, the amino acids at position $X_{11}$ and position $X_{18}$ are substituted (e.g., for stapling). In some embodiments, the amino acids at position $X_{12}$ and position $X_{19}$ are substituted (e.g., for stapling). In some embodiments, the amino acids at position $X_{13}$ and position $X_{20}$ are substituted (e.g., for stapling). In some embodiments, the amino acids at position $X_{14}$ and position $X_{21}$ are substituted (e.g., for stapling).

TABLE 4

| SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| 99 | F | M | R | R | R | H | I | R8 | R | K | R | T | L | R | S5 | L | L | Q | E | R | E |
| 100 | F | M | R | R | R | H | I | V | R8 | K | R | T | L | R | R | S5 | L | Q | E | R | E |
| 101 | R8 | M | R | R | R | H | I | S5 | R | K | R | T | L | R | R | L | L | Q | E | R | E |
| 102 | F | R8 | R | R | R | H | I | V | S5 | K | R | T | L | R | R | L | L | Q | E | R | E |

TABLE 4-continued

| SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| 103 | F | M | R | R | R | H | I | V | R | K | R | R8 | L | R | R | L | L | Q | S5 | R | E |
| 104 | F | M | R8 | R | R | H | I | V | R | S5 | R | T | L | R | R | L | L | Q | E | R | E |
| 105 | F | M | R | R | R8 | H | I | V | R | K | R | S5 | L | R | R | L | L | Q | E | R | E |
| 106 | F | M | R | R | R | R8 | I | V | R | K | R | T | S5 | R | R | L | L | Q | E | R | E |
| 107 | F | M | R | R | R | H | R8 | V | R | K | R | T | L | S5 | R | L | L | Q | E | R | E |
| 108 | F | M | R | R | R | H | I | V | R | R8 | R | T | L | R | R | L | S5 | Q | E | R | E |
| 109 | F | M | R | R | R | H | I | V | R | K | R | T | R8 | R | R | L | L | Q | E | S5 | E |

Figure 15A:
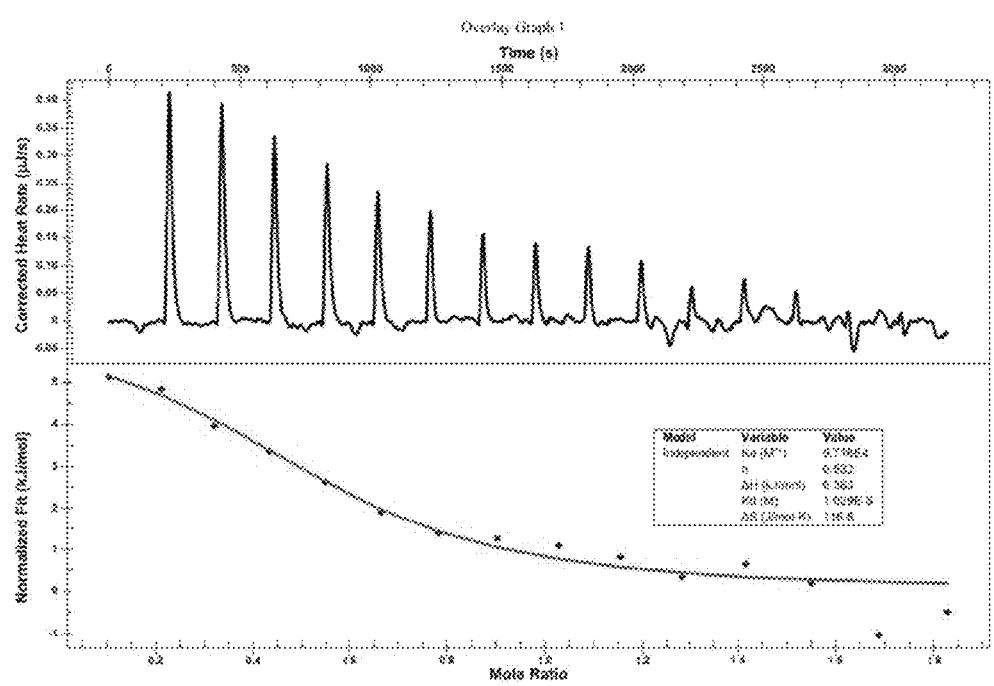

FIG. 15 shows that stapling can lower the $K_d$ of the inhibitor peptides. For example, FIG. 15A shows ITC experiments using ENLS1 at 100 uM with a target of Ecyl EGFR peptide at 500 uM. The $K_d$ for the experiment was 10 uM. (Note that in FIG. 15A, the n of 0.532 may suggest that there may be two ENLS1 peptides binding to the target. FIG. 15B shows ITC experiments using SAH-EJ1 at 100 uM (top) and 150 uM (bottom). The target was Ecyl EGFR peptide at 500 uM. The $K_d$ for the top experiment was 2.5 uM, the $K_d$ for the bottom experiment was 3.2 uM (averaging about 2.85 uM). Note that in both experiments, an n of 0.523 (top) and 0.437 (bottom) suggests that there may be two SAH-EJ1 peptides binding to the target.

In some embodiments, the inhibitor peptide binds to ENLS-1 with a $K_d$ of 15 uM or less in vitro. In some embodiments, the inhibitor peptide binds to ENLS-1 with a $K_d$ of 10 uM or less in vitro. In some embodiments, the inhibitor peptide binds to SAHEJ1 with a $K_d$ of 5 uM or less in vitro. In some embodiments, the inhibitor peptide binds to SAHEJ1 with a $K_d$ of 3 uM or less in vitro.

Functions of Inhibitor Peptides

The inhibitor peptides of the present invention may be important for treating conditions associated with aberrant ErbB activity. In some embodiments, the inhibitor peptide is effective to disrupt calcium signaling (e.g., when administered in vitro, when administered in vivo). In some embodiments, the inhibitor peptide is effective to increase reactive oxygen species (ROS) (e.g., when administered in vitro, when administered in vivo). In some embodiments, the inhibitor peptide is effective to activate apoptosis (e.g., when administered in vitro, when administered in vivo). In some embodiments, the inhibitor peptide is effective to activate necrosis (e.g., when administered in vitro, when administered in vivo).

In some embodiments, the inhibitor peptide is effective to reduce metastasis (e.g., when administered in vivo). In some embodiments, the inhibitor peptide is effective to inhibit tumor growth (e.g., when administered in vivo). For example, in some embodiments, the inhibitor peptide is effective for reducing growth of a tumor associated with one or more of aberrant ErbB1 activity, aberrant ErbB2 activity, ErbB3 activity (e.g., when administered in vivo). In some embodiments, the tumor is a breast tumor, brain tumor, ovarian tumor, prostate tumor, colon tumor, pancreatic tumor, or a lung tumor. In some embodiments, the inhibitor peptide inhibits growth or proliferation of leukemia-associated cells.

FIG. 6-FIG. 14 and Example 1 show examples of inhibitor peptides disrupting calcium signaling, increasing ROS, inhibiting tumor growth, etc.

Example 1

The following example is from Hart et al., 2013, Molecular Therapy 21(11):1996-2007, the disclosure of which is incorporated in its entirety herein.

Peptides were created to represent subdomains within ERBB1, from amino acids 643-663, and were tested for their ability to affect cell survival. This example demonstrates the ability of one of these jxm peptides to enter and kill cancer cells; regulate ERBB multimerization and activation; and regulate both calcium and mitochondrial pathways of cell survival. Also shown is that in a mouse model of breast cancer, treatment with this peptide displays no observable toxicity and has the ability to reduce tumor growth and metastasis.

ERBB1 jxm Peptides Reduce Cellular Viability

Figure 6:
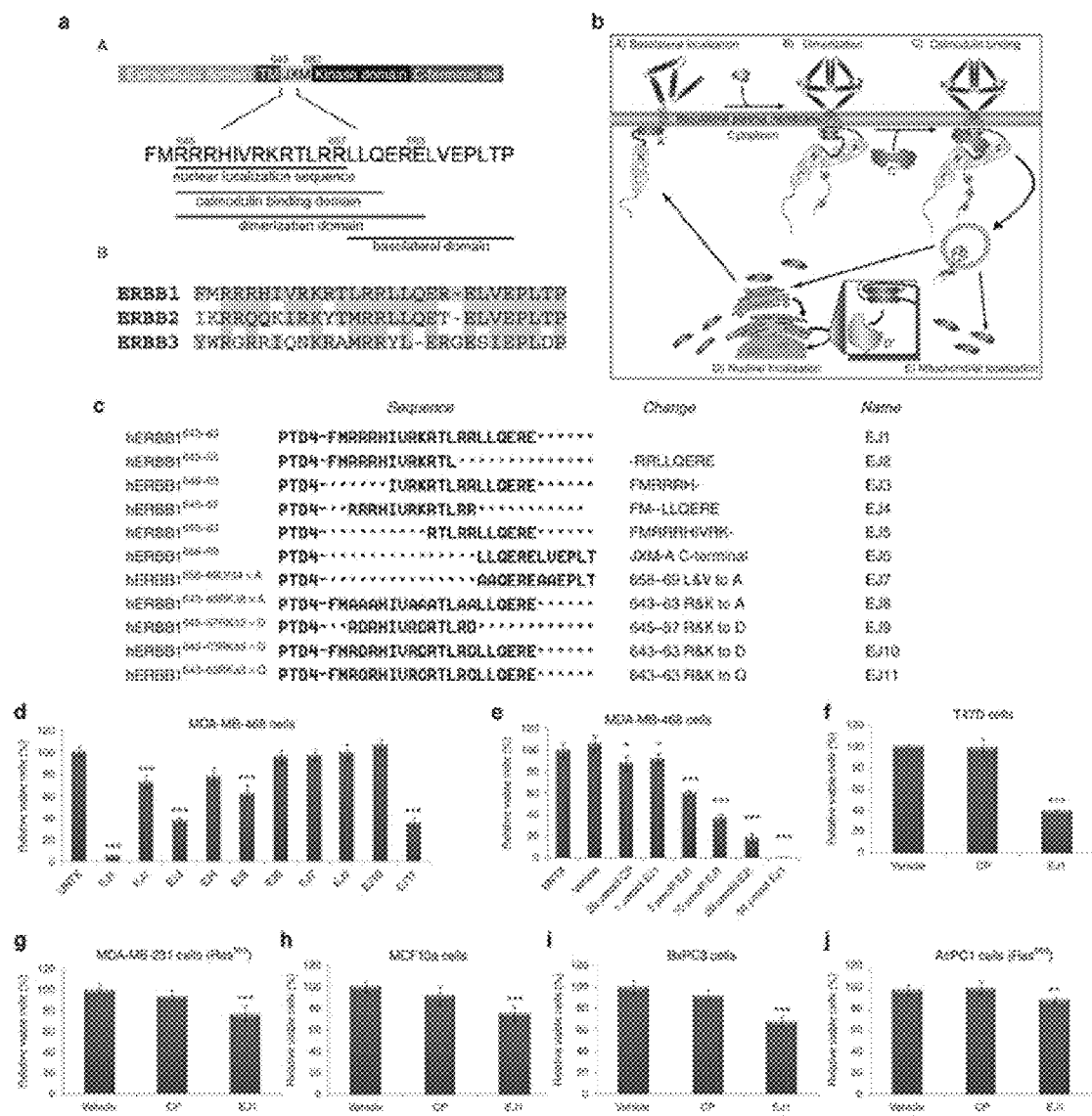
FIG. 6 shows juxtamembrane domain peptides reduce cell viability. (a) (A) Schematic diagram depicting relevant functional motifs of the ERBB1 juxtamembrane (jxm) domain and (B) jxm domains of ERBB1, ERBB2, and ERBB3, with conserved regions based on National Center for Biotechnology Information protein alignment highlighted in gray. (b) Model of interactions involving the ERBB1 jxm. (A) ERBB1 localizes through its jxm (A')-contained targeting domain to the basolateral plasma membrane. (B) Ligand binding induces conformational changes in ERBB1, whereby interactions between $jxm^{645-663}$ and the plasma membrane are disrupted, allowing dimerization and trans-phosphorylation. (C) $Ca^{2+}$ influx promotes ERBB1 jxm domain interactions with proteins such as calcium-bound calmodulin ($Ca^{2+}/CaM$) (C'). (D) Internalization and association with proteins such as importins $\alpha/\beta$ (D') and trafficking to locations such as the nucleus and mitochondria (D, E). (c) The amino acid number of ERBB1 is shown in the left column, corresponding to the specific amino acids shown in the middle column (sequence). Peptide designations are indicated in the right column. Changes from EJ1 in EJ2-11 are denoted in the second column from the right. (d-j) Cell lines were treated daily with 20 µmol/l EJ1, 20 µmol/l CP, or vehicle (water) for 3 days unless otherwise noted, and cell viability was determined by the MTT assay. Growth rates for vehicle-treated cells were set to 100%, and CP and EJ1 rates were adjusted accordingly. *P<0.05, P<0.01, *P<0.001 (Student's t-test). Error bars, mean±SD. (From Hart et al., 2013, Molecular Therapy 21(11):1996-2007, the disclosure of which is incorporated herein in its entirety.)

The conserved jxm domains of ERBB1, ERBB2, and ERBB3 contain sequences responsible for receptor dimerization, CaM binding, nuclear and mitochondrial localization, and membrane targeting (FIG. 6). Therefore, we set out to determine whether blocking the function of the jxm domain of the ERBB receptors would result in an effective ERBB-dependent cancer therapeutic strategy. To do this, we created cell-penetrating peptides to act as dominant-negative "decoys," thereby inhibiting endogenous jxm interactions. Peptides specific for jxm subdomains were synthesized downstream of the protein transduction domain-4 (PTD4; FIG. 6). Next, the effect of peptide treatment on cell viability was analyzed on the breast cancer cell line MDA-MB-468 by MTT (3-[4,5-dimethylthiazol-2-yl]-2,5-diphenyl tetra-zolium bromide) analysis after 3 days of treatment. We found that the amino acid region between hERBB1$^{643-663}$ (EJ1) demonstrated reduction in viability, and partial reduction was also obtained with subsequences within EJ1, including EJ2 (hERBB1$^{643-655}$), EJ3 (hERBB1$^{649-663}$), and EJ5 (hERBB1$^{653-663}$).

To test the role of charge of the peptide, one of the basic amino acids (Arg or Lys) in each of the three basic clusters of EJ1 was substituted with an acidic amino acid (Asp; EJ10, hereafter referred to as the control peptide, CP), and this step completely ablated the effects on viability (FIG. 6). Substituting those same basic amino acids with polar amino acids (Gln; EJ11) instead only marginally blocked the antiproliferative effects of EJ1 (FIG. 6). Note that replacement of the eight arginines and lysines with alanines resulted in an insoluble peptide (EJ8). Together, these results strongly implicate charge in the function of EJ1.

To determine whether the minimal nuclear localization sequence (EJ4) or the minimal basolateral domain (EJ6) was responsible for the antiproliferative effects of EJ1, peptides of these subdomains were created. No antiproliferative effect was observed for either peptide, implicating the CaM-binding and dimerization domains as essential for cell death (FIG. 6). After determining an optimal peptide concentration (20 μmol/l) EJ1 was tested for its ability to affect cell viability in additional breast cancer cell lines including T47D and MDA-MB-231 the immortalized breast epithelial cell line MCF10A, and pancreatic cancer cell lines including BxPC3, AsPC1 and MIA PaCa-2. In analyzing the effects of EJ1 in these lines, we found that its effects on cellular viability ranged from a minimum reduction of 1% in MIA PaCa-2 cells and 10% in AsPC1 and MDA-MB-231 cells to a maximum of 60% reduction in T47D cells during a 3-day treatment period (FIG. 6). Analysis of the ERBB expression profile (including ERBB1, ERBB2, and ERBB3) in these cell lines demonstrated expression of at least two out of the three ERBB receptors in each of the lines. Interestingly, AsPC1, MIA PaCa-2, and 231 cells, all of which showed little response to EJ1 treatment, possess mutant forms of the protein Kras. Importantly, EJ1 had no effect on the viability of immortalized Chinese hamster ovary (CHO) cells that express low endogenous levels of the ERBB receptors.

EJ1 Inhibits ERBB Activation while Promoting Receptor Multimerization

Figure 7:
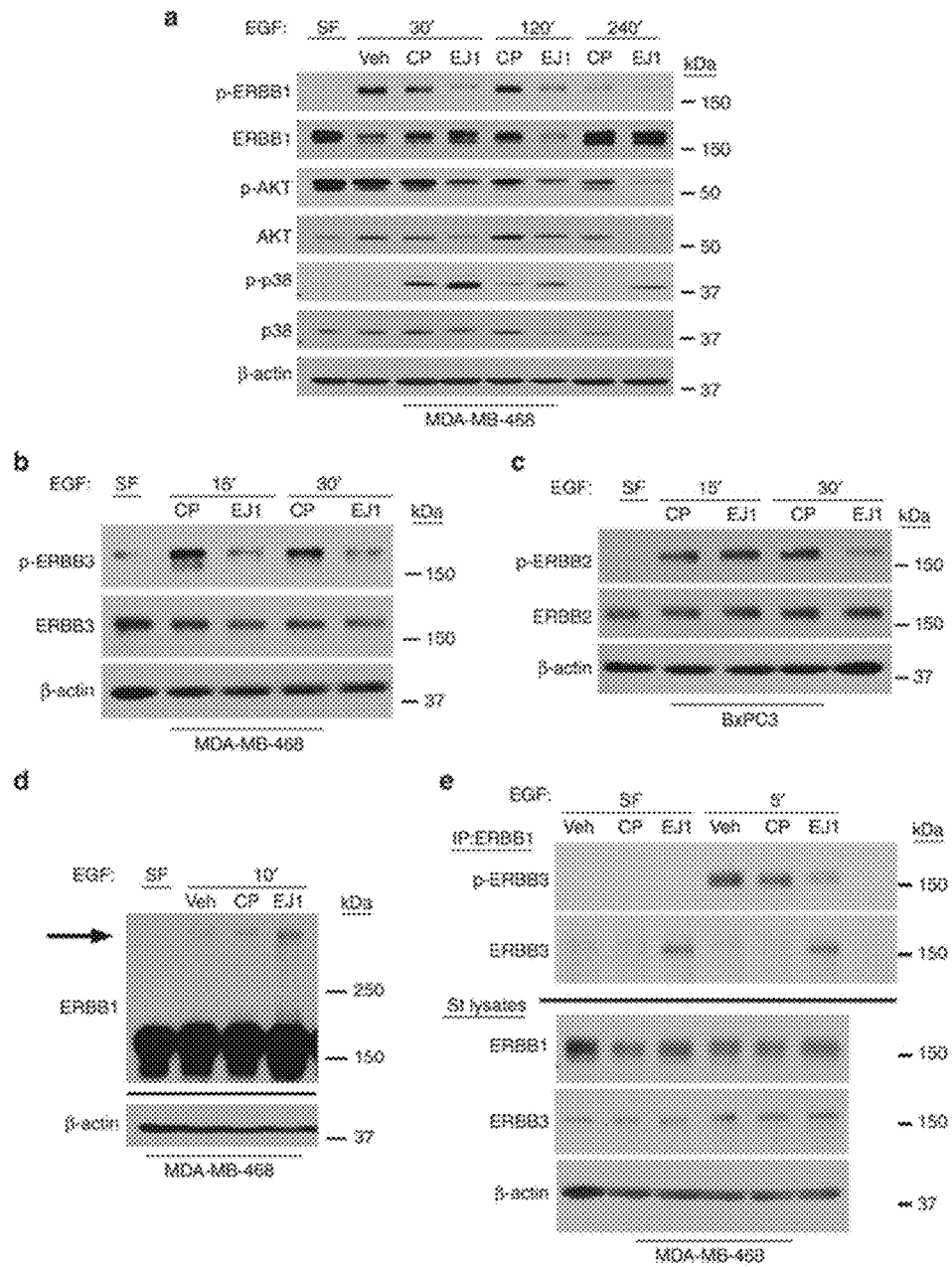
FIG. 7 shows EJ1 peptide induces the formation of inactive ERBB multimers. (a, c) MDA-MB-468 cells or (b) BxPC3 cells were treated with 100 or 50 ng/ml EGF (respectively) in combination with water (Veh), 20 µmol/l CP, or 20 µmol/l EJ1 for the indicated times and lysed. Protein levels were determined as indicated. (d) MDA-MB-468 cells were treated with peptides for 10 minutes on ice. Then, 100 ng/ml EGF was added to the medium and incubated for another 10 minutes on ice, followed by cross-linking with 3 µmol/l DMS. Lysates were evaluated by western blotting for ERBB1 and β-actin. (e) MDA-MB-468 cells were treated similarly, but without cross-linker, lysed, and immunoprecipitated (ERBB1 Ab-13). Molecular weights are shown to the right. (From Hart et al., 2013, Molecular Therapy 21(11):1996-2007, the disclosure of which is incorporated herein in its entirety.)

To determine whether EJ1 affects ERBB1 activity, we first treated both MDA-MB-468 and BxPC3 cells with EJ1, CP, or vehicle in the presence or absence of EGF to activate ERBB1 (FIG. 7). We found that EJ1 significantly suppressed EGF-induced phosphorylation of ERBB1. This suppression also affected downstream signaling partners, resulting in a reduction of p-AKT. Interestingly, treatment with EJ1 also resulted in a loss of total protein for AKT and p38. In addition, an increase of the activated stress response kinase, p38, was observed after EJ1 treatment. In addition to blocking the activation of ERBB1, we found that EJ1 treatment similarly inhibited the trans-phosphorylation of ERBB2 and ERBB3 in response to EGF. Note that BxPC3 cells were used to test ERBB2 activation because 468 cells do not express detectable levels of ERBB2. Because EJ1 peptide mimics the dimerization domain of ERBB1, a domain that is conserved in ERBB2 and ERBB3 (FIG. 6) we next evaluated the ability of EJ1 to block dimerization. To first evaluate the effects of EJ1 on ERBB1 homodimers, MDA-MB-468 cells were treated with EGF in addition to EJ1 or controls in the presence of a nonreducible cross-linker. Surprisingly, we found that EJ1 induced the formation of high-molecular-weight ERBB1 multimers (FIG. 7, arrow). To determine whether EJ1 had a similar effect on heterodimer formation, cells were treated with EGF in the presence of EJ1 or controls and evaluated for the formation of ERBB1/ERBB3 heterodimers by co-immunoprecipitation. Again, EJ1 treatment resulted in suppression of ERBB3 phosphorylation and an increase in the formation of ERBB1/ERBB3 heterodimers even in the absence of serum. Finally, we observed a direct interaction between ERBB1 and EJ1 by the pull down of biotinylated EJ1 with ERBB1, which preferentially occurred in the absence of EGF treatment. Together, these results indicate that EJ1 interacts with ERBB1 and promotes the inactive multimerization of ERBB receptors.

EJ1 Affects $Ca^{2+}$/CaM Downstream Signaling

Figure 8:
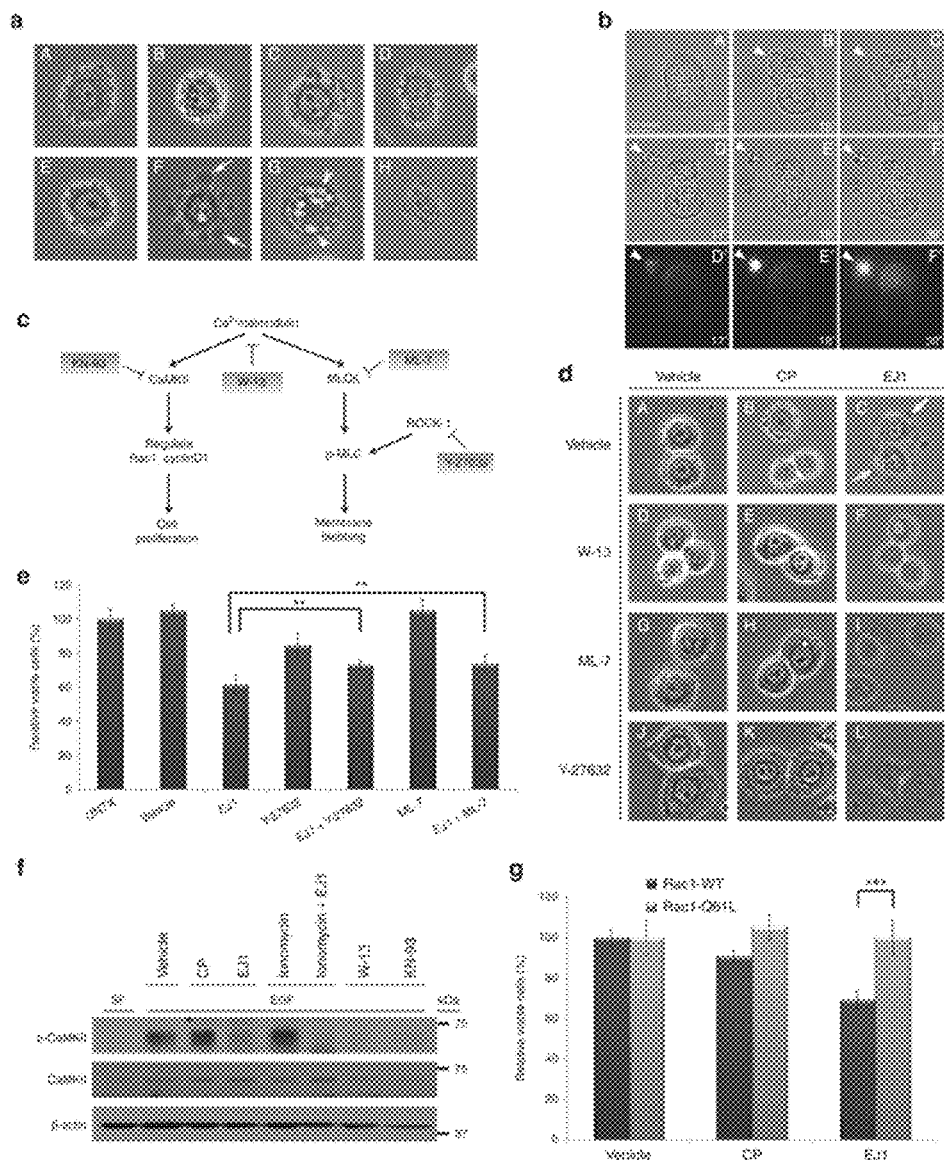
FIG. 8 shows EJ1 peptide affects $Ca^{2+}/CaM$ downstream signaling. (a) MDA-MB-468 cells were treated with either 20 µmol/l CP (A-D) or 20 µmol/l EJ1 (E-H) for 0 minutes (A, E), 15 minutes (B, F), 60 minutes (C, G), or 16 hours (D, H). Arrows indicate membrane blebs and arrowheads indicate intracellular vacuoles. (b) BxPC3 cells were serum starved overnight, then treated with 20 µmol/l EJ1 and 50 ng/ml Texas-Red-labeled EGF, and imaged for 30 minutes with an Olympus IX71 deconvolution microscope. Panels A-F are bright field images, D'-F' are red channel images (Texas-Red-labeled EGF). Arrowheads indicate locations of EGF accumulation on membrane protrusions. (c) Diagram depicts $Ca^{2+}/CaM$-regulated signaling pathway, and inhibitors acting at different targets are indicated. (d) MDA-MB-468 cells were pretreated with 50 µmol/l W-13 (D-F), 10 µmol/l ML-7 (G-I), or 10 µmol/l Y-27632 (J-L) in complete medium at 37° C. for 30 minutes and then treated with vehicle, 20 µmol/l CP, or 20 µmol/l EJ1 in combination with W-13, ML-7, or Y-27632 in complete medium at 37° C. for 15 minutes. Images represent the bright field images. Arrows indicate membrane blebbing. (e) MDA-MB-468 cells were untreated (UNTX) or treated with water (Vehicle), 20 µmol/l EJ1, 10 µmol/l Y-27632, or 10 µmol/l ML-7 alone or EJ1 in combination with Y-27632 or ML-7, and the viability was assessed by the MTT assay. P<0.01 (Student's t-test). Error bars, mean±SD. (f) MDA-MB-468 cells were either in serum-free medium (SF) or stimulated with 100 ng/ml EGF (EGF) and then incubated with water (Vehicle), 20 µmol/l CP, 20 µmol/l EJ1, 2 µmol/l ionomycin, 50 µmol/l W-13, 100 µmol/l KN-93, or EJ1 in combination with ionomycin for 15 minutes. Lysates were immunoblotted with antibodies as indicated. (g) Stable, neomycin-selected NIH3T3 cell lines were created, expressing either Rac1 wild-type (Rac1-WT) or Rac1 constitutively active mutant (Rac1-Q61L). Cells were treated with water (Vehicle), 20 µmol/l CP, or 20 µmol/l EJ1, and the viability was assessed by MTT. *P<0.001 (Student's t-test). Error bars, mean±SD. (From Hart et al., 2013, Molecular Therapy 21(11):1996-2007, the disclosure of which is incorporated herein in its entirety.)

In addition to the dimerization domain, the sequence for EJ1 overlaps with the CaM-binding domain for ERBB1. $Ca^{2+}$/CaM signaling regulates many different cellular events, such as membrane dynamics, cell survival, mitochondrial function, and motility. We began by evaluating whether EJ1 was affecting membrane dynamics by treating MDA-MB-468 cells with either CP (FIG. 8) or EJ1 (FIG. 8) and examining cell morphology. We found that in 15 minutes, EJ1-treated cells formed large membrane protrusions or blebs (F, arrows)). By 60 minutes of treatment, cells had formed large intracellular vacuoles (G, arrowheads). After 16 hours, many EJ1-treated cells appeared dead (H). In an effort to determine whether the cell blebbing corresponded to ERBB1 localization, cells were treated with Texas-Red-labeled EGF, Alexa Fluor 488-labeled transferrin, and EJ1 simultaneously. Although both ligands were detected in cells treated with EJ1, large membrane protrusions quickly formed specifically where EGF was concentrated, resulting in focused membrane explosions (F-F', arrowhead). This indicates that EJ1-induced membrane blebbing occurs in membrane regions containing ERBB1. To investigate whether membrane blebbing is a result of ERBB1 kinase inhibition, MDA-MB-468 cells were treated with AG1478, an ERBB1 kinase inhibitor, and membrane dynamics were observed. No membrane blebbing was observed, indicating that membrane blebbing is not a result of kinase inhibition. $Ca^{2+}$/CaM signaling regulates many different downstream pathways, such as CaMKII and MLCK. CaMKII regulates cell proliferation, whereas MLCK phosphorylates myosin light chain (MLC) and regulates actinomyosin reorganization during membrane blebbing (as depicted in FIG. 8). To investigate whether EJ1-induced membrane blebbing was through the MLCK pathway, MDA-MB-468 cells were treated with vehicle, CP, or EJ1 alone (A-C) or in combination with the CaM inhibitor W-13 or the MLC phosphorylation inhibitors ML-7 and Y-27632 (D-L). We found that both the CaM inhibitor W-13 and the MLC phosphorylation inhibitors ML-7 and Y-27632 completely inhibited EJ1-induced membrane blebbing. To determine whether these effects on membrane blebbing were related to cell survival, the inhibitors were used in conjunction with EJ1 in an MTT assay. We observed that after 1 day of treatment, both Y-27632 and ML-7 could significantly reduce the effects of EJ1. To determine whether EJ1 could also affect CaMKII activation, MDA-MB-468 cells were treated with vehicle, CP, or EJ1 with or without ionomycin, an ionophore capable of inducing $Ca^{2+}$/CaM signaling. Although EGF and ionomycin both induced CaMKII phosphorylation, this induction was suppressed by EJ1. To test whether inhibition of CaMKII activity was one of the causes of cell death, we used NIH3T3 cells overexpressing Rac1, one of the key downstream effectors of CaMKII, and assessed cell viability in response to EJ1. Overexpression of constitutively active Rac1 (Rac1-Q61L), compared with wild-type Rac1 (Rac1-WT), significantly rescued EJ1-induced cell death. These results indicated that suppression of CaMKII activation by EJ1 could be circumvented by overexpression of an activated downstream component of the CaMKII pathway. Taken together, EJ1 can simultaneously activate the MLCK pathway and inhibit the CaMKII pathway, and both pathways are integral to the EJ1-mediated reduction in cell survival.

EJ1 Affects Cell Survival through Apoptosis/Necrosis

Figure 9:
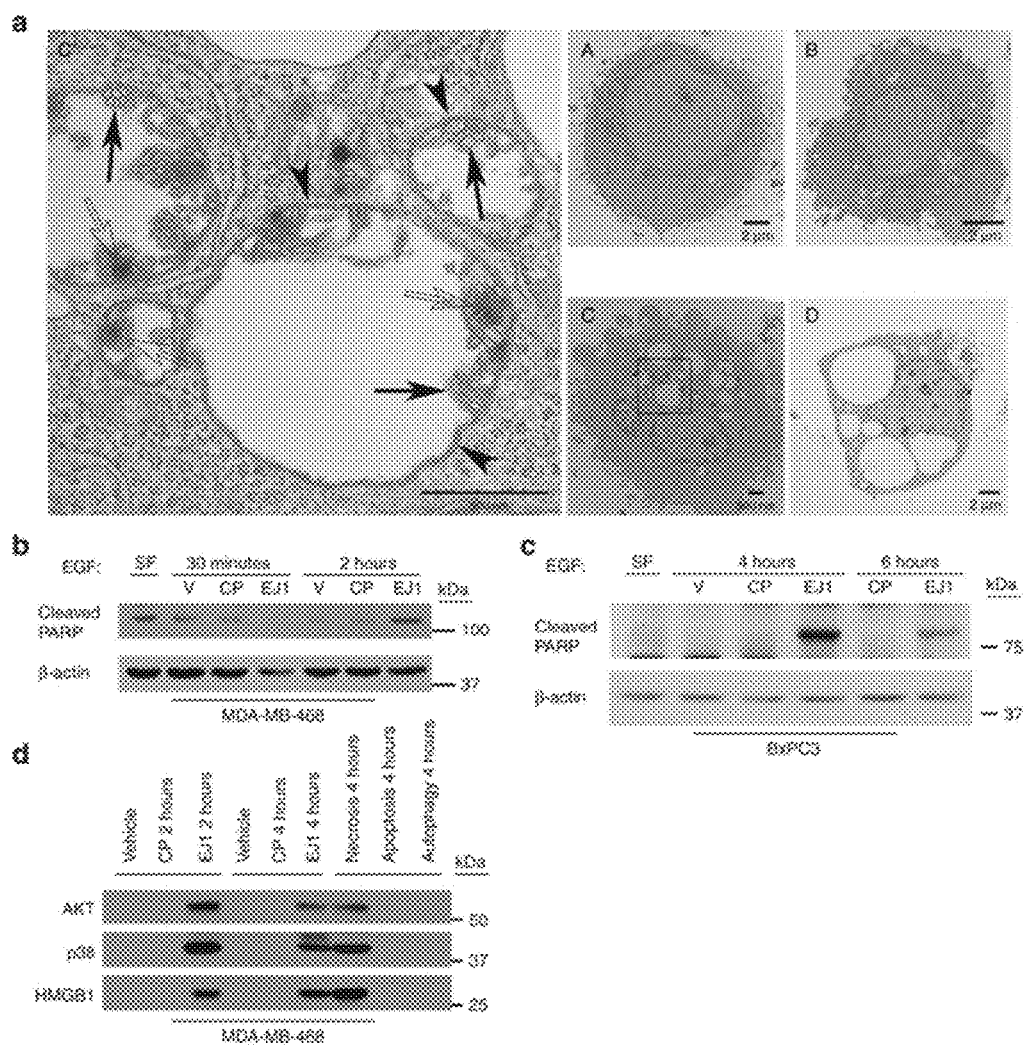
FIG. 9 shows EJ1 peptide induces both apoptosis and necrosis. (a) MDA-MB-468 cells were treated with 20 µmol/l EJ1 for (A) 0 minutes, (B) 5 minutes, (C and C') 30 minutes, or (D) 2 hours and then prepared for transmission electron microscopy (TEM). Arrowheads indicate double membrane structures, filled arrows indicate organelle debris, and open arrows indicate electron-dense deposits. (b, c) MDA-MB-468 and BxPC3 cells were serum starved before treatment with EGF at 100 or 50 ng/ml respectively, along with water (V), 20 µmol/l CP, and 20 µmol/l EJ1 for indicated time points and lysed. (d) MDA-MB-468 cells were treated as in (b) along with 10 ng/ml human TNF-α and 35 µmol/l cycloheximide (apoptosis inducer), 2 µmol/l ionomycin and 50 µmol/l CCCP (necrosis inducer), and 100 nmol/l rapamycin (autophagy inducer) for the indicated times and media were collected. Protein in medium was precipitated as described in ref. 28. (From Hart et al., 2013, Molecular Therapy 21(11):1996-2007, the disclosure of which is incorporated herein in its entirety.)
Figure 10:
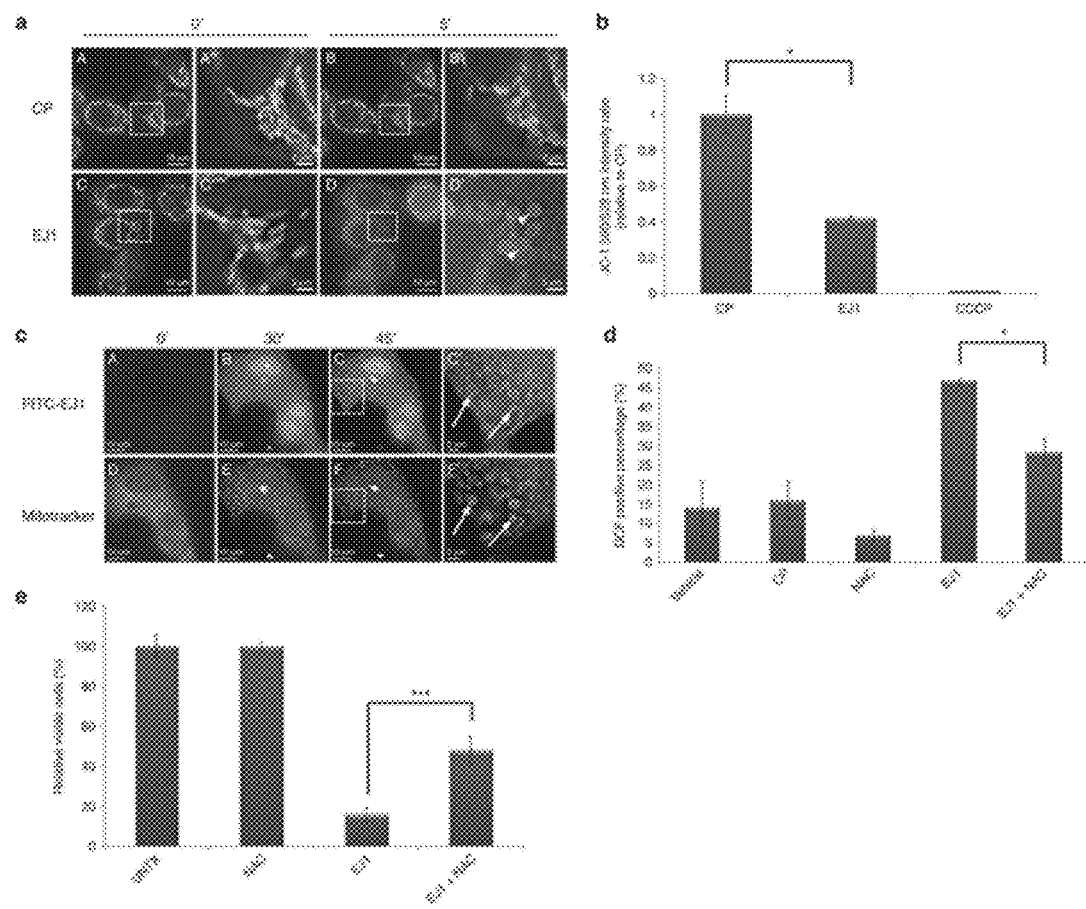
FIG. 10 shows EJ1 peptide localizes to the mitochondria and causes mitochondrial disruption and ROS generation. (a) MDA-MB-468 cells were incubated in serum-free media with 200 nmol/l MitoTracker Red CMXRos and 5 μg/ml Hoechst 33342 nuclear stain, followed by either 20 μmol/l CP (A-B') or 20 μmol/l EJ1 (C-D'), and imaged at 0 minutes (A, A'; and C, C') or at 5 minutes (B, B'; and D, D'). (b) MDA-MB-468 cells were incubated with 1 μmol/l JC-1, followed by 20 μmol/l CP, 20 μmol/l EJ1, or 50 μmol/l CCCP. Results were calculated as the ratio of the 514/590 nm to 514/529 nm fluorescences and the ratio for CP-treated sample was set as 1. *P<0.05, Student's t-test. Error bars, mean±SD. (c) T47D cells were treated with MitoTracker (shown in D-F and F') and Hoechst 33342 as in (a) and incubated with 20 μmol/l FITC-labeled EJ1 (shown in A-C and C'). (d) MDA-MB-468 cells were stained with 10 μmol/l DCFH-DA, followed by water (Vehicle), 20 μmol/l CP, 0.5 mmol/l NAC, and 20 μmol/l EJ1 or EJ1 in combination with NAC. Cells were then sorted by flow cytometer and analyzed by Cellquest Pro 4.0 software. The results are expressed as the percentage of DCFH fluorescence-positive cells. *P<0.05, Student's t-test. Error bars, mean±SD. (e) MDA-MB-468 cells were treated with 0.5 mmol/l NAC alone, 20 μmol/l EJ1 alone, or NAC in combination with EJ1, and viability was assayed by the MTT assay. ***P<0.001, Student's t-test. Error bars, mean±SD. (From Hart et al., 2013, Molecular Therapy 21(11):1996-2007, the disclosure of which is incorporated herein in its entirety.)
Figure 11:
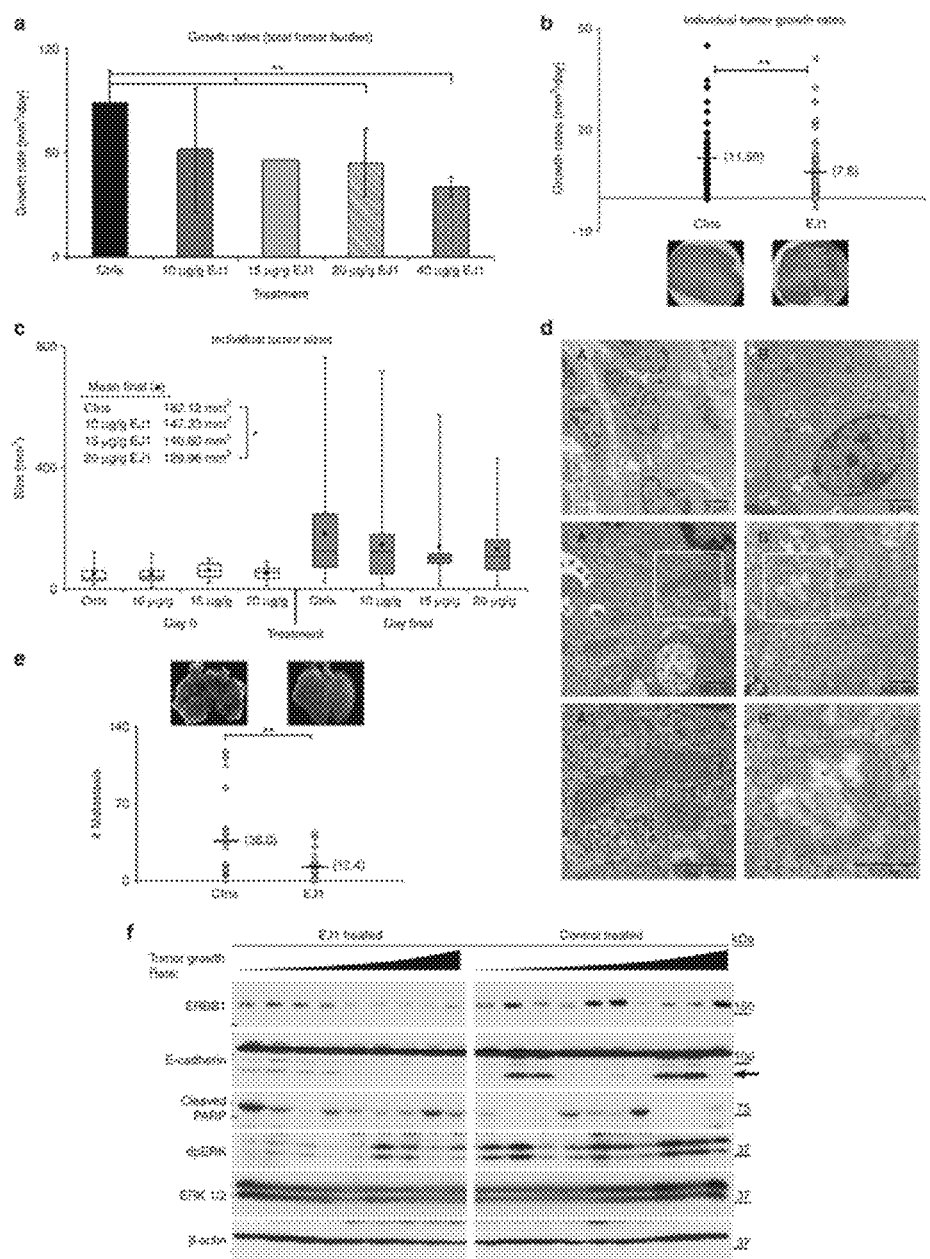
FIG. 11 shows EJ1 peptide inhibits tumor progression in MMTV-pyMT transgenic mice. (a) MMTV-PyMT mice were allowed to develop tumors of 50 mm³ before being treated once daily (i.p. injection) with indicated doses of Ctrls (20 μg/g CP5 (n=3), PBS (n=2)) and EJ1 (10 μg/g (n=6), 15 μg/g (n=1), and 20 μg/g (n=7), or twice-daily doses of 40 μg/g (n=3)). Peaks represent average total tumor burden growth rate in mm³ per day for each treatment. Error bars, mean±SD. *P<0.05; P<0.005, Student's t-test. (b) Control (12 mice (20 μg/g CP5 (n=5), PBS (n=7), n=100 tumors) vs. 20 μg/g EJ1-treated (eight mice, n=72 tumors) individual tumor growth rates and representative tumor images (insets). Mean denoted by horizontal line. P<0.005, Student's t-test. (c) Mice were treated with 10, 15, or 20 μg/g body weight EJ1 or control for 21 days and tumors were measured twice weekly. Box plots are shown for day 0 (10 μg/g EJ1: n=6 mice, 21 tumors; 15 μg/g EJ1: n=1 mouse, two tumors; 20 μg/g EJ1: n=8 mice, 24 tumors; Ctrls: n=12 mice, 41 tumors) and final day (10 μg/g EJ1: n=6 mice, 46 tumors; 15 μg/g EJ1: n=1 mouse, nine tumors; 20 μg/g EJ1: n=8 mice, 72 tumors; Ctrls: n=12 mice, 100 tumors). Boxes denote median and the second and third quartiles, with whiskers indicating lowest and highest quartiles. Mean values are represented by filled black squares. *P<0.05, Student's t-test. (d) EJ1-(B-B") and CP (A-A")-treated tumors from MMTV-PyMT mice were sectioned and imaged by TEM. Representative mitochondria are highlighted in A'-A" and B'-B". (e) Control vs. EJ1-treated lung tumor numbers. Mean denoted by horizontal line. **P<0.005, Student's t-test. Representative lung images are also shown. (f) Lysates from treated MMTV-pyMT mice (arranged by increasing tumor growth rate) were separated by SDS-PAGE and immunoblotted for the indicated proteins. Arrow indicates 85-kDa E-cadherin species associated with metastasis. (From Hart et al., 2013, Molecular Therapy 21(11):1996-2007, the disclosure of which is incorporated herein in its entirety.)

To investigate the vacuoles formed in FIG. 8 further, we performed transmission electron microscopy (FIG. 9). MDA-MB-468 cells were treated with EJ1 and evaluated at several time points (FIG. 9a (A-D)). By 30 minutes, double-membrane structures (FIG. 9a (C', arrowheads)) filled with organelle debris (FIG. 9a (C', filled arrows)) and electron-dense deposits (FIG. 9a (C', open arrows)) were observed in EJ1-treated but not untreated cells (FIG. 9a (A)). As double-membrane structures are hallmarks of autophagy and membrane blebbing is a hallmark of apoptosis, we next evaluated the cells for induction of each of these events. Evaluation of the conversion of microtubule-associated protein 1 light chain 3-I or II upon treatment with EJ1 indicated that the peptide was inducing some level of autophagy. However, the autophagy inhibitor, 3-MA, was not able to rescue EJ1-induced effects on cell viability, membrane morphology, or vacuole formation, suggesting that any induced autophagy was more likely a protective response to EJ1 rather than a mode of cell death. To investigate whether the cell death was apoptosis related, MDA-MB-468 and BxPC3 cells were evaluated for PARP cleavage (FIG. 9b,c) with a strong induction observed upon EJ1 treatment compared with CP treatment at 2, 4, and 6 hours, indicating an induction of apoptosis by EJ1. Further analysis of apoptosis by propidium iodide and Annexin V staining with flow cytometry at 4 hours also revealed an EJ1-induced increase in the percentage of Annexin V-positive cells compared with treatment with CP. This induction was particularly strong in BxPC3 cells under serum-free conditions. To evaluate necrosis as an additional factor in cell death, culture media from EJ1-treated MDA-MB-468 cells was collected and evaluated for the release of the nuclear protein HMGB1. We found detectable HMGB1 in EJ1-treated but not control-treated cell media (FIG. 9d). Interestingly, we also found AKT and p38 in EJ1-treated cell media (FIG. 9d), which was consistent with our previous findings (FIG. 7a) that EJ1 resulted in loss of cellular AKT and p38. These data indicate that EJ1 causes cell death through both apoptosis and necrosis.

Accumulation of EJ1 at Mitochondria Causes Mitochondrial Disruption and Reactive Oxygen Species Generation During our evaluation of intracellular vesicles created by EJ1 treatment, we observed the presence of what appeared to be remnant mitochondrial cristae within these vacuolar structures. To further explore the effects of EJ1 treatment on mitochondria, MDA-MB-468 cells were labeled with Mitotracker, treated with either EJ1 or CP, and imaged (FIG. 10a (A-D)). Mitochondria appeared enlarged and rounded very rapidly upon EJ1 treatment (FIG. 10a (D', arrowheads)). Similar results were observed for T47D, NIH-3T3, CHO, and BxPC3 cells. To determine whether the mitochondrial membrane was being damaged during this process, cells were treated with JC-1 dye, a reporter of mitochondrial membrane potential (MMP). MDA-MB-468 cells were labeled with JC-1 for 15 minutes and then treated for 2 hours with CP, EJ1, or carbonyl cyanide 3-chlorophenylhydrazone (CCCP), a compound that disrupts mitochondrial integrity, as a positive control for mitochondrial damage. A significant loss of MMP was observed with EJ1 treatment (FIG. 10b). To determine whether these effects could be due to EJ1 directly interacting with mitochondria, MDA-MB-468 and T47D (FIG. 10c) cells were treated with fluorescein isothiocyanate (FITC)-labeled EJ1 and Mitotracker. Visualization over time demonstrated increased colocalization between EJ1 and mitochondria, indicating that these effects of EJ1 could be due to direct targeting of the mitochondria (FIG. 10c (A-F, arrows)]. Overall, these results indicate that EJ1 interacts with mitochondrial membranes and causes mitochondrial swelling and loss of MMP. There are multiple intracellular events that can lead to or result from loss of MMP, such as modulation of $Ca^{2+}$ concentration or reactive oxygen species (ROS) within the cells. To measure intracellular ROS levels in response to EJ1, we used 2',7'-dichlorofluorescein (DCFH) diacetate, which becomes fluorescent DCF in the presence of ROS. MDA-MB-468 cells were treated with CP, N-acetyl cysteine (NAC, a ROS scavenger that reduces intracellular ROS levels), EJ1, or NAC+EJ1 (FIG. 10d). While EJ1 treatment increased intracellular ROS levels as indicated by DCF fluorescence, cotreatment with NAC significantly reduced EJ1-induced ROS levels. We next sought to determine whether mitigation of ROS would prevent EJ1-induced cell death. We found that cotreatment of cells with EJ1 and NAC could indeed significantly rescue EJ1-induced cell death (FIG. 10e). These data demonstrate a role for intracellular ROS in EJ1-mediated cell death.

EJ1 Reduces Tumor Growth and Metastasis in MMTV-pyMT Transgenic Mice

We next set out to determine whether EJ1 would function as an antitumor therapy agent in vivo. We tested the peptide on the MMTV-pyMT murine model of breast cancer, which develops synchronous, multifocal mammary tumors in all 10 mammary glands with a multistep progression that resembles human disease. Intraperitoneal delivery of several EJ1 dosages were tested, and 20 µg/g body weight was chosen for further study (FIG. 11a). This dosage of EJ1 (n=8), CP (n=5), or an equivalent volume of PBS (n=7) were then given to tumor-bearing mice, daily, for the course of the study (see "Materials and Methods below"). Similar day 0 occupancy and time of treatment are demonstrated for EJ1 and Control mice. We found that individual tumor growth rates and average tumor size were significantly reduced by treatment with EJ1 compared with CP or PBS (FIG. 11b, FIG. 11c).

Additionally, many resected EJ1-treated tumors were necrotic in appearance compared with those in controls (FIG. 11b (insets)). Transmission electron microscopy analysis of tumors after treatment also revealed damaged mitochondria in EJ1-treated tumors, similar to those seen in vitro (FIG. 11d). Importantly, no toxicity from this dose of EJ1 was observed (weight loss, grooming behavior, or gross changes to organs upon necropsy). Evaluation of post-study tumor lysates and quantification by densitometry revealed a 10% decrease in ERBB1 expression in EJ1-treated mice, indicating ERBB1-expressing cells may have been selectively targeted. In addition, we observed a 50-60% decrease in doubly phosphorylated form of MAPK/Erk (dpERK) and ~30% increase in the presence of the apoptotic indicator, cleaved PARP, in EJ1-treated mice (FIG. 11f). Similar examination of ERBB2 protein and phosphorylation revealed no significant reductions in EJ1-treated animals. Our analysis of protein expression in ERBB-related downstream signaling pathways revealed a significant decrease in the expression of an ~80-kDa fragment of E-cadherin in EJ1-treated, relative to CP-treated mice (FIG. 11f, arrow). Several studies have correlated the expression of the soluble 80-kDa form of E-cadherin with ERBB activity, along with the presence of metastasis or an increased metastatic potential. The MMTV-pyMT transgenic mice present with lung metastasis; we therefore evaluated the effects of EJ1 on lung metastasis. Assessment by bright field microscopic analysis and hematoxylin and eosin stain of tissue architecture showed that, on average, the lungs of EJ1-treated mice had significantly less metastatic foci than did comparable Control-treated mice (FIG. 11e and inset; average controls=36 metastases/lung, average EJ1=12 metastases/lung).

Materials and Methods

Cell Culture and Plasmids.

All cell lines were obtained from the American Type Culture Collection and grown under 5% $CO_2$. MDA-MB-468, MDA-MB-231, T47D, AsPC1, and BxPC3 cell lines were grown in RPMI (Cellgro) supplemented with 10% (5% for 468 cells) fetal bovine serum. MIA PaCa-2 cells were grown in DMEM and similarly supplemented as per ATCC guidelines. MCF10A cells were grown as previously described. Rac1-WT and Rac1-Q61L plasmids were obtained from Addgene (Cambridge, Mass.).

Antibodies.

The following antibodies were obtained from Santa Cruz Biotechnology (Dallas, Tex.): EGFR 1005, ERBB3 C-17, and CaMKII. EGFR Ab-13 was obtained from NeoMarkers (Fremont, Calif.), and the following antibodies were obtained from Cell Signaling (Danvers, Mass.): p-EGFR (pY845), Her2/ERBB2, Atg12, PARP, cleaved caspase 3, p-ERBB2 (pY1248), p-ERBB3 (pY1289), p-CaMKII (pT286), p-AKT (pS473), AKT, p42/44 MAPK (ERK 1/2), HMGB1, p-p38 (pT180/Y182), and p38. In addition, dpERK and β-actin antibodies were from Sigma (St Louis, Mo.), E-cadherin antibody was from BD Biosciences (San Jose, Calif.), and Calmodulin antibody was from Millipore (Billerica, Mass.).

Peptide Synthesis.

The EJ peptides were synthesized by GenScript (Scotch Plains, N.J.), delivered lyophilized, and stored at −20° C. Peptides were resuspended as needed at 1 mmol/1 in water and stored for up to 2 weeks at 4° C. EJ1 peptide sequences are shown conjugated to the PTD4 domain (YARAAAR-QARA (SEQ ID NO: 110)) in FIG. 6c.

Western Blotting, Immunoprecipitation, Crosslinking/Dimerization, and MTT Assays.

Protein lysate preparation, immunoprecipitation, and western blotting were performed as described previously. For cross-linking, cells were first incubated according to manufacturer instructions with 3 μmol/l DMS, a membrane-permeable, noncleavable, cross-linking agent (Thermo Scientific, Waltham, Mass.). Cells were analyzed both by the MTT assay following manufacturer's instructions (Sigma) and using a U-Quant Spectrophotometer (Bio-TEK Instruments, Winooski, Vt.).

Mitochondrial Morphology, EJ1 Localization, and MMP.

Cells were treated with 20 μmol/l CP, 20 μmol/l EJ1 (or FITC-labeled EJ1), and MitoTracker Red CMXRos (Molecular Probes, Carlsbad, Calif.), along with Hoechst 33342 (Invitrogen, Carlsbad, Calif.) nuclear stain. Images were taken on an Olympus IX71 and deconvolved using soft-WoRx 4.0 image analysis software (Applied Precision, Issaquah, Wash.). Images were brightened using Adobe Photoshop (-Image-Adjustments-Brightness/Contrast). Measurement of MMP was performed with the 5,5', 6, 6'-tetrachloro-1, 1', 3, 3'-tetraethyl-benzimidazolcarbocyanine iodide (JC-1) stain (Invitrogen). JC-1 aggregates fluoresce at 590 nm in the mitochondria, whereas cytoplasmically localized JC-1 monomers fluoresce at 529 nm.

Measurement of Intracellular ROS by Flow Cytometry.

Generation of intracellular ROS was evaluated by flow cytometry using the 2',7'-dichlorofluorescein diacetate probe (Invitrogen). Fluorescent cells were analyzed by a FACScan flow cytometer (BD Biosciences) at the Flow Cytometry Shared Service in the Arizona Cancer Center, and the excitation/emission wavelengths were set at 488 and 525 nm, respectively.

Mouse Experiments.

Tumor studies were performed as described in the study by Bitler et al. and Supplementary Method SM1, online. The number of metastases in the lungs in MMTV-PyMT mice was assessed in control (six mice) and EJ1-(seven mice) treated mice. Lungs from these mice were fixed, sectioned (10-μm thickness), and stained with hematoxylin and eosin, followed by counting of metastatic foci of five individual sections spanning 200 μm/mouse. A more detailed description of these methods can be found in Supplementary Method SM1, online.

Figure 12:
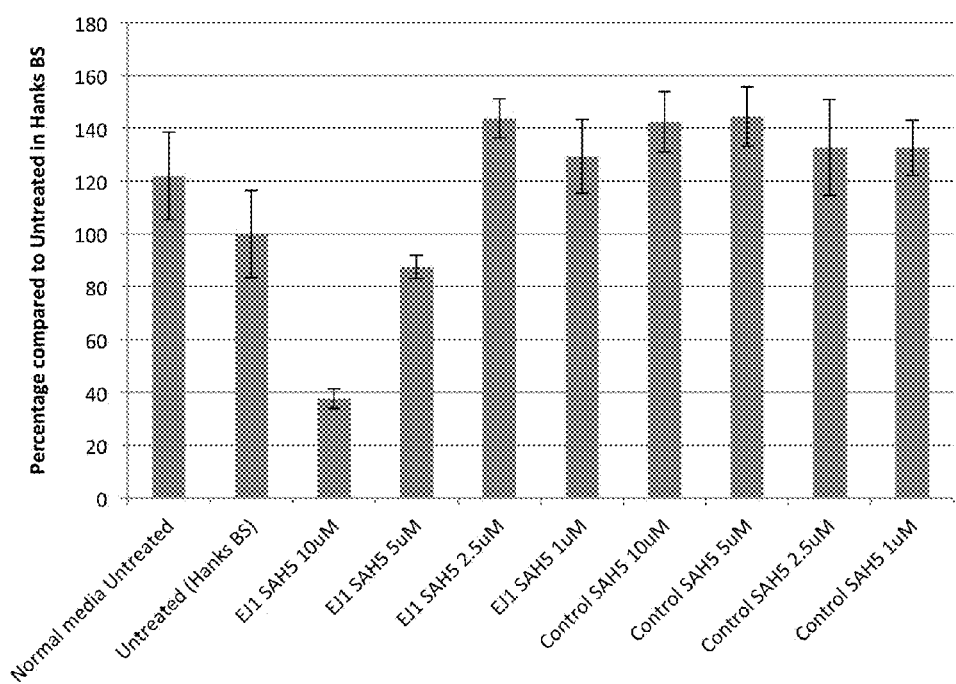
FIG. 12 shows treatment of ovarian cancer cells (erbB2 positive SKOV3 cells) with the peptides shown.

FIG. 12 shows ovarian cancer cells treated with the various inhibitor peptides shown. The erbB2 positive ovarian cancer cell line, SKOV3 was treated with SAH5-EJ1 for one hour with concentrations between 10 uM and 40 uM. Cells were then evaluated by MTT, and all cells were killed within one hour (data not shown). Lower concentrations were then evaluated, and it was found that one hour of treatment induced optimal cell killing from 5.0-10.0 μM.

Figure 13A:
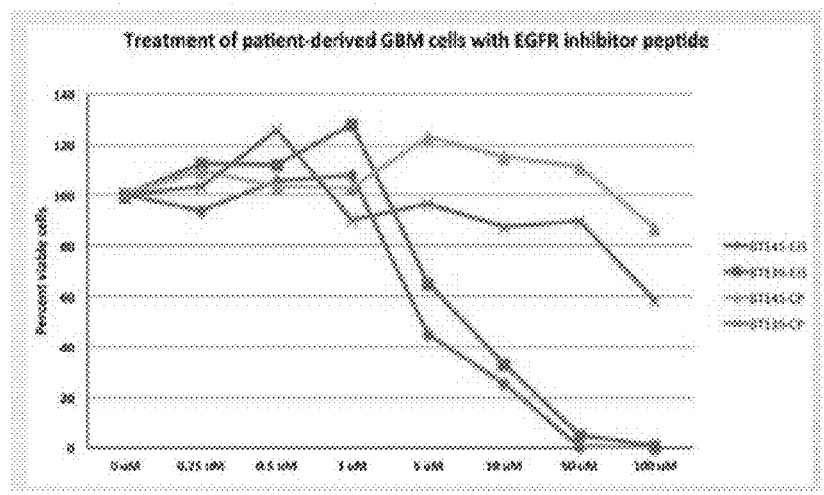
FIG. 13A and FIG. 13B show treatment of patient-derived GBM cells with various EGFR inhibitor peptides.
Figure 13B:
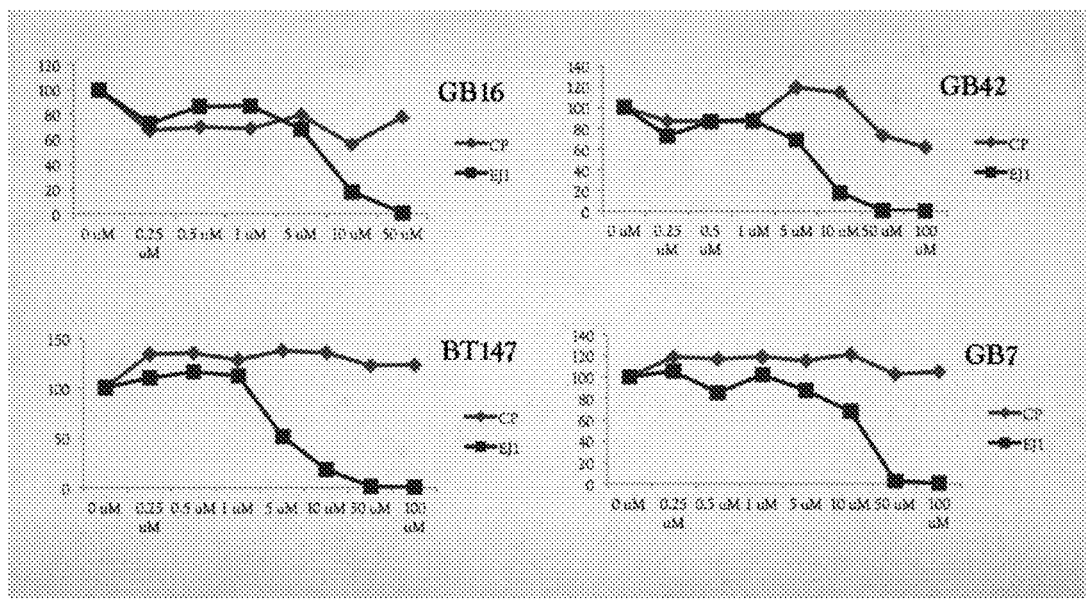

EGFR is amplified or mutated in more than 40% of glioblastoma multiforme (GBM) tumors. Referring to FIG. 13-14, inhibitor peptides of the present invention were used to treat GBM cells and tumors. FIG. 13A and FIG. 13B show that stapled EJ1 decreases viability of patient-derived glioma lines (e.g., BT145, BT147, GB16, GB7, GB42. FIG. 14 shows that daily subcutaneous injection of stapled EJ in mice (10 mg/kg) can decrease tumor growth in vivo.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An inhibitor peptide for combinatorial inactivation of ErbB1, ErbB2, and ErbB3, said inhibitor peptide comprising: SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, wherein the inhibitor peptide disrupts ErbB1, ErbB2, and ErbB3 activity.

2. The inhibitor peptide of claim 1, wherein the inhibitor peptide when administered in vivo is effective to inhibit growth of a tumor.

3. An inhibitor peptide for combinatorial inactivation of ErbB1, ErbB2, and ErbB3, said inhibitor peptide comprising: SEQ ID NO: 111, SEQ ID NO: 112, or SEQ ID NO: 113, wherein the inhibitor peptide disrupts ErbB1, ErbB2, and ErbB3 activity.

* * * * *

SEQUENCE LISTING

<160> NUMBER OF SEQ ID NOS: 113

<210> SEQ ID NO 1
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 1

Phe Met Arg Arg Arg His Ile Val Arg Lys Arg Thr Leu Arg Arg Leu
1               5                   10                  15

```
Leu Gln Glu Arg Glu
            20

<210> SEQ ID NO 2
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 2

Phe Arg Met His Arg Ile Arg Val Arg Thr Lys Leu Arg Leu Arg Leu
1               5                   10                  15

Arg Gln Glu Arg Glu
            20

<210> SEQ ID NO 3
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 3

Phe Met Arg Gln Arg His Ile Val Arg Gln Arg Thr Leu Arg Gln Leu
1               5                   10                  15

Leu Gln Glu Arg Glu
            20

<210> SEQ ID NO 4
<211> LENGTH: 15
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 4

Ile Val Arg Lys Arg Thr Leu Arg Arg Leu Leu Gln Glu Arg Glu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 5

Ile Val Arg Thr Lys Leu Arg Leu Arg Leu Arg Gln Glu Arg Glu
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 6

Arg Thr Leu Arg Arg Leu Leu Gln Glu Arg Glu
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 7

Phe Met Arg Arg Arg His Ile Val Arg Lys Arg Thr Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 8

Arg Arg Arg His Ile Val Arg Lys Arg Thr Leu Arg Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 9

Phe Arg Met His Arg Ile Arg Val Arg Thr Lys Leu Arg
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 10

Leu Leu Gln Glu Arg Glu
1               5

<210> SEQ ID NO 11
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 11

Arg Asp Arg His Ile Val Arg Asp Arg Thr Leu Arg Asp
1               5                   10

<210> SEQ ID NO 12
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence -continued

<400> SEQUENCE: 12

Phe Met Arg Asp Arg His Ile Val Arg Asp Arg Thr Leu Arg Asp Leu
1               5                   10                  15

Leu Gln Glu Arg Glu
            20

<210> SEQ ID NO 13
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 13

Tyr Ala Arg Ala Ala Ala Arg Gln Ala Arg Ala Phe Met Arg Arg
1               5                   10                  15

His Ile Val Arg Lys Arg Thr Leu Arg Leu Leu Gln Glu Arg Glu
                20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 14

Tyr Ala Arg Ala Ala Ala Arg Gln Ala Arg Ala Phe Arg Met His Arg
1               5                   10                  15

Ile Arg Val Arg Thr Lys Leu Arg Leu Arg Leu Arg Gln Glu Arg Glu
                20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 15

Tyr Ala Arg Ala Ala Ala Arg Gln Ala Arg Ala Phe Met Arg Gln Arg
1               5                   10                  15

His Ile Val Arg Gln Arg Thr Leu Arg Gln Leu Leu Gln Glu Arg Glu
                20                  25                  30

<210> SEQ ID NO 16
<211> LENGTH: 26
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 16

Tyr Ala Arg Ala Ala Ala Arg Gln Ala Arg Ala Ile Val Arg Lys Arg
1               5                   10                  15

Thr Leu Arg Arg Leu Leu Gln Glu Arg Glu
                20                  25

<210> SEQ ID NO 17
<211> LENGTH: 26

```
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 17

Tyr Ala Arg Ala Ala Ala Arg Gln Ala Arg Ala Ile Val Arg Thr Lys
1               5                   10                  15

Leu Arg Leu Arg Leu Arg Gln Glu Arg Glu
            20                  25

<210> SEQ ID NO 18
<211> LENGTH: 22
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 18

Tyr Ala Arg Ala Ala Ala Arg Gln Ala Arg Ala Arg Thr Leu Arg Arg
1               5                   10                  15

Leu Leu Gln Glu Arg Glu
            20

<210> SEQ ID NO 19
<211> LENGTH: 24
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 19

Tyr Ala Arg Ala Ala Ala Arg Gln Ala Arg Ala Phe Met Arg Arg Arg
1               5                   10                  15

His Ile Val Arg Lys Arg Thr Leu
            20

<210> SEQ ID NO 20
<211> LENGTH: 24
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 20

Tyr Ala Arg Ala Ala Ala Arg Gln Ala Arg Ala Arg Arg Arg His Ile
1               5                   10                  15

Val Arg Lys Arg Thr Leu Arg Arg
            20

<210> SEQ ID NO 21
<211> LENGTH: 24
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 21

Tyr Ala Arg Ala Ala Ala Arg Gln Ala Arg Ala Phe Arg Met His Arg
1               5                   10                  15
```

Ile Arg Val Arg Thr Lys Leu Arg
            20

<210> SEQ ID NO 22
<211> LENGTH: 23
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 22

Tyr Ala Arg Ala Ala Ala Arg Gln Ala Arg Ala Leu Leu Gln Glu Arg
1               5                   10                  15

Glu Leu Val Glu Pro Leu Thr
            20

<210> SEQ ID NO 23
<211> LENGTH: 24
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 23

Tyr Ala Arg Ala Ala Ala Arg Gln Ala Arg Ala Arg Asp Arg His Ile
1               5                   10                  15

Val Arg Asp Arg Thr Leu Arg Asp
            20

<210> SEQ ID NO 24
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 24

Tyr Ala Arg Ala Ala Ala Arg Gln Ala Arg Ala Phe Met Arg Asp Arg
1               5                   10                  15

His Ile Val Arg Asp Arg Thr Leu Arg Asp Leu Leu Gln Glu Arg Glu
            20                  25                  30

<210> SEQ ID NO 25
<211> LENGTH: 23
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 25

Tyr Ala Arg Ala Ala Ala Arg Gln Ala Arg Ala Ala Gln Glu Arg
1               5                   10                  15

Glu Ala Ala Glu Pro Leu Thr
            20

<210> SEQ ID NO 26
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 26

Tyr Ala Arg Ala Ala Ala Arg Gln Ala Arg Ala Phe Met Ala Ala Ala
1               5                   10                  15

His Ile Val Ala Ala Ala Thr Leu Ala Ala Leu Leu Gln Glu Arg Glu
            20                  25                  30

<210> SEQ ID NO 27
<211> LENGTH: 40
<212> TYPE: PRT
<213> ORGANISM: Homo sapiens

<400> SEQUENCE: 27

Leu Leu Leu Val Val Ala Leu Gly Ile Gly Leu Phe Met Arg Arg Arg
1               5                   10                  15

His Ile Val Arg Lys Arg Thr Leu Arg Arg Leu Leu Gln Glu Arg Glu
            20                  25                  30

Leu Val Glu Pro Leu Thr Pro Ser
        35                  40

<210> SEQ ID NO 28
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 28

Phe Met Arg Arg Arg His Ile Leu Arg Gln Arg Thr Val Arg Arg Leu
1               5                   10                  15

Leu Gln Glu Arg Glu
            20

<210> SEQ ID NO 29
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 29

Phe Met Arg Arg His His Val Leu Arg Lys Arg Thr Leu Lys Arg Leu
1               5                   10                  15

Leu Gln Glu Arg Glu
            20

<210> SEQ ID NO 30
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 30

Phe Met Lys Arg Arg His Ile Val His Lys His Thr Leu His Arg Ile
1               5                   10                  15

Leu Gln Asp Arg Glu
            20

<210> SEQ ID NO 31

```
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 31

Phe Met Lys Arg Arg His Ile Val His Lys His Thr Leu Arg Arg Arg
1               5                   10                  15

Leu Gln Glu Arg Glu
            20

<210> SEQ ID NO 32
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 32

Phe Met Lys Arg Gln His Ile Val His Lys His Thr Leu His Arg Ile
1               5                   10                  15

Leu Gln Glu Arg Glu
            20

<210> SEQ ID NO 33
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 33

Phe Met His Arg Arg His Leu Val Arg Arg Arg Thr Leu Arg His Leu
1               5                   10                  15

Leu Gln Glu Arg Glu
            20

<210> SEQ ID NO 34
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 34

Phe Met His Arg Lys Ile Val His Lys Lys Arg Thr Leu Arg His Leu
1               5                   10                  15

Leu Gln Glu Arg Glu
            20

<210> SEQ ID NO 35
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 35

Phe Met His Arg Arg His Leu Val His Arg Arg Thr Lys Arg His Leu
1               5                   10                  15
```

Leu Gln Glu Arg Glu
            20

<210> SEQ ID NO 36
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 36

Phe Met Arg Arg Arg His Ile Val Arg Lys Lys Thr Leu Arg Arg Leu
1               5                   10                  15

Leu Gln Asp Arg Asp
            20

<210> SEQ ID NO 37
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 37

Phe Met Arg Arg Arg Arg Ile Val Arg Lys Lys Thr Leu Arg Arg Arg
1               5                   10                  15

Leu Gln Glu Arg Glu
            20

<210> SEQ ID NO 38
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 38

Phe Met Arg Arg Gln His Ile Val Arg Gln Lys Thr Leu Arg Arg Gln
1               5                   10                  15

Leu Gln Glu Arg Glu
            20

<210> SEQ ID NO 39
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 39

Phe Met Arg Arg Arg His Ile Val Arg Lys Thr Leu Arg Lys Leu
1               5                   10                  15

Leu Gln Glu Arg Glu
            20

<210> SEQ ID NO 40
<211> LENGTH: 21
<212> TYPE: PRT
<213> ORGANISM: Artificial Sequence
<220> FEATURE:
<223> OTHER INFORMATION: Artificial peptide sequence related to EGFR juxtamembrane sequence

<400> SEQUENCE: 40

Phe Met Arg Arg Lys Val His Val Arg Lys Arg Thr Leu Arg Lys Leu
1               5                   10                  15

Leu Gln Glu Arg Glu
            20

<210> SEQ ID NO 41
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 41

Phe Met Arg Arg Gln His Leu Val Gln Lys Arg Thr Leu Arg Lys Leu
1               5                   10                  15

Leu Gln Glu Arg Glu
            20

<210> SEQ ID NO 42
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 42

Phe Met Arg Lys Arg His Ile Val Lys Arg Thr Leu Arg Arg Leu
1               5                   10                  15

Leu Gln Asp Arg Glu
            20

<210> SEQ ID NO 43
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 43

Phe Met Arg Lys Arg Arg Ile Val Arg Arg Thr Leu Lys Arg Leu
1               5                   10                  15

Leu Gln Glu Arg Glu
            20

<210> SEQ ID NO 44
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 44

Phe Met Arg Lys Arg His Ile Val Lys Lys Arg Thr Lys His Arg Leu
1               5                   10                  15

Leu Gln Glu Arg Asp
            20

```
<210> SEQ ID NO 45
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 45

Phe Met Arg His Arg His Ile Val Arg Lys Arg Thr Leu Arg Arg Leu
1               5                   10                  15

Leu Gln Glu Arg Glu
            20

<210> SEQ ID NO 46
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 46

Phe Met Arg His Arg His Ile Val Arg Lys Arg Thr Leu Arg Arg Leu
1               5                   10                  15

Leu Gln Glu Arg Glu
            20

<210> SEQ ID NO 47
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 47

Phe Met Arg His Arg Val Ile Val His His Arg Thr Leu Arg Arg Lys
1               5                   10                  15

Leu Gln Glu Arg Glu
            20

<210> SEQ ID NO 48
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 48

Phe Met Arg Arg Arg His Ile Val Arg Thr His Thr Leu Arg Lys Lys
1               5                   10                  15

Leu Gln Glu Arg Glu
            20

<210> SEQ ID NO 49
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 49

Phe Met Arg Arg Arg Gln Ile Val Arg Gln His Thr Leu Arg Lys Lys
```

-continued

```
                1               5                  10                 15

Leu Gln Glu Arg Glu
            20

<210> SEQ ID NO 50
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 50

Phe Met Arg Arg Arg His Ile Leu Leu Thr His Thr Leu Arg Lys Lys
1               5                  10                 15

Leu Gln Glu Arg Glu
            20

<210> SEQ ID NO 51
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 51

Phe Met Arg Arg Arg His Ile Val Arg Lys Lys Thr Leu Arg His Leu
1               5                  10                 15

Leu Gln Glu Arg Glu
            20

<210> SEQ ID NO 52
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 52

Phe Met Arg Arg Arg Lys Ile Val Arg Lys Lys Thr Leu Arg His Leu
1               5                  10                 15

Leu Gln Asp Arg Glu
            20

<210> SEQ ID NO 53
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 53

Phe Met Arg Arg Arg His Leu Val Leu Lys Lys Thr Leu Arg His Leu
1               5                  10                 15

Leu Gln Glu Arg Glu
            20

<210> SEQ ID NO 54
<211> LENGTH: 21
<212> TYPE: PRT
<213> ORGANISM: Artificial Sequence
<220> FEATURE:
```

<223> OTHER INFORMATION: Artificial peptide sequence related to EGFR
      juxtamembrane sequence

<400> SEQUENCE: 54

Phe Met Arg His Arg His Ile Val Arg Lys Arg Thr Leu Arg Lys Leu
1               5                   10                  15

Leu Gln Glu Arg Glu
            20

<210> SEQ ID NO 55
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 55

Phe Met Arg His Arg His Ile Val Arg Lys Arg Arg Arg Arg Lys Leu
1               5                   10                  15

Leu Gln Glu Arg Glu
            20

<210> SEQ ID NO 56
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 56

Phe Met Arg His Arg His Arg Val Arg Lys Arg Thr Arg Arg Lys Leu
1               5                   10                  15

Leu Gln Glu Arg Glu
            20

<210> SEQ ID NO 57
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 57

Phe Met Arg Lys Arg His Ile Val Arg Lys Arg Thr Leu Arg His Leu
1               5                   10                  15

Leu Gln Glu Arg Glu
            20

<210> SEQ ID NO 58
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 58

Phe Met Arg Lys Arg His Ile Val Arg Lys Arg Thr Leu Arg His Leu
1               5                   10                  15

Leu Gln Glu Arg Asp
            20

<210> SEQ ID NO 59
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 59

Phe Met Arg Lys Arg His Ile Val Arg Lys Lys Leu Arg His Leu
1               5                   10                  15

Leu Gln Asp Arg Asp
            20

<210> SEQ ID NO 60
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 60

Phe Met Arg His Arg His Ile Val Arg Lys Lys Thr Leu Arg Arg Leu
1               5                   10                  15

Leu Gln Glu Arg Glu
            20

<210> SEQ ID NO 61
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 61

Phe Met Arg His Arg Lys Leu Val Arg Lys Lys Thr Leu Arg Arg Leu
1               5                   10                  15

Leu Gln Glu Arg Glu
            20

<210> SEQ ID NO 62
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 62

Phe Met Arg His Arg His Ile Val Leu Leu Lys Thr Leu Arg Arg Leu
1               5                   10                  15

Leu Gln Glu Arg Glu
            20

<210> SEQ ID NO 63
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 63

```
Phe Met Arg Lys Arg His Ile Val Arg Lys His Thr Leu Arg Arg Leu
1               5                   10                  15

Leu Gln Glu Arg Glu
            20

<210> SEQ ID NO 64
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 64

Phe Met Arg Lys Arg His Ile Val Arg Lys His Gln Leu Gln Arg Leu
1               5                   10                  15

Leu Gln Glu Arg Glu
            20

<210> SEQ ID NO 65
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 65

Phe Met Arg Lys His His Ile Val Arg Lys His Thr Leu Arg Arg Leu
1               5                   10                  15

Gln Gln Glu Arg Glu
            20

<210> SEQ ID NO 66
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 66

Phe Arg Met His Lys Ile Arg Val Arg Thr Lys Leu Arg Leu Arg Leu
1               5                   10                  15

Arg Gln Glu Arg Glu
            20

<210> SEQ ID NO 67
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 67

Phe Arg Met His Arg Ile Arg Val Lys Thr Lys Leu Arg Leu Arg Leu
1               5                   10                  15

Arg Gln Asp Arg Glu
            20

<210> SEQ ID NO 68
<211> LENGTH: 21
<212> TYPE: PRT
<213> ORGANISM: Artificial Sequence
```

-continued

```
<220> FEATURE:
<223> OTHER INFORMATION: Artificial peptide sequence related to EGFR
      juxtamembrane sequence

<400> SEQUENCE: 68

Phe Arg Met His Arg Ile Arg Val Arg Thr Lys Leu Lys Leu Arg Leu
1               5                   10                  15

Arg Gln Glu Arg Glu
            20

<210> SEQ ID NO 69
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 69

Phe Arg Met His Arg Ile Arg Val Arg Thr Lys Leu Arg Leu Arg Leu
1               5                   10                  15

Lys Gln Glu Arg Glu
            20

<210> SEQ ID NO 70
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 70

Phe Arg Met His Arg Ile Gln Val Arg Thr Lys Leu Arg Gln Arg Leu
1               5                   10                  15

Arg Gln Asp Arg Glu
            20

<210> SEQ ID NO 71
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 71

Phe Met Arg Gln Arg His Ile Val Arg Gln Thr Leu Arg Gln Leu
1               5                   10                  15

Leu Gln Glu Arg Glu
            20

<210> SEQ ID NO 72
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 72

Phe Met Arg Gln Arg His Ile Val Lys Gln Arg Thr Leu Arg Gln Leu
1               5                   10                  15

Leu Gln Asp Arg Glu
            20
```

<210> SEQ ID NO 73
<211> LENGTH: 19
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 73

Phe Met Arg Gln Arg His Ile Val Arg Gln Arg Thr Leu Arg Gln Leu
1               5                   10                  15

Leu Gln Glu

<210> SEQ ID NO 74
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 74

Phe Met Arg Gln Arg His Ile Val Arg Gln Arg Thr Leu Arg Gln Leu
1               5                   10                  15

Leu Gln Glu Arg Glu
            20

<210> SEQ ID NO 75
<211> LENGTH: 20
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 75

Phe Met Arg Gln Arg His Ile Val Arg Gln Arg Thr Leu Lys Gln Leu
1               5                   10                  15

Leu Gln Asp Arg
            20

<210> SEQ ID NO 76
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 76

Phe Met Arg Gln Arg His Ile Val Arg Gln Leu Leu Arg Gln Leu
1               5                   10                  15

His Gln Glu Arg Glu
            20

<210> SEQ ID NO 77
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 77

```
Phe Met Arg Gln Arg His Ile Val Leu Gln Arg Thr Leu Arg Gln Leu
1               5                   10                  15

Leu Gln Glu Arg Glu
            20
```

<210> SEQ ID NO 78
<211> LENGTH: 19
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 78

```
Phe Met Arg Gln Arg His Leu Leu Lys Gln Arg Thr Leu Arg Gln Leu
1               5                   10                  15

Leu Gln Glu
```

<210> SEQ ID NO 79
<211> LENGTH: 19
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 79

```
Phe Met Arg Gln Arg His Leu Leu Lys Gln Gln Thr Leu Arg Arg Leu
1               5                   10                  15

Leu Gln Glu
```

<210> SEQ ID NO 80
<211> LENGTH: 14
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 80

```
Val Arg Lys Arg Thr Leu Arg Arg Leu Leu Gln Glu Arg Glu
1               5                   10
```

<210> SEQ ID NO 81
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 81

```
Arg Lys Arg Thr Leu Arg Arg Leu Leu Gln Glu Arg Glu
1               5                   10
```

<210> SEQ ID NO 82
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 82

```
Lys Arg Thr Leu Arg Arg Leu Leu Gln Glu Arg Glu
1               5                   10
```

```
<210> SEQ ID NO 83
<211> LENGTH: 11
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 83

Arg Thr Leu Arg Arg Leu Leu Gln Glu Arg Glu
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 84

Arg Lys Arg Thr Leu Arg Arg Gln Leu Gln Glu Arg Glu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 85

Lys Arg Thr Arg Arg Arg Arg Leu Gln Glu Arg Glu
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 86

Val Arg Lys Arg Val Leu Arg Arg Lys Lys Gln Glu Arg Glu
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 87

Val Arg Thr Lys Leu Arg Leu Arg Leu Arg Gln Glu Arg Glu
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Artificial peptide sequence related to EGFR
      juxtamembrane sequence
```

```
<400> SEQUENCE: 88

Arg Thr Lys Leu Arg Leu Arg Leu Arg Gln Glu Arg Glu
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 89

Thr Lys Leu Arg Leu Arg Leu Arg Gln Glu Arg Glu
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 90

Lys Leu Arg Leu Arg Leu Arg Gln Glu Arg Glu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 91

Val Arg Thr Lys Leu Arg Leu Arg Leu Arg Gln Glu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 92

Arg Thr Lys Leu Arg Leu Arg Leu Arg Gln Glu Arg
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 93

Thr Lys Leu Arg Leu Arg Leu Arg Gln Glu
1               5                   10

<210> SEQ ID NO 94
<211> LENGTH: 10
```

```
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 94

Lys Leu Arg Leu Arg Leu Arg Gln Glu Arg
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 95

Val Arg Thr Lys Leu Arg Gln Arg Leu Arg Gln Glu
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 96

Arg Thr Lys Leu Arg Leu Arg Leu Leu Gln Glu Arg
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 97

Gln Lys Leu Arg Leu Arg Leu Arg Gln Glu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Artificial peptide sequence related to EGFR
      juxtamembrane sequence

<400> SEQUENCE: 98

Lys Leu Arg Lys Arg Leu Lys Gln Glu Arg
1               5                   10

<210> SEQ ID NO 99
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (8)..(8)
<223> OTHER INFORMATION: R is
```

```
          (R)-2-{[(9H-fluoren-9-yl)methoxy]carbonylamino}-2-methyldec-9-
          enoic acid
<220> FEATURE:
<221> NAME/KEY: MOD_RES
<222> LOCATION: (15)..(15)
<223> OTHER INFORMATION: S is
          (S)-2-{[(99H-fluoren-9-yl)methoxy]carbonylamino}-2-methyl-hept-6-
          enoic acid

<400> SEQUENCE: 99

Phe Met Arg Arg Arg His Ile Arg Arg Lys Arg Thr Leu Arg Ser Leu
1               5                   10                  15

Leu Gln Glu Arg Glu
            20

<210> SEQ ID NO 100
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (9)..(9)
<223> OTHER INFORMATION: R is
          (R)-2-{[(9H-fluoren-9-yl)methoxy]carbonylamino}-2-methyldec-9-
          enoic acid
<220> FEATURE:
<221> NAME/KEY: MOD_RES
<222> LOCATION: (16)..(16)
<223> OTHER INFORMATION: S is
          (S)-2-{[(99H-fluoren-9-yl)methoxy]carbonylamino}-2-methyl-hept-6-
          enoic acid

<400> SEQUENCE: 100

Phe Met Arg Arg Arg His Ile Val Arg Lys Arg Thr Leu Arg Arg Ser
1               5                   10                  15

Leu Gln Glu Arg Glu
            20

<210> SEQ ID NO 101
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (1)..(1)
<223> OTHER INFORMATION: R is
          (R)-2-{[(9H-fluoren-9-yl)methoxy]carbonylamino}-2-methyldec-9-
          enoic acid
<220> FEATURE:
<221> NAME/KEY: MOD_RES
<222> LOCATION: (8)..(8)
<223> OTHER INFORMATION: S is
          (S)-2-{[(99H-fluoren-9-yl)methoxy]carbonylamino}-2-methyl-hept-6-
          enoic acid

<400> SEQUENCE: 101

Arg Met Arg Arg Arg His Ile Ser Arg Lys Arg Thr Leu Arg Arg Leu
1               5                   10                  15

Leu Gln Glu Arg Glu
            20

<210> SEQ ID NO 102
<211> LENGTH: 21
<212> TYPE: PRT
```

```
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (2)..(2)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (9)..(9)
<223> OTHER INFORMATION: S is
      (S)-2-{[(99H-fluoren-9-yl)methoxy]carbonylamino}-2-methyl-hept-6-
      enoic acid

<400> SEQUENCE: 102

Phe Arg Arg Arg Arg His Ile Val Ser Lys Arg Thr Leu Arg Arg Leu
1               5                   10                  15

Leu Gln Glu Arg Glu
            20

<210> SEQ ID NO 103
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (12)..(12)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (19)..(19)
<223> OTHER INFORMATION: S is
      (S)-2-{[(99H-fluoren-9-yl)methoxy]carbonylamino}-2-methyl-hept-6-
      enoic acid

<400> SEQUENCE: 103

Phe Met Arg Arg Arg His Ile Val Arg Lys Arg Arg Leu Arg Arg Leu
1               5                   10                  15

Leu Gln Ser Arg Glu
            20

<210> SEQ ID NO 104
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (3)..(3)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (10)..(10)
<223> OTHER INFORMATION: S is
      (S)-2-{[(99H-fluoren-9-yl)methoxy]carbonylamino}-2-methyl-hept-6-
      enoic acid

<400> SEQUENCE: 104

Phe Met Arg Arg Arg His Ile Val Arg Ser Arg Thr Leu Arg Arg Leu
1               5                   10                  15
```

Leu Gln Glu Arg Glu
            20

<210> SEQ ID NO 105
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (5)..(5)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (12)..(12)
<223> OTHER INFORMATION: S is
      (S)-2-{[(99H-fluoren-9-yl)methoxy]carbonylamino}-2-methyl-hept-6-
      enoic acid

<400> SEQUENCE: 105

Phe Met Arg Arg Arg His Ile Val Arg Lys Arg Ser Leu Arg Arg Leu
1               5                   10                  15

Leu Gln Glu Arg Glu
            20

<210> SEQ ID NO 106
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (6)..(6)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (13)..(13)
<223> OTHER INFORMATION: S is
      (S)-2-{[(99H-fluoren-9-yl)methoxy]carbonylamino}-2-methyl-hept-6-
      enoic acid

<400> SEQUENCE: 106

Phe Met Arg Arg Arg Arg Ile Val Arg Lys Arg Thr Ser Arg Arg Leu
1               5                   10                  15

Leu Gln Glu Arg Glu
            20

<210> SEQ ID NO 107
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (7)..(7)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (14)..(14)

```
<223> OTHER INFORMATION: S is
      (S)-2-{[(99H-fluoren-9-yl)methoxy]carbonylamino}-2-methyl-hept-6-
      enoic acid

<400> SEQUENCE: 107

Phe Met Arg Arg Arg His Arg Val Arg Lys Arg Thr Leu Ser Arg Leu
1               5                   10                  15

Leu Gln Glu Arg Glu
            20

<210> SEQ ID NO 108
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (10)..(10)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (17)..(17)
<223> OTHER INFORMATION: S is
      (S)-2-{[(99H-fluoren-9-yl)methoxy]carbonylamino}-2-methyl-hept-6-
      enoic acid

<400> SEQUENCE: 108

Phe Met Arg Arg Arg His Ile Val Arg Arg Arg Thr Leu Arg Arg Leu
1               5                   10                  15

Ser Gln Glu Arg Glu
            20

<210> SEQ ID NO 109
<211> LENGTH: 21
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (13)..(13)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (20)..(20)
<223> OTHER INFORMATION: S is
      (S)-2-{[(99H-fluoren-9-yl)methoxy]carbonylamino}-2-methyl-hept-6-
      enoic acid

<400> SEQUENCE: 109

Phe Met Arg Arg Arg His Ile Val Arg Lys Arg Thr Arg Arg Arg Leu
1               5                   10                  15

Leu Gln Glu Ser Glu
            20

<210> SEQ ID NO 110
<211> LENGTH: 11
<212> TYPE: PRT
<213> ORGANISM: Artificial Sequence
<220> FEATURE:
<223> OTHER INFORMATION: Cell-penetrating peptide (PTD-4)

<400> SEQUENCE: 110
```

Tyr Ala Arg Ala Ala Ala Arg Gln Ala Arg Ala
1               5                   10

<210> SEQ ID NO 111
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (19)..(19)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (26)..(26)
<223> OTHER INFORMATION: S is
      (S)-2-{[(99H-fluoren-9-yl)methoxy]carbonylamino}-2-methyl-hept-6-
      enoic acid

<400> SEQUENCE: 111

Tyr Ala Arg Ala Ala Ala Arg Gln Ala Arg Ala Phe Met Arg Arg
1               5                   10                  15

His Ile Arg Arg Lys Arg Thr Leu Arg Ser Leu Leu Gln Glu Arg Glu
                20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (13)..(13)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (20)..(20)
<223> OTHER INFORMATION: S is
      (S)-2-{[(99H-fluoren-9-yl)methoxy]carbonylamino}-2-methyl-hept-6-
      enoic acid

<400> SEQUENCE: 112

Tyr Ala Arg Ala Ala Ala Arg Gln Ala Arg Ala Phe Arg Arg Arg
1               5                   10                  15

His Ile Val Ser Lys Arg Thr Leu Arg Arg Leu Leu Gln Glu Arg Glu
                20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Artificial peptide sequence related to EGFR
      juxtamembrane sequence
<220> FEATURE:
<221> NAME/KEY: MOD_RES
<222> LOCATION: (23)..(23)
<223> OTHER INFORMATION: R is
      (R)-2-{[(9H-fluoren-9-yl)methoxy]carbonylamino}-2-methyldec-9-
      enoic acid
<220> FEATURE:
<221> NAME/KEY: MOD_RES
<222> LOCATION: (30)..(30)

```
<223> OTHER INFORMATION: S is
     (S)-2-{[(99H-fluoren-9-yl)methoxy]carbonylamino}-2-methyl-hept-6-
     enoic acid

<400> SEQUENCE: 113

Tyr Ala Arg Ala Ala Ala Arg Gln Ala Arg Ala Phe Met Arg Arg Arg
1               5                   10                  15

His Ile Val Arg Lys Arg Arg Leu Arg Arg Leu Leu Gln Ser Arg Glu
            20                  25                  30
```